United States Patent
Anderson et al.

(10) Patent No.: US 10,023,568 B2
(45) Date of Patent: Jul. 17, 2018

(54) NAPHTHYRIDINE DERIVATIVES USEFUL AS $\alpha_v\beta_6$ INTEGRIN ANTAGONISTS

(71) Applicant: GlaxoSmithKline Intellectual Property Development Limited, Brentford, Middlesex (GB)

(72) Inventors: Niall Andrew Anderson, Stevenage (GB); Brendan John Fallon, Stevenage (GB); John Martin Pritchard, Stevenage (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 14/778,095

(22) PCT Filed: Mar. 26, 2014

(86) PCT No.: PCT/EP2014/056013
§ 371 (c)(1),
(2) Date: Sep. 18, 2015

(87) PCT Pub. No.: WO2014/154725
PCT Pub. Date: Oct. 2, 2014

(65) Prior Publication Data
US 2016/0280705 A1  Sep. 29, 2016

(30) Foreign Application Priority Data

Mar. 28, 2013 (GB) .................................. 1305668.4

(51) Int. Cl.
*C07D 471/04* (2006.01)
(52) U.S. Cl.
CPC ................... *C07D 471/04* (2013.01)
(58) Field of Classification Search
None
See application file for complete search history.

(56) References Cited

U.S. PATENT DOCUMENTS

2004/0092454 A1   5/2004  Schadt et al.

FOREIGN PATENT DOCUMENTS

| WO | WO 99/30709 A1 | 6/1999 |
|---|---|---|
| WO | WO 99/31061 A1 | 6/1999 |
| WO | WO 00/72801 A2 | 12/2000 |
| WO | WO 00/78317 A1 | 12/2000 |
| WO | WO 01/24797 A1 | 4/2001 |
| WO | WO 01/34602 | 5/2001 |
| WO | WO 01/34602 A2 | 5/2001 |
| WO | WO 01/096334 A2 | 12/2001 |
| WO | WO 02/07730 A1 | 1/2002 |
| WO | WO 02/22616 A2 | 3/2002 |
| WO | WO 02/053099 A2 | 7/2002 |
| WO | WO2004/058254 A1 | 7/2004 |
| WO | WO 2004/092454 A2 | 10/2004 |
| WO | WO 2005/082889 A1 | 9/2005 |
| WO | WO 2008/118455 A1 | 10/2008 |
| WO | WO 2009/055418 A1 | 4/2009 |
| WO | WO 2011/111880 A1 | 9/2011 |
| WO | WO 2015/048819 A1 | 4/2015 |
| WO | WO 2016/046225 A1 | 3/2016 |
| WO | WO 2016/046226 A1 | 3/2016 |
| WO | WO 2016/046230 A1 | 3/2016 |
| WO | WO 2016/046241 A1 | 3/2016 |
| WO | WO2016046230 * | 3/2016 |
| WO | WO 2016/134223 A2 | 8/2016 |
| WO | WO 2016/145258 A1 | 9/2016 |
| WO | WO 2017/158072 A1 | 9/2017 |
| WO | WO 2017/162570 A1 | 9/2017 |
| WO | WO 2017/162572 A1 | 9/2017 |

OTHER PUBLICATIONS

Margadant, C. et al. Integrin-TGF-β crosstalk in fibrosis, cancer, and wound healing. EMBO Reports, 2010, p. 101.*
Woodcock, HV. et al. The treatment of idiopathic pulmonary fibrosis. F1000Prime Reports, 2014, p. 7.*
Cho, ME. et al. Pirfenidone: an anti-fibrotic and cytoprotective agent as therapy for progressive kidney disease. Expert Opin. Investig. Drugs. 2011, p. 2.*
Goodman, SL. et al. Integrins as therapeutic targets. Cell Press, 2012, p. 407.*
Hahm et al., "αvβ6 Integrin Regulates Renal Fibrosis and Inflammation in Alport Mouse", *The Amer. J. of Pathology*, vol. 170, No. 1, pp. 110-125 (2007).
Horan et al., "Partial Inhibition of Integrin αvβ6 Prevents Pulmonary Fibrosis without Exacerbating Inflammation", *Am. J. Respir. Crit. Care Med.*, vol. 177, pp. 56-65 (2008).

(Continued)

*Primary Examiner* — David K O'Dell
(74) *Attorney, Agent, or Firm* — Jane F. Djung; Kathryn A. Lutomski

(57) ABSTRACT

A compound of formula (I) or a salt thereof

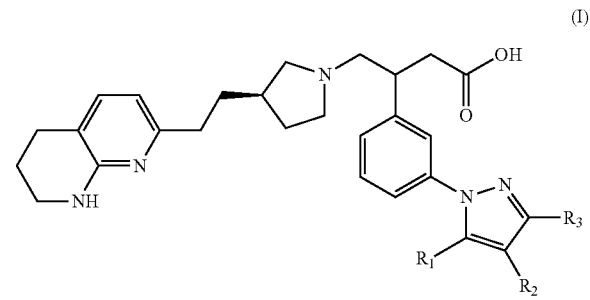

(I)

wherein
$R_1$ represents a hydrogen atom, a methyl group or a ethyl group
$R_2$ represents a hydrogen atom or a fluorine atom
$R_3$ represents a hydrogen atom, a methyl group or an ethyl group.

39 Claims, No Drawings

(56) References Cited

OTHER PUBLICATIONS

Popov et al., "Integrin αvβ6 is a marker of the progression of biliary and portal liver fibrosis and a novel target for antifibrotic therapies", *J. of Hepatology*, vol. 48, pp. 453-464 (2008).
Trevillian et al., "$\alpha_v\beta_6$ integrin expression in diseased and transplanted kidneys", *Kidney International*, vol. 66, pp. 1423-1433 (2004).
Cho, et al., "Pirfenidone: an anti-fibrotic and cytoprotective agent as therapy for progressive kidney disease", *Expert Opin. Investig. Drugs*, vol. 19, No. 2, pp. 275-283 (2010).
Goodman et al., "Integrins as therapeutic targets", *Trends in Pharmacological Sciences*, vol. 33, No. 7, pp. 405-412 (2012).
Hahm et al., "avB6 integrin Regulates Renal Fibrosis and Inflammation in Alport Mouse", *The American Journal of Pathology*, vol. 170, No. 1, pp. 110-125 (2007).
Horan et al., "Partial Inhibition of Integrin avB6 Prevents Pulmonary Fibrosis without Exacerbating Inflammation", *Am. J. Respir. Crit. Care Med.*, vol. 177, pp. 56-65 (2008).
Margadant, C. et al., "Integrin-TGF-βcrosstalk in fibrosis, cancer, and wound healing", *EMBO Reports*, vol. 11, No. 2, pp. 97-105 (2010).
Popov et al, "Integrin avB6 is a marker of the progression of biliary and portal liver fibrosis and a novel target for antifibrotic therapies", *Journal of Hepatology*, vol. 48 pp. 453-464 (2008).
Trevillian et al., "$\alpha_v$ $_{\beta 6}$ integrin expression in diseased and transplanted kidneys", *Kidney International*, vol. 66, pp. 1423-1433 (2004).
Whitman et al., "Nonpeptide αvβ3 antagonists. Part 9: Improved pharmacokinetic profile through the use of an aliphatic, des-amide backbone", *Bioorganic & Medicinal Chemistry Letters*, vol. 14, No. 17, pp. 4411-4415 (2004).
Woodcock, et al. The treatment of idiopathic pulmonary fibrosis, *F1000Prime Reports*, vol. 6, No. 16, pp. 1-9 (2014).
International Search Report for International Application No. PCT/EP2014/056013, dated May 9, 2014, 4 pages.
International Search Report for International Application No. PCT/EP2015/071776, dated Nov. 23, 2015, 4 pages.
International Search Report for International Application No. PCT/EP2015/071777, dated Nov. 26, 2015, 4 pages.
International Search Report for International Application No. PCT/EP2015/071782, dated Nov. 2, 2015, 4 pages.
International Search Report for International application No. PCT/EP2015/071798, dated Nov. 10, 2015, 4 pages.
International Search Report for International application No. PCT/EP2017/056204, dated May 15, 2017, 5 pages.
International Search Report for International application No. PCT/EP2017/056525, dated May 2, 2017, 4 pages.
International Search Report for International application No. PCT/EP2017/056527, dated May 2, 2017, 5 pages.
Notice of Allowance for U.S. Appl. No. 15/514,407, USPTO, dated Nov. 6, 2017, 16 pages.
Notice of Allowance for U.S. Appl. No. 15/514,414, USPTO, dated Nov. 9, 2017, 19 pages.
Restriction Requirement for U.S. Appl. No. 15/514,416, USPTO, dated Aug. 14, 2017, 12 pages.
Non-Final Office Action for U.S. Appl. No. 15/514,416, USPTO, dated Nov. 2, 2017, 18 pages.
Notice of Allowance for U.S. Appl. No. 15/514,399, USPTO, dated Dec. 15, 2017, 13 pages.
Notice of Allowance for U.S. Appl. No. 15/514,399, USPTO, dated Aug. 21, 2017, 11 pages.

\* cited by examiner

NAPHTHYRIDINE DERIVATIVES USEFUL AS $\alpha_v\beta_6$ INTEGRIN ANTAGONISTS

CROSS-REFERENCE TO RELATED APPLICATIONS

This application is filed pursuant to 35 USC 371 as a United States National Phase Application of International Patent Application Serial No. PCT/EP2014/056013 filed on Mar. 26, 2014, which claims priority from 1305668.4 filed on Mar. 28, 2013 in the United Kingdom.

FIELD OF THE INVENTION

The present invention relates to pyrrolidine compounds being $\alpha_v\beta_6$ integrin antagonists, pharmaceutical compositions comprising such compounds and to their use in therapy, especially in the treatment of conditions for which an $\alpha_v\beta_6$ integrin antagonist is indicated, for the use of a compound in the manufacture of a medicament for the treatment of conditions in which an antagonist of $\alpha_v\beta_6$ integrin is indicated and a method for the treatment or prophylaxis of disorders in which antagonism of $\alpha_v\beta_6$ integrin is indicated in a human, and to compounds which may be used as intermediates for the manufacture of such compounds.

BACKGROUND OF THE INVENTION

Integrin superfamily proteins are heterodimeric cell surface receptors, composed of an alpha and beta subunit. 18 alpha and 8 beta subunits have been reported, which have been demonstrated to form 24 distinct alpha/beta heterodimers. Each chain comprises a large extracellular domain (>640 amino acids for the beta subunit, >940 amino acids for the alpha subunit), with a transmembrane spanning region of around 20 amino acids per chain, and generally a short cytoplasmic tail of 30-50 amino acids per chain. Different integrins have been shown to participate in a plethora of cellular biologies, including cell adhesion to the extracellular matrix, cell-cell interactions, and effects on cell migration, proliferation, differentiation and survival (Barczyk et al, *Cell and Tissue Research*, 2010, 339, 269).

Integrin receptors interact with binding proteins via short protein-protein binding interfaces with ligands and the integrin family can be grouped into sub-families that share similar binding recognition motifs in such ligands. A major subfamily is the RGD-integrins, which recognise ligands that contain an RGD (Arginine-glycine-aspartic acid) motif within their protein sequence. There are 8 integrins in this sub-family, namely $\alpha_v\beta_1$, $\alpha_v\beta_3$, $\alpha_v\beta_5$, $\alpha_v\beta_6$, $\alpha_{v1}\beta_8$, $\alpha_{IIb}\beta_3$, $\alpha_5\beta_1$, $\alpha_8\beta_1$, where nomenclature demonstrates that $\alpha_v\beta_1$, $\alpha_v\beta_3$, $\alpha_v\beta_5$, $\alpha_v\beta_6$, & $\alpha_v\beta_8$ share a common V subunit with a divergent β subunit, and $\alpha_v\beta_1$, $\alpha_5\beta_1$ & $\alpha_8\beta_1$ share a common $\beta_1$ subunit with a divergent a subunit. The $\beta_1$ subunit has been shown to pair with 11 different a subunits, of which only the 3 listed above commonly recognise the RGD peptide motif. (Humphries et al, *Journal of Cell Science*, 2006, 119, 3901).

Within the 8 RGD-binding integrins are different binding affinities and specificities for different RGD-containing ligands. Ligands include proteins such as fibronectin, vitronectin, osteopontin, and the latency associated peptides (LAPs) of Transforming growth factor $\beta_1$ and $\beta_3$ (TGF$\beta_1$ and TGF$\beta_3$). The binding to the LAPs of TGF$\beta_1$ and TGF$\beta_3$ has been shown in several systems to enable activation of the TGF$\beta_1$ and TGF$\beta_3$ biological activities, and subsequent TGFβ-driven biologies (Worthington et al, *Trends in Biochemical Sciences*, 2011, 36, 47). The specific binding of RGD integrins to such ligands depends on a number of factors, depending on the cell phenotype. The diversity of such ligands, coupled with expression patterns of RGD-binding integrins, generates multiple opportunities for disease intervention. Such diseases include fibrotic diseases (Margadant et al, EMBO reports, 2010, 11, 97), inflammatory disorders, cancer (Desgrosellier et al, *Nature Reviews Cancer*, 2010, 10, 9), restenosis, and other diseases with an angiogenic component (Weis et al, *Cold Spring. Harb. Perspect. Med.* 2011, 1, a006478).

A significant number of $\alpha_v$ integrin antagonists (Goodman et al, *Trends in Pharmacological Sciences*, 2012, 33, 405) have been disclosed in the literature including antagonist antibodies, small peptides and compounds. For antibodies these include the pan-$\alpha_v$ antagonist Intetumumab, the selective $\alpha_v\beta_3$ antagonist Etaracizumab, and the selective $\alpha_v\beta_6$ antagonist STX-100. Cilengitide is a cyclic peptide antagonist that inhibits both $\alpha_v\beta_3$ and $\alpha_v\beta_5$, and SB-267268 is an example of a compound (Wilkinson-Berka et al, *Invest. Ophthalmol. Vis. Sci.*, 2006, 47, 1600), which inhibits both $\alpha_v\beta_3$ and $\alpha_v\beta_5$. Invention of compounds to act as antagonists of differing combinations of $\alpha_v$ integrins enables novel agents to be generated and tailored for specific disease indications.

Pulmonary fibrosis represents the end stage of several interstitial lung diseases, including the idiopathic interstitial pneumonias, and is characterised by the excessive deposition of extracellular matrix within the pulmonary interstitium. Among the idiopathic interstitial pneumonias, idiopathic pulmonary fibrosis (IPF) represents the commonest and most fatal condition with a median survival of 3 to 5 years following diagnosis. Fibrosis in IPF is generally progressive, refractory to current pharmacological intervention and inexorably leads to respiratory failure due to obliteration of functional alveolar units. IPF affects approximately 500,000 people in the USA and Europe. This condition therefore represents a major unmet medical need for which novel therapeutic approaches are urgently required (Datta A et al, Novel therapeutic approaches for pulmonary fibrosis, *British Journal of Pharmacology* 2011 163: 141-172).

There are strong in vitro, experimental animal and IPF patient immunohistochemistry data to support a key role for the epithelial-restricted integrin, $\alpha_v\beta_6$, in the activation of TGF-β1. Expression of this integrin is low in normal epithelial tissues and is significantly up-regulated in injured and inflamed epithelia including the activated epithelium in IPF. Targeting this integrin therefore reduces the theoretical possibility of interfering with wider TGF-β homeostatic roles. Partial inhibition of the $\alpha_v\beta_6$ integrin by antibody blockade has been shown to prevent pulmonary fibrosis without exacerbating inflammation (Horan G S et al Partial inhibition of integrin $\alpha_v\beta_6$ prevents pulmonary fibrosis without exacerbating inflammation. *Am J Respir Crit Care Med* 2008 177: 56-65)

The $\alpha_v\beta_3$ integrin is expressed on a number of cell types including vascular endothelium where it has been characterised as a regulator of barrier resistance. Data in animal models of acute lung injury and sepsis have demonstrated a significant role for this integrin in vascular leak since knockout mice show markedly enhanced vessel leak leading to pulmonary oedema or death. Furthermore antibodies capable of inhibiting $\alpha_v\beta_3$ function caused dramatic increases in monolayer permeability in human pulmonary artery and umbilical vein endothelial cells in response to multiple growth factors. These data suggest a protective role for $\alpha_v\beta_3$ in the maintenance of vascular endothelial integrity following vessel stimulation and that inhibition of this function could drive pathogenic responses in a chronic disease setting (Su et al Absence of integrin $\alpha_v\beta_3$ enhances vascular leak in mice by inhibiting endothelial cortical actin formation *Am J Respir Crit Care Med* 2012 185: 58-66). Thus, selectivity for $\alpha_v\beta_6$ over $\alpha_v\beta_3$ may provide a safety advantage.

It is an object of the invention to provide $\alpha_v\beta_6$ antagonists.

BRIEF SUMMARY OF THE INVENTION

In a first aspect of the present invention, there is provided a compound of formula (I) or a salt thereof, more particularly a compound of formula (I) or a pharmaceutically acceptable salt thereof

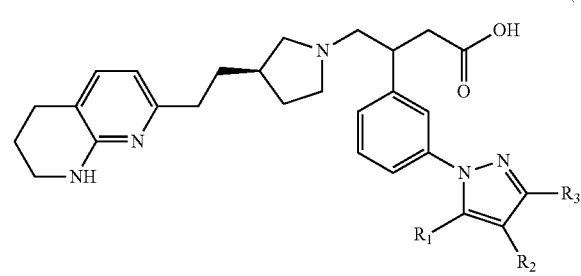

(I)

wherein $R_1$ represents a hydrogen atom, a methyl group or an ethyl group $R_2$ represents a hydrogen atom or a fluorine atom $R_3$ represents a hydrogen atom, a methyl group or an ethyl group.

Compounds of formula (I) and their salts have $\alpha_v\beta_6$ antagonist activity and are believed to be of potential use for the treatment or prophylaxis of certain disorders.

In a second aspect of the present invention, there is provided a pharmaceutical composition comprising a compound of formula (I) or a pharmaceutically acceptable salt thereof and one or more pharmaceutically acceptable carriers, diluents or excipients.

In a third aspect of the present invention, there is provided a compound of formula (I), or a pharmaceutically acceptable salt thereof for use in therapy, in particular in the treatment of a disease or condition for which an $\alpha_v\beta_6$ integrin receptor antagonist is indicated.

In a fourth aspect of the present invention, there is provided a method of treatment or prophylaxis of a disease or condition for which an $\alpha_v\beta_6$ integrin receptor antagonist is indicated in a human in need thereof which comprises administering to a human in need thereof a therapeutically effective amount of compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of a disease or condition for which an $\alpha_v\beta_6$ integrin receptor antagonist is indicated.

DETAILED DESCRIPTION OF THE INVENTION

In a first aspect of the invention there is provided a compound of formula (I) or a salt thereof

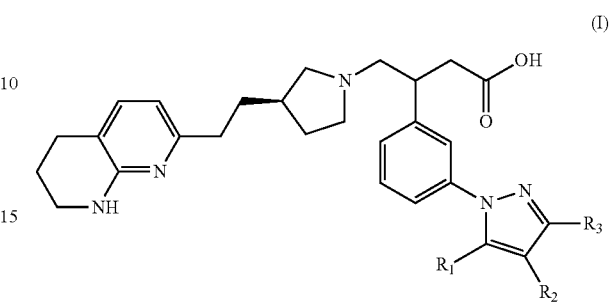

(I)

wherein $R_1$ represents a hydrogen atom, a methyl group or an ethyl group $R_2$ represents a hydrogen atom or a fluorine atom $R_3$ represents a hydrogen atom, a methyl group or an ethyl group.

In some embodiments the compound of formula (I) has the configuration:

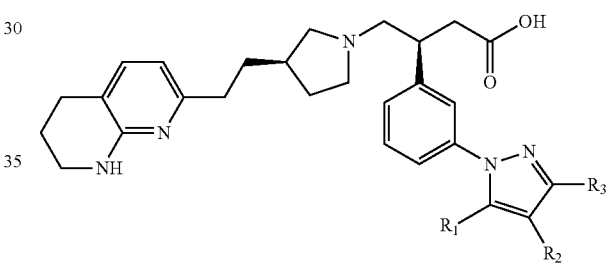

It is to be understood that the present invention covers all combinations of particular and preferred groups described hereinabove.

In some embodiments, $R_1$ represents a methyl group, $R_2$ represents a hydrogen atom and $R_3$ represents a methyl group.

In some embodiments, $R_1$ represents a methyl group, $R_2$ represents a hydrogen atom and $R_3$ represents a hydrogen atom.

In some embodiments, $R_1$ represents a methyl group, $R_2$ represents a fluorine group and $R_3$ represents methyl group.

In some embodiments, $R_1$ represents a hydrogen atom, $R_2$ represents a hydrogen atom and $R_3$ represents a hydrogen atom.

In some embodiments, $R_1$ represents an ethyl group, $R_2$ represents a hydrogen atom and $R_3$ represents a methyl group.

In some embodiments, $R_1$ represents an ethyl group, $R_2$ represents a hydrogen atom and $R_3$ represents an ethyl group.

In some embodiments, $R_1$ represents a hydrogen atom, $R_2$ represents a hydrogen atom and $R_3$ represents a methyl group.

In one embodiment the compound is selected from:

3-(3-(3,5-Dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid;

3-(3-(5-Methyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid;

3-(3-(5-Ethyl-3-methyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid;

3-(3-(1H-Pyrazol-1-yl)phenyl)-4-((R)-3-(2-(5,6,7,8-tetrahydro-1,8-naphthyridin-2-yl)ethyl)pyrrolidin-1-yl)butanoic acid;

3-(3-(3,5-Diethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid;

3-(3-(4-Fluoro-3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid;

3-(3-(3-Methyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid;

or a pharmaceutically acceptable salt thereof.

In one embodiment the compound is:

3-(3-(3,5-Dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid;

or a pharmaceutically acceptable salt thereof.

It will be appreciated that the present invention covers compounds of formula (I) as the free base and as salts thereof, for example as a pharmaceutically acceptable salt thereof. In one embodiment the invention relates to compounds of formula (I) or a pharmaceutically acceptable salt thereof.

For a review on suitable salts see Berge et al., *J. Pharm. Sci.*, 66:1-19, (1977). Suitable pharmaceutically acceptable salts are listed in P H Stahl and C G Wermuth, editors, *Handbook of Pharmaceutical Salts; Properties, Selection and Use*, Weinheim/Surich: Wiley—VCH/VHCA, 2002. Suitable pharmaceutically acceptable salts can include acid addition salts with inorganic acids such, for example, as hydrochloric acid, hydrobromic acid, orthophosphoric acid, nitric acid, phosphoric acid, or sulphuric acid, or with organic acids such, for example as methanesulphonic acid, ethanesulphonic acid, p-toluenesulphonic acid, acetic acid, propionic acid, lactic acid, citric acid, fumaric acid, malic acid, succinic acid, salicylic acid, maleic acid, glycerophosphoric acid, tartaric, benzoic, glutamic, aspartic, benzenesulphonic, naphthalenesulphonic such as 2-naphthalenesulphonic, hexanoic acid or acetylsalicylic acid. Typically, a pharmaceutically acceptable salt may be readily prepared by using a desired acid or base as appropriate. The resultant salt may precipitate from solution and be collected by filtration or may be recovered by evaporation of the solvent.

Other non-pharmaceutically acceptable salts, e.g. formates, oxalates or trifluoroacetates, may be used, for example in the isolation of the compounds of formula (I), and are included within the scope of this invention.

A pharmaceutically acceptable base addition salt can be formed by reaction of a compound of formula (I) with a suitable inorganic or organic base, (e.g. triethylamine, ethanolamine, triethanolamine, choline, arginine, lysine or histidine), optionally in a suitable solvent, to give the base addition salt which is usually isolated, for example, by crystallisation and filtration. Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

In one embodiment the compound of formula (I) is in the form of a free base, for example, 3-(3-(3,5-Dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid.

In another embodiment the compound of formula (I) is a hydrochloride salt, for example, 3-(3-(3,5-Dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid hydrochloride salt.

The invention includes within its scope all possible stoichiometric and non-stoichiometric forms of the salts of the compounds of formula (I).

It will be appreciated that many organic compounds can form complexes with solvents in which they are reacted or from which they are precipitated or crystallized. These complexes are known as "solvates". For example, a complex with water is known as a "hydrate". Solvents with high boiling points and/or capable of forming hydrogen bonds such as water, xylene, N-methyl pyrrolidinone, methanol and ethanol may be used to form solvates. Methods for identification of solvates include, but are not limited to, NMR and microanalysis. Solvates of the compounds of formula (I) are within the scope of the invention.

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

It will be appreciated that crystalline forms may be optionally hydrated or solvated. This invention includes within the scope of compounds of formula (I) stoichiometric hydrates as well as compounds of formula (I) containing variable amounts of water. Suitable solvates include pharmaceutically acceptable solvates, such as hydrates. Solvates include stoichiometric solvates and non-stoichiometric solvates.

The compounds described herein contain two asymmetric centres so that optical isomers, e.g. diastereoisomers may be formed. Accordingly, the present invention encompasses isomers of the compounds of formula (I) whether as individual isomers isolated such as to be substantially free of the other isomer (i.e. pure) or as mixtures. An individual isomer isolated such as to be substantially free of the other isomer (i.e. pure) may be isolated such that less than 10%, particularly less than about 1%, for example less than about 0.1% of the other isomer is present.

It will be understood by those skilled in the art that certain diastereoisomers may be less active than others and that the activity of an individual diastereoisomer may fall below a selected limit.

In one embodiment, the compound of formula (I) is (S)-3-(3-(3,5-dimethylpyrazol-1-yl)phenyl)-4-((R)-3-(2-(5,6,7,8-tetrahydro-1,8-naphthyridin-2-yl)ethyl)pyrrolidin-1-yl)butanoic acid

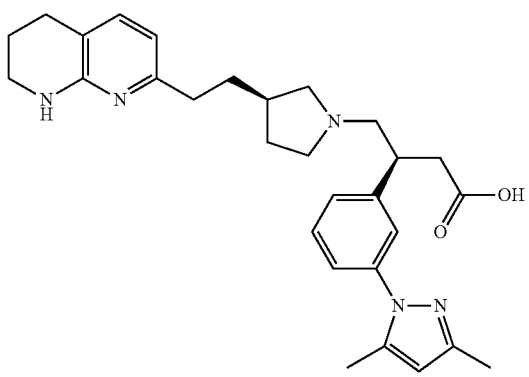

In another embodiment the compound of formula (I) is (S)-3-(3-(3,5-dimethylpyrazol-1-yl)phenyl)-4-((R)-3-(2-(5,6,7,8-tetrahydro-1,8-naphthyridin-2-yl)ethyl)pyrrolidin-1-yl)butanoic acid hydrochloride salt.

Separation of isomers may be achieved by conventional techniques known to those skilled in the art, e.g. by fractional crystallisation, chromatography or HPLC.

Compounds of formula (I) may exist in one of several tautomeric forms. It will be understood that the present invention encompasses all tautomers of the compounds of formula (I) whether as individual tautomers or as mixtures thereof.

It will be appreciated from the foregoing that included within the scope of the invention are solvates, isomers and polymorphic forms of the compounds of formula (I) and salts thereof.

Compound Preparation

The compounds of the invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

Compounds of structural formula (I) may be prepared by a process involving first deprotection of a compound of structural formula (II), i.e. cleavage of the ester group, followed by conversion to a salt:

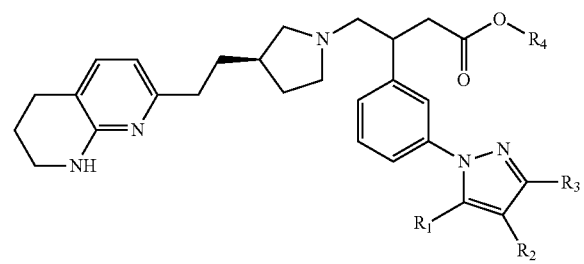

where $R_1$, $R_2$ and $R_3$ are as defined above and $R_4$ is a $C_1$ to $C_6$ alkyl group for example a tert-Bu, iso-propyl, ethyl or methyl group.

A sixth aspect of the invention provides a compound of formula (II).

In one embodiment, the compound of formula (II) has the configuration:

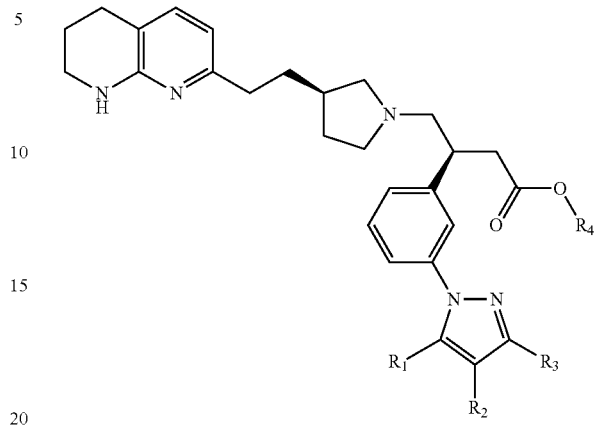

The deprotection of compound of structural formula (II) where $R_4$ is tert-Bu may be accomplished by acid hydrolysis using for example hydrochloric, hydrobromic, sulfuric, or trifluoroacetic acid, in an inert solvent, such as DCM, 2-methyl-tetrahydrofuran, tetrahydrofuran, 1,4-dioxane or cyclopentyl methyl ether.

Alternatively the deprotection of compound of structural formula (II) where $R_4$ is methyl may be accomplished by base hydrolysis using for example aqueous sodium hydroxide or potassium hydroxide in a suitable solvent, such as methanol.

After the cleavage of the ester group the resulting product may be converted to the required salt by methods well known to those skilled in the art.

In one embodiment the conversion of the free base to the hydrochloride salt is achieved by treatment of an acetonitrile solution of the free base with an aqueous hydrochloric acid solution, concentration of the resulting salt solution and crystallisation from acetonitrile.

Compounds of structural formula (II) may be obtained by catalytic hydrogenation over a catalyst, such as palladium or rhodium on carbon, of compounds of structural formula (III) where $R_1$, $R_2$, $R_3$ and $R_4$ are as defined above. The hydrogenation may be carried out at atmospheric pressure, or slightly higher pressure of hydrogen gas, such as 2 to 10 atmospheres, in a suitable solvent such as EtOH, MeOH or a mixture of both.

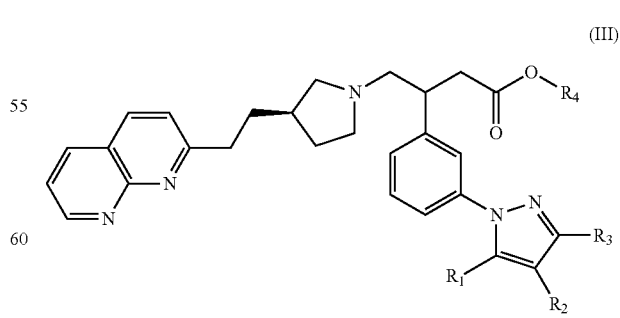

Compounds of structural formula (III) may be prepared by a process involving reaction of compounds of structural formula (IV) with a boronic acid of structural formula (V) in the presence of a suitable catalyst, optionally in the presence of a chiral ligand, at an elevated temperature, and in the presence of a base.

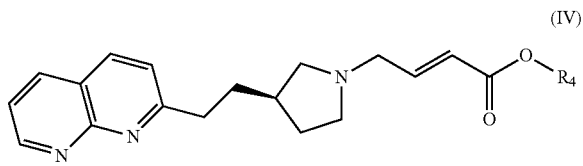

(IV)

where $R_1$, $R_2$, $R_3$ and $R_4$ are as defined above, and the geometry of the double bond may be (E) or mixture of (E) and (Z) isomers, preferably pure (E) isomer.

Compounds of structural formula (V) where $R_1$, $R_2$, $R_3$ are as defined above, and $R_5$ represents either hydrogen, or a $C_1$ to $C_6$ alkyl group, such as 2, 3-dimethylbutane-2, 3-diol (pinacol).

Compounds of structural formula (V) may be used as the pure boronic acid ($R_5$=H), or as boronic acid ester ($R_5$=alkyl group), which may be converted in situ to the boronic acid in the presence of water and a base, such as potassium hydroxide.

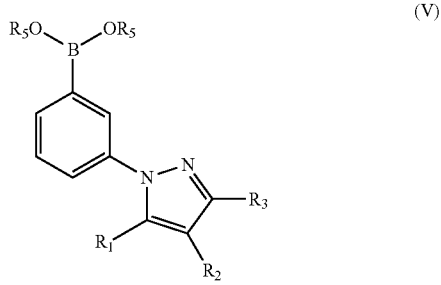

(V)

The process of condensing compounds of structural formulae (IV) and (V) is performed in the presence of a suitable catalyst, such as a rhodium catalyst, preferably chloro(1,5-cyclooctadiene)rhodium(I) dimer in approximately 5%, and in a water-miscible inert solvent, such as 1,4-dioxane, in the presence of base, such as potassium hydroxide, at elevated temperature, such as 50 to 90° C. The condensation process is carried out under strictly anaerobic conditions, where the reaction mixture is purged with an inert gas, such as nitrogen, and evacuated under reduced pressure, repeating the process of evacuation and purging with nitrogen several times, for example three times.

This condensation process produces two diastereoisomers, in approximately 1:1 ratio, which can be separated by crystallisation, chromatography, or by HPLC. Preferred method of separation is chiral HPLC on a chiral support, such as Chiralpak column. The ratio of the diastereoisomers formed can be increased substantially to for example approximately 80:20, in the presence of 10% of additives, such as chiral ligands. Such additives include enantiomerically pure phosphine ligands, for example (R)-(+)-2,2'-bis(diphenylphosphino)-1,1'-binaphthalene [(R)-BINAP], which provides as the major isomer the biologically more active diastereoisomer.

The diastereoisomeric ratio was found to be dependent on the size of the alkyl group $R_4$. Thus, when $R_4$ is tertiary, a higher ratio of the desired major isomer was obtained. A preferred alkyl group $R_4$ is tert-Bu which produced a diastereoisomeric ratio of up to 95:5. The diastereoisomeric ratio can be further increased to, for example greater than 99:1, by chiral HPLC, or by crystallisation. On a larger scale a diastereoisomeric ratio of 90:10 was obtained when the alkyl group $R_4$ was methyl.

Compounds of structural formula (IV) can be prepared by reaction of (R)-2-(2-(pyrrolidin-3-yl)ethyl)-1,8-naphthyridine [compound of structural formula (VI)] with a compound of structural formula (VII), in the presence of approximately 10% of a suitable palladium catalyst, in a suitable inert solvent, such as DCM, in the presence of a tertiary amine base, such as triethylamine, or diisopropylethylamine, and at ambient temperature. Suitable palladium catalysts preferably possess a bidentate ligand, such as two diphenylphosphine groups, for example, 1,1'-bis(diphenylphosphino)ferrocene]dichloropalladium(II) [Pd(dppf)Cl$_2$]. Compound of structural formula (VI) can be used as the free base, or be generated in situ from a salt, such as the dihydrochloride salt, in the presence of a tertiary amine base.

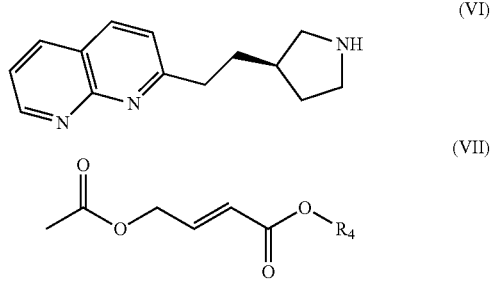

(VI)

(VII)

Compound of structural formula (VI) [(k)-2-(2-(pyrrolidin-3-yl)ethyl)-1,8-naphthyridine] may be prepared by methods described herein. By way of illustration (k)-2-(2-(pyrrolidin-3-yl)ethyl)-1,8-naphthyridine can be prepared by methods described in Scheme 1.

Scheme 1

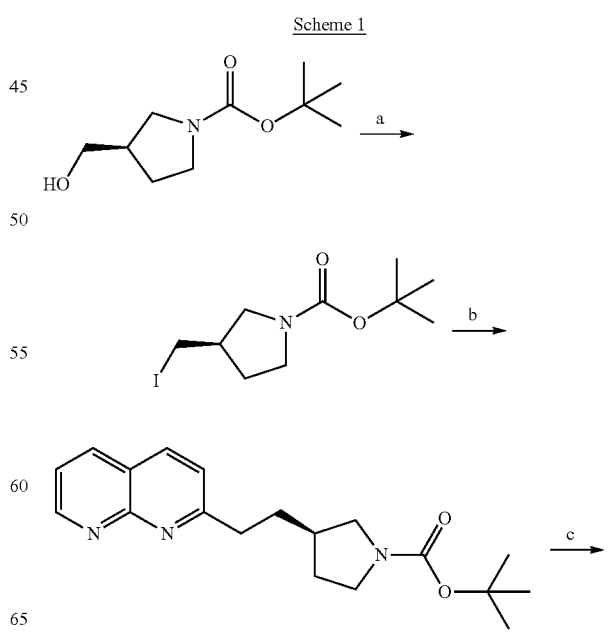

-continued

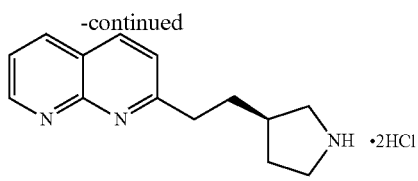

Reagents and conditions: (a) iodine, imidazole, triphenylphosphine, DCM, 0° C.;
(b) 2-methyl-[1,8]-naphthyridine, LiN(TMS)$_2$, THF, 0° C.;
(c) 4M HCl in dioxane.

(R)-tert-butyl 3-(hydroxymethyl)pyrrolidine-1-carboxylate is commercially available from Fluorochem, or BePharm Ltd, and 2-methyl-[1,8]-naphthyridine is commercially available, for example, from Manchester Organics Ltd, Aldrich, or Alfa Aesar.

Compound of structural formula (VII) may be prepared by methods described herein. By way of illustration compound of structural formula (VI), where R$_4$ is tert-butyl, and the double bond having the (E) geometry, can be prepared by the method described in Scheme 2.

Scheme 2

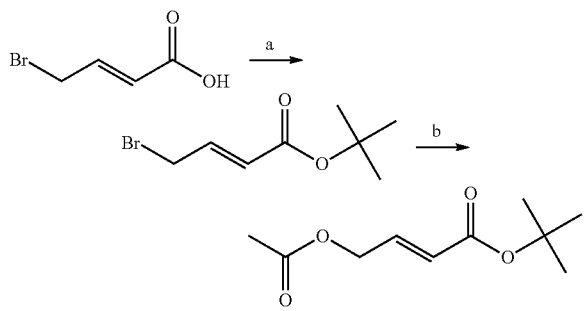

Reagents and conditions: (a) isobutylene, conc. H$_2$SO$_4$, diethyl ether, 24 h;
(b) potassium acetate, acetonitrile, 60° C., 4 h.

(E)-4-Bromobut-2-enoic acid was prepared according to literature procedure [T. Den Hartog, D. J. Van Dijken, A. J. Minnaard, B. L. Feringa *Tetrahedron: Asymmetry* 2010, 21, 1574-1584].

Compound of structural formula (VII) where R$_4$ is methyl can be prepared by methods described herein. For example, (E)-methyl 4-acetoxybut-2-enoate may be prepared by reaction of commercially available (E) methyl 4-bromobut-2-enoate with an acetate salt, such as potassium or sodium acetate in a suitable solvent, such as acetonitrile and at an elevated temperature, such as 45-55° C.

Compounds of structural formula (V) can be prepared from compound of structural formula (VIII), where R$_1$, R$_2$, and R$_3$ are as defined hereinbefore.

(VIII)

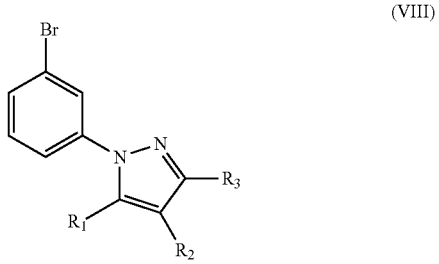

Compounds of structural formula (V) where R$_5$ is H can be prepared by a three-step process involving reaction of compounds of structural formula (VIII) with an organolithium reagent, such as n-butyllithium, in an inert solvent, such as THF or 2-methyl-tetrahydrofuran, at low temperature, such as between −60 and −78° C., and in an inert atmosphere of nitrogen or argon, followed by reaction with a trialkyl borate ester, such as tri(isopropyl) borate, and finally hydrolysis.

Alternatively, compounds of structural formula (V), where R$_5$ is pinacol, can be prepared by reaction of compounds of structural formula (VIII) with bis(pinacolato) diboron (available from Aldrich), in the presence of palladium catalyst, such as tris(dibenzylideneacetone) dipalladium (available from Aldrich), and in the presence of a phosphine ligand, such as 2-dicyclohexylphosphino-2',4', 6'-triisopropylbiphenyl (X-PHOS) (available from Aldrich), and in the presence of potassium acetate, in an inert solvent, such as 1,4-dioxane, at elevated temperature, for example 110° C., and in an inert atmosphere, such as nitrogen. Addition of water to the reaction mixture at the end of the reaction causes hydrolysis of the resulting pinacolato ester to provide the required boronic acid (V).

(3-(1H-Pyrazol-1-yl)phenyl)boronic acid, i.e. compound (V), where R$_1$, R$_2$ and R$_3$ each represents hydrogen, is commercially available, for example from ABCR GmbH.

Compounds of structural formula (VIII) may be prepared from (3-bromophenyl)hydrazine (available from Aldrich), or (3-bromophenyl)hydrazine hydrochloride (available from Amatek or Reddy & Reddy) and heating with an appropriate dicarbonyl compound, such as pentane-2,4-dione, heptane-3,5-dione, 3-fluoro-pentane-2,4-dione, or a masked dione, such as (E)-4-(dimethylamino)but-3-en-2-one, or an acetylenic ketone, such as hex-3-yn-2-one, by the methods described herein in the experimental section.

It will be appreciated that in any of the routes described above it may be advantageous to protect one or more functional groups. Examples of protecting groups and the means for their removal can be found in T. W. Greene 'Protective Groups in Organic Synthesis' (3rd edition, J. Wiley and Sons, 1999). Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—COCF$_3$) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain compounds of formulae (V) to (VIII) are also believed to be novel and therefore form a yet further aspect of the invention.

The absolute configuration of compound (I) where R$_1$ represents a methyl group, R$_2$ represents a hydrogen atom and R$_3$ represents a methyl group (Example 1) was obtained following an independent enantioselective asymmetric synthesis providing a common intermediate of known absolute configuration, and comparison of the spectroscopic, optical rotation and analytical chiral HPLC of the common intermediate derived from both synthetic routes. The common intermediate was obtained by reduction of the carboxylic acid group of Example 1 with lithium aluminium hydride to give the alcohol Intermediate 33 Isomer 1 (Scheme 3). The other diastereoisomer of Intermediate 33 (Isomer 2) was obtained from the minor product of Intermediate 13 (Isomer 2) by lithium aluminium hydride reduction and catalytic hydrogenation of the resulting naphthyridine alcohol over 5% Rh on carbon.

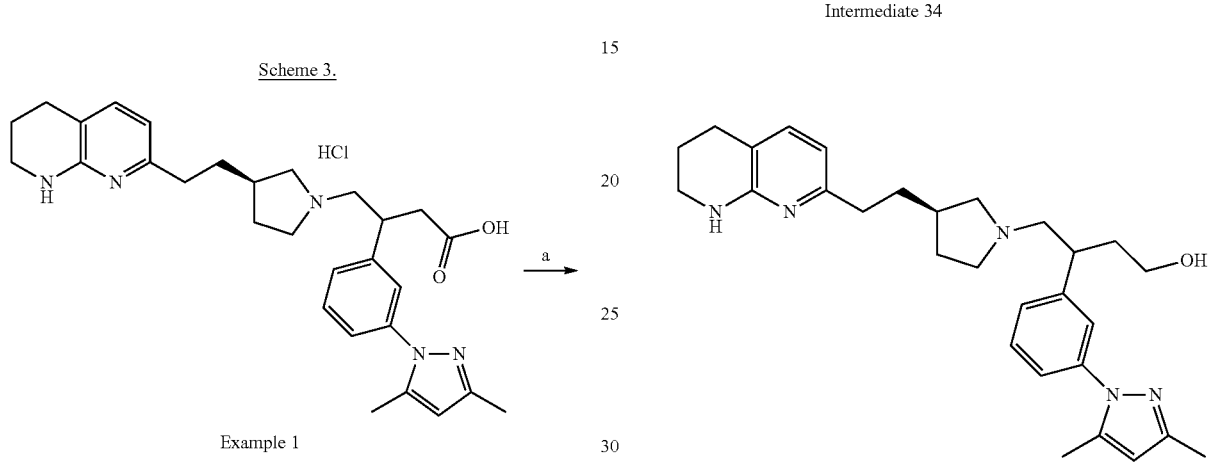

Reagents and Conditions: (a) LiAlH₄, THF;
(b) H₂, 5% Rh/C, EtOH

The independent synthesis commenced by conversion of Intermediate 9 to Intermediate 35 using tert-butyl 2-bromoacetate, palladium diacetate, tri(o-tolyl)phosphine and tripotassium phosphate (Scheme 4). The tert-butyl ester was removed with TFA to give Intermediate 36 which was then esterified with methanol to give Intermediate 37. The latter was alkylated with tert-butyl 2-bromoacetate to give the racemic Intermediate 38. The racemate 38 was resolved to its two enantiomers, Isomer 1 and Isomer 2, by preparative chiral HPLC. Isomer 1 of Intermediate 38 had an optical rotation of +81 in CHCl3, whereas Isomer 2 had an optical rotation of −82. The methyl ester of each enantiomer of Intermediate 38 was selectively hydrolysed using lithium hydroxide and hydrogen peroxide to give Intermediate 39 Isomer 1 and Isomer 2. Isomer 1 had an optical rotation of +42, whereas Isomer 2 had an optical rotation of −41.

15
-continued

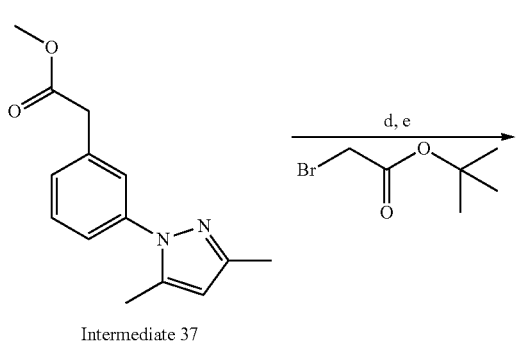

Intermediate 35

Intermediate 36

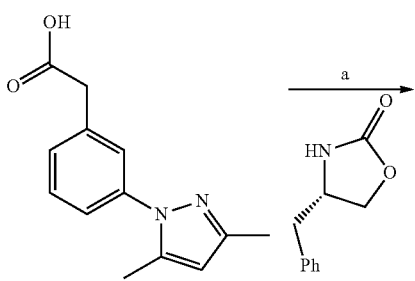

Intermediate 37

16
-continued

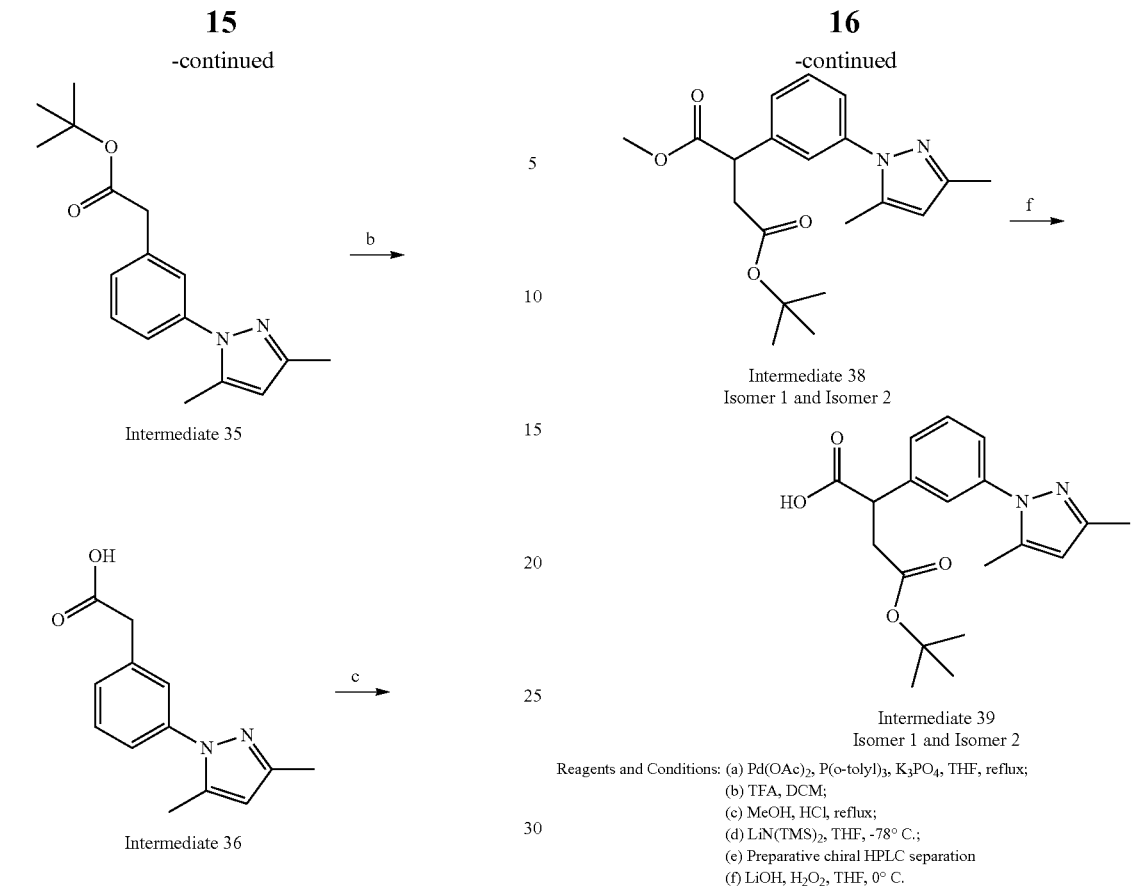

Intermediate 38
Isomer 1 and Isomer 2

Intermediate 39
Isomer 1 and Isomer 2

Reagents and Conditions: (a) Pd(OAc)$_2$, P(o-tolyl)$_3$, K$_3$PO$_4$, THF, reflux;
(b) TFA, DCM;
(c) MeOH, HCl, reflux;
(d) LiN(TMS)$_2$, THF, -78° C.;
(e) Preparative chiral HPLC separation
(f) LiOH, H$_2$O$_2$, THF, 0° C.

The absolute configuration of each of the enantiomers of Intermediate 39 was obtained by independent asymmetric synthesis using Evans methodology. Thus, Intermediate 36 was converted to Intermediate 40 using the commercially available (S)-4-benzyloxazolidin-2-one (Scheme 5). Intermediate 40 was first enolised using lithium hexamethyldisilazide at −78.0 and then alkylated with tert-butyl 2-bromoacetate to give Intermediate 41 (major isomer) as the diastereoisomer derived by alkylation of the enolate from the less hindered side. The minor component was the isomer derived by alkylation of the enolate from the more hindered side (Intermediate 42). Hydrolysis of the major isomer (Intermediate 41) with lithium hydroxide and hydrogen peroxide gave the expected (S)-enantiomer of Intermediate 39 which had an optical rotation of +65. Therefore, Intermediate 39 Isomer 1 has the (S)-configuration.

Scheme 5.

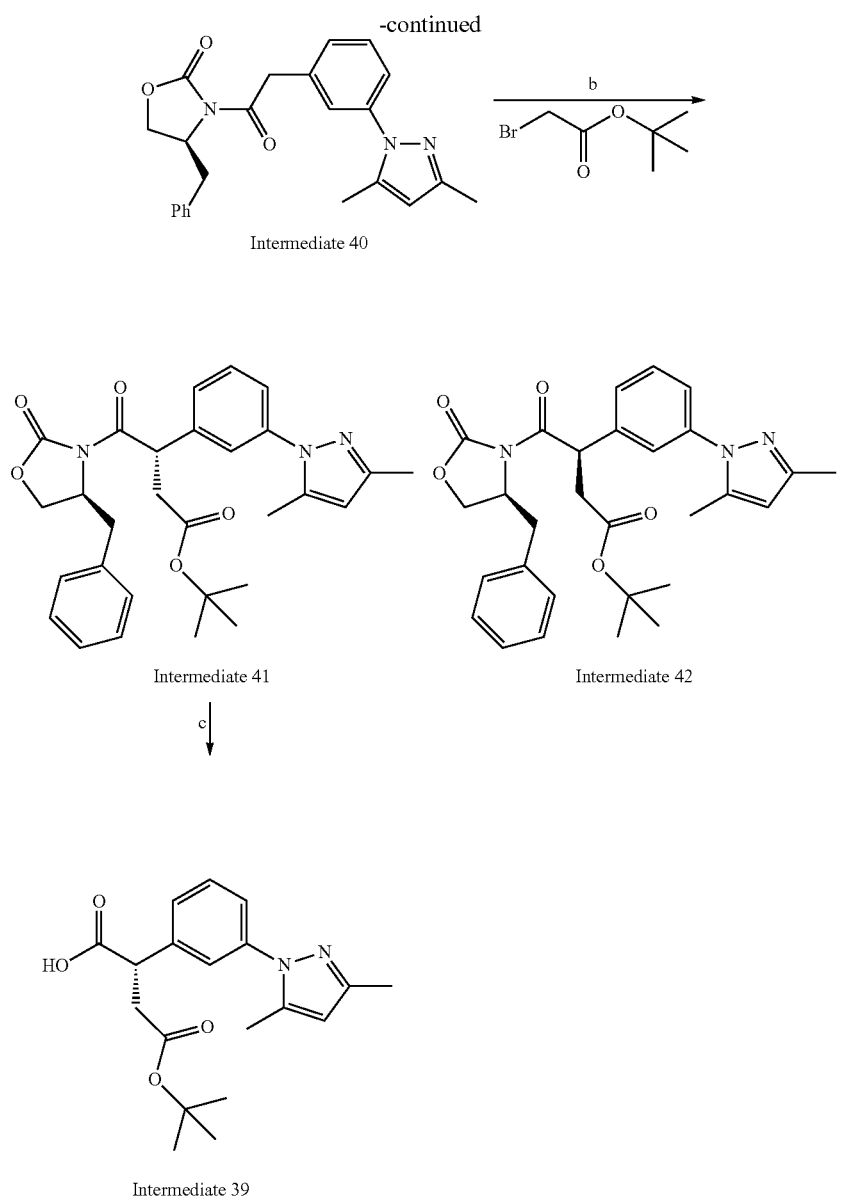

Reagents and Conditions: (a) pivaloyl chloride, DIPEA, THF, -78° C.;
(b) LiN(TMS)₂, THF, -78° C.;
(c) LiOH, H₂O₂, THF, 0° C.

Intermediate 3 was then acylated with the (S)-enantiomer of Intermediate 39 (Isomer 1) in the presence of EDC, N-hydroxybenztriazole and N-methyl morpholine to give Intermediate 43, which was converted to Intermediate 44 by catalytic hydrogenation over 5% Rh/C (Scheme 6). The tert-butyl ester of 44 was cleaved with TFA to give Intermediate 45, which was reduced first by borane-THF complex and then by lithium aluminium hydride to give Intermediate 46. The 600 MHz ¹H NMR spectrum, the optical rotation and analytical chiral HPLC of the major component of Intermediate 46 was identical with the data generated for Intermediate 33 Isomer 1. Therefore the configuration of the benzylic asymmetric centre of Intermediate 33 Isomer 1 has the (S)-configuration.

Scheme 6.

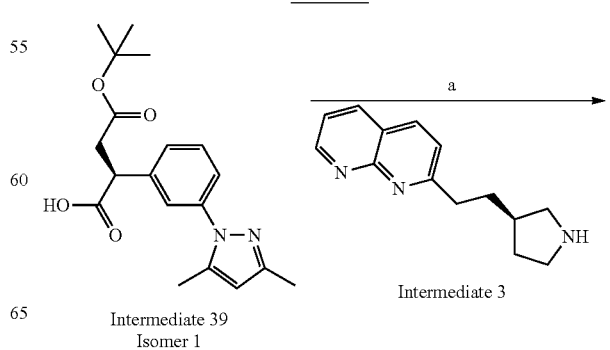

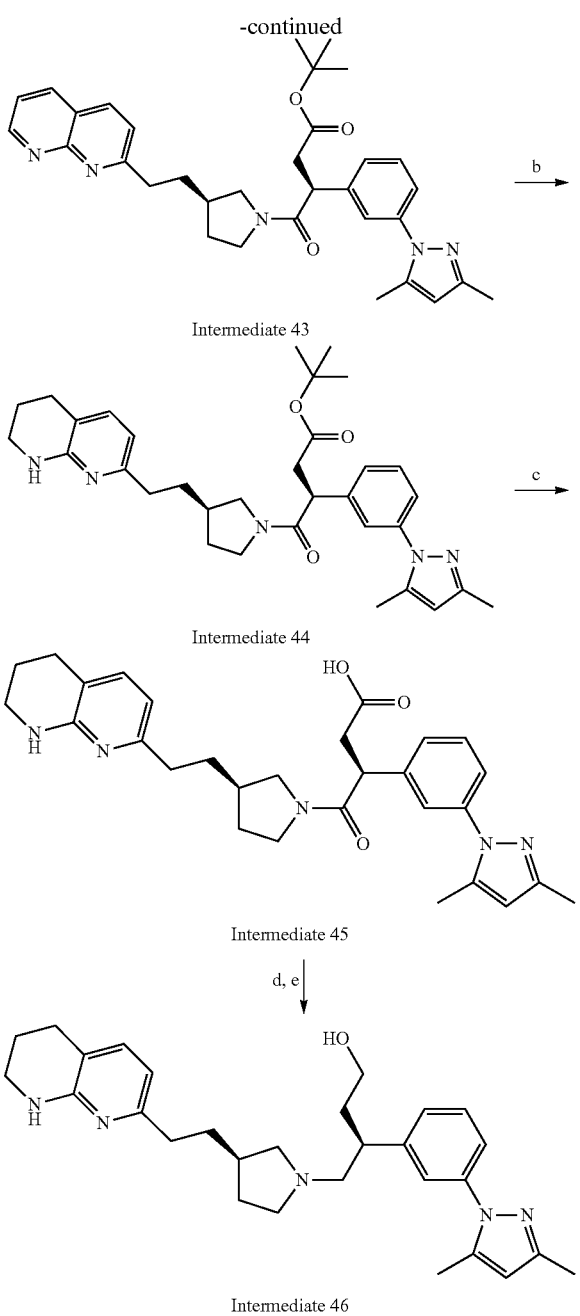

Reagents and Conditions: (a) EDC, HOBT, NMM, DCM;
(b) H$_2$, 5% Rh/C, EtOH;
(c) TFA, DCM;
(d) BH$_3$·THF;
(e) LiAlH$_4$, THF, 60° C.

Methods of Use

The compounds of formula (I) and salts thereof are believed to be inhibitors of integrin receptor activity, particularly α$_v$β$_6$ receptor activity, and thus have potential utility in the treatment of diseases or conditions for which an α$_v$β$_6$ compound is indicated.

The present invention thus provides a compound of formula (I) or a pharmaceutically acceptable salt thereof for use in therapy. The compound of formula (I) or pharmaceutically acceptable salt thereof can be for use in the treatment of a disease or condition for which an α$_v$β$_6$ receptor antagonist is indicated.

The present invention thus provides a compound of formula (I) or a pharmaceutically acceptable salt thereof for use in the treatment of a disease or condition for which an α$_v$β$_6$ receptor antagonist is indicated.

Also provided is the use of a compound of formula (I) or a pharmaceutically acceptable salt thereof in the manufacture of a medicament for the treatment of a disease or condition for which an α$_v$β$_6$ receptor antagonist is indicated.

Also provided is a method of treating a disease or conditions for which an α$_v$β$_6$ receptor antagonist is indicated in a subject in need thereof which comprises administering a therapeutically effective amount of compound of formula (I) or a pharmaceutically acceptable salt thereof.

Suitably the subject in need thereof is a mammal, particularly a human.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Fibrotic diseases involve the formation of excess fibrous connective tissue in an organ or tissue in a reparative or reactive process. α$_v$β$_6$ antagonists are believed to be useful in the treatment of a variety of such diseases or conditions including those dependent on α$_v$β$_6$ integrin function and on activation of transforming growth factor beta via alpha v integrins. Diseases may include but are not limited to pulmonary fibrosis e.g. idiopathic pulmonary fibrosis, non-specific interstitial pneumonia (NSIP), usual interstitial pneumonia (UIP), Hermansky-Pudlak syndrome, progressive massive fibrosis (a complication of coal workers' pneumoconiosis), connective tissue disease-related pulmonary fibrosis, airway fibrosis in asthma and COPD, acute respiratory distress syndrome (ARDS) associated fibrosis, acute lung injury; radiation-induced fibrosis; familial pulmonary fibrosis; pulmonary hypertension); renal fibrosis (diabetic nephropathy, IgA nephropathy, lupus nephritis; focal segmental glomerulosclerosis (FSGS), transplant nephropathy, autoimmune nephropathy, drug-induced nephropathy, hypertension-related nephropathy, nephrogenic systemic fibrosis); liver fibrosis (viral-induced fibrosis (e.g. hepatitis C or B), autoimmune hepatitis, primary biliary cirrhosis, alcoholic liver disease, non-alcoholic fatty liver disease including non-alcoholic steatohepatitis (NASH), congenital hepatic fibrosis, primary sclerosing cholangitis, drug-induced hepatitis, hepatic cirrhosis); skin fibrosis (hypertrophic scars, scleroderma, keloids, dermatomyositis, eosinophilic fasciitis, Dupytrens contracture, Ehlers-Danlos syndrome, Peyronie's disease epidermolysis bullosa dystrophica, oral submucous fibrosis); ocular fibrosis (AMD, diabetic macular oedema, dry eye, glaucoma); cardiac fibrosis (congestive heart failure, endomyocardial fibrosis, hypertrophic cardiomyopathy (HCM), dilated cardiomyopathy (DCM), arrhythmogenic right ventricular cardiomyopathy (ARVC), hypertensive heart disease, cardiac sarcoidosis and other forms of heart failure) and other miscellaneous fibrotic conditions (mediastinal fibrosis, myelofibrosis, retroperitoneal fibrosis, Crohn's disease, neurofibromatosis, uterine leiomyomas (fibroids), chronic organ transplant rejection). There may be additional benefits for additional antagonism of $\alpha_v\beta_5$, or $\alpha_v\beta_8$.

In addition, pre-cancerous lesions or cancers associated with $\alpha_v\beta_6$ integrins may also be treated (these may include but are not limited to endometrial, basal cell, liver, colon, cervical, oral, pancreas, breast and ovarian cancers, Kaposi's sarcoma, Giant cell tumours and cancer associated stroma). Conditions that may derive benefit from effects on angiogenesis may also benefit (e.g. solid tumours).

The term "disease or condition for which an $\alpha_v\beta_6$ inhibitor is indicated", is intended to include any or all of the above disease states.

In one embodiment the disease or condition for which an $\alpha_v\beta_6$ inhibitor is indicated is selected from idiopathic pulmonary fibrosis.

Compositions

While it is possible that for use in therapy, a compound of formula (I) as well as pharmaceutically acceptable salts thereof may be administered as the raw chemical, it is common to present the active ingredient as a pharmaceutical composition.

The present invention therefore provides in a further aspect a pharmaceutical composition comprising a compound of formula (I) or a pharmaceutically acceptable salt and one or more pharmaceutically acceptable carriers, diluents and/or excipients. The compounds of the formula (I) and pharmaceutically acceptable salts, are as described above. The carrier(s), diluent(s) or excipient(s) must be acceptable in the sense of being compatible with the other ingredients of the composition and not deleterious to the recipient thereof.

In accordance with another aspect of the invention there is also provided a process for the preparation of a pharmaceutical composition including admixing a compound of the formula (I), or a pharmaceutically acceptable salt thereof, with one or more pharmaceutically acceptable carriers, diluents or excipients. The pharmaceutical composition may be for use in the treatment of any of the conditions described herein.

Further provided is a pharmaceutical composition for the treatment of diseases or conditions for which an $\alpha_v\beta_6$ receptor inhibitor is indicated comprising a compound of formula (I) or a pharmaceutically acceptable salt thereof.

Further provided is a pharmaceutical composition comprising 0.05 to 1000 mg of a compound of formula (I) or a pharmaceutical salt thereof and 0.1 to 2 g of one or more pharmaceutically acceptable carriers, diluents or excipients.

Since the compounds of formula (I) are intended for use in pharmaceutical compositions it will be readily understood that they are each preferably provided in substantially pure form, for example, at least 60% pure, more suitably at least 75% pure and preferably at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment the pharmaceutical composition is adapted for nasal or inhaled administration.

Dosage forms for nasal or inhaled administration may conveniently be formulated as aerosols, solutions, suspensions, gels or dry powders.

For compositions suitable and/or adapted for inhaled administration, it is preferred that the compound of the invention is in a particle-size-reduced form, and more preferably the size-reduced form is obtained or obtainable by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or salt thereof (preferably in particle-size-reduced form, e.g. in micronised form), and optionally a performance modifier such as L-leucine or another amino acid and/or metals salts of stearic acid such as magnesium or calcium stearate. Preferably, the dry powder inhalable composition comprises a dry powder blend of lactose and the compound of formula (I) or salt thereof. The lactose is preferably lactose hydrate e.g. lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g. 10-1000 microns e.g.

30-1000 microns) in diameter, and/or 50% or more of the lactose particles being less than 500 microns (e.g. 10-500 microns) in diameter. More preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. Most importantly, it is preferable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition can be administered by inhalation via the device such as the DISKUS™ device, marketed by GlaxoSmithKline. The DISKUS™ inhalation device is for example described in GB 2242134 A, and in such a device at least one container for the pharmaceutical composition in powder form (the container or containers preferably being a plurality of sealed dose containers mounted longitudinally in a strip or ribbon) is defined between two members peelably secured to one another; the device comprises: a means of defining an opening station for the said container or containers; a means for peeling the members apart at the opening station to open the container; and an outlet, communicating with the opened container, through which a user can inhale the pharmaceutical composition in powder form from the opened container.

The compounds of the invention thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser.

Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

Compositions for inhaled or intranasal administration may also be administered to the lung and other regions of the respiratory tract by nebulisation. Such compositions may be aqueous solutions or suspensions. Solutions for inhalation by nebulisation may be formulated with the addition of agents such as acid or alkali, buffer salts, isotonicity adjusting agents, surfactants or antimicrobials, such as benzylalkonium chloride (BAC). The composition may be sterile and free of antimicrobial preservative. They may be sterilised, for example, by filtration or heating in an autoclave. They may be presented as a non-sterile solution. A single unit dose of a therapeutically effective amount of the compound of the present invention may be provided as a pre-mixed, premeasured formulation, in a single container.

In another embodiment the pharmaceutical composition is adapted for oral administration.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, as, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilising agent such as agaragar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like.

Lubricants used in these dosage forms include sodium oleate, sodium stearate, magnesium stearate, sodium benzoate, sodium acetate, sodium chloride and the like.

Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavoured aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavour additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release as for example by coating or embedding particulate material in polymers, wax or the like.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions for subcutaneous, intravenous or intramuscular administration which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

A therapeutically effective amount of a compound of the present invention will depend upon a number of factors including, for example, the age and weight of the subject, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 to 3000 mg, more preferably 0.5 to 1000 mg, of a compound of the invention calculated as the free base.

Each dosage unit for nasal or inhaled administration preferably contains from 0.001 to 50 mg, more preferably 0.01 to 50 mg, yet more preferably 1 to 50 mg, of a compound of the formula (I) or a pharmaceutically acceptable salt thereof, calculated as the free base.

For administration of a nebulised solution or suspension, a dosage unit typically contains from 1 to 15 mg, for example, from 2 mg to 10 mg, or from 4 mg to 6 mg, which may suitably be delivered once daily, twice daily or more than twice daily. The compound of the present invention may be provided in a dry or lyophilised powder for reconstitution in the pharmacy or by the patient, or may, for example, be provided in an aqueous saline solution.

The pharmaceutically acceptable compounds the invention can be administered in a daily dose (for an adult patient) of, for example, an oral or parenteral dose of 0.01 mg to 3000 mg per day or 0.5 to 1000 mg per day, or a nasal or inhaled dose of 0.001 to 50 mg per day or 0.01 to 50 mg per day, or 10 to 50 mg, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of the invention and may be employed alone or in combination with other therapeutic agents. Combination therapies according to the present invention thus comprise the administration of at least one compound of formula (I) or a pharmaceutically acceptable salt thereof, and the use of at least one other pharmaceutically active agent. Preferably, combination therapies according to the present invention comprise the administration of at least one compound of formula (I) or a pharmaceutically acceptable salt thereof, and at least one other pharmaceutically active agent. The compound(s) of the invention and the other pharmaceutically active agent(s) may be administered together in a single pharmaceutical composition or separately and, when administered separately this may occur simultaneously or sequentially in any order. The amounts of the compound(s) of the invention and the other pharmaceutically active agent(s) and the relative timings of administration will be selected in order to achieve the desired combined therapeutic effect.

Thus in a further aspect, there is provided a combination comprising a compound of the invention and at least one other pharmaceutically active agent.

Thus in one aspect, the compound and pharmaceutical compositions according to the invention may be used in combination with or include one or more other therapeutic agents. It will be appreciated that when the compound of the present invention is administered in combination with one or more other therapeutically active agents normally administered by the inhaled, intravenous, oral, intranasal or other route, that the resultant pharmaceutical composition may be administered by the same route. Alternatively, the individual components of the composition may be administered by different routes.

The compounds of formula (I) and pharmaceutically acceptable salts thereof may be used in combination with one or more other agents which may be useful in the prevention or treatment of allergic disease, inflammatory disease, autoimmune disease, for example; antigen immunotherapy, anti-histamines, corticosteroids (eg fluticasone propionate, fluticasone furoate, beclomethasone dipropionate, budesonide, ciclesonide, mometasone furoate, triamcinolone, flunisolide), NSAIDs, leukotriene modulators (e.g. montelukast, zafirlukast, pranlukast) iNOS inhibitors, tryptase inhibitors, IKK2 inhibitors, p38 inhibitors, Syk inhibitors, elastase inhibitors, beta-2 integrin antagonists, adenosine ata agonists, chemokine antagonists such as CCR3 antagonists or CCR4 antagonists, mediator release inhibitors such as sodium chromoglycate, 5-lipoxygenase inhibitors (zyflo), DP1 antagonists, DP2 antagonists, pI3K delta inhibitors, ITK inhibitors, LP (lysophosphatidic) inhibitors or FLAP (5-lipoxygenase activating protein) inhibitors (e.g. sodium 3-(3-(tert-butylthio)-1-(4-(6-ethoxy-pyridin-3-yl)benzyl)-5-((5-methylpyridin-2-yl)methoxy)-1H-indol-2-yl)-2,2-dimethylpropanoate), methotrexate, and similar agents; monoclonal antibody therapy such as anti-IgE, anti-TNF, anti-IL-5, anti-IL-6, anti-IL-12, anti-IL-1 and similar agents; receptor therapies e.g. etanercept and similar agents; antigen non-specific immunotherapies (e.g. interferon or other cytokines/chemokines, cytokine/chemokine receptor modulators, cytokine agonists or antagonists, TLR agonists and similar agents)), inhibitors of TGFβ.synthesis, for example Pirfenidone, tyrosine kinase inhibitors targeting the vascular endothelial growth factor (VEGF), platelet-derived growth factor (PDGF) and fibroblast growth factor (FGF) receptor kinases, for example Intedanib (BIBF-1120) and Imatinib mesylate (Gleevec), endothelin receptor antagonists, for example Ambrisentan or Macitentan, anti-oxidants, such as N-Acetylcysteine (NAC or Fluimucil), broad-spectrum antibiotics, such as tetracyclines, for example Minocycline hydrochloride, phosphodiesterase 5 (PDE5) inhibitors for example sildenafil. Alternatively anti $α_vβ_6$ antibodies e.g. monoclonal antibodies such as those described in WO2003100033A2 may be used in combination.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

ABBREVIATIONS

The following list provides definitions of certain abbreviations as used herein. It will be appreciated that the list is not exhaustive, but the meaning of those abbreviations not herein below defined will be readily apparent to those skilled in the art.

Ac (acetyl)
BCECF-AM (2',7'-bis-(2-carboxyethyl)-5-(and -6)-carboxy-fluorescein AM Ester)
Bu (butyl)
CHAPS (3-[(3-Cholamidopropyl)dimethylammonio]-1-propanesulfonate)
CV (column volume)
DCM (dichloromethane)
DMF (N,N-dimethylformamide)
DMSO (dimethylsulfoxide)
DSC (differential scanning colorimetry)
Et (ethyl)
EtOH (ethanol)
EtOAc (ethyl acetate)
h (hour/hours)
HCl (Hydrochloric acid)
HEPES (4-(2-hydroxyethyl)-1-piperazineethanesulfonic acid)
L (liters)
M (molar)
MDAP (mass directed auto-preparative HPLC)
Me (methyl)
MeOH (methanol)
min (minute/minutes)
MTBE (methyl t-butyl ether)
Ph (phenyl)
$^iPr$ (isopropyl)
(R)-BINAP (R)-(+)-2,2'-Bis(diphenylphosphino)-1,1'-binaphthalene
Si (Silica)
SPE (solid phase extraction)
TEA (triethylamine)
TFA (trifluoroacetic acid)
THF (tetrahydrofuran)
TLC (thin layer chromatography)
XRPD (X-ray powder diffraction)

All references to brine refer to a saturated aqueous solution of sodium chloride.

EXPERIMENTAL DETAILS

Analytical LCMS

Analytical LCMS was conducted on one of the following systems A, B or C.

The UV detection to all systems was an averaged signal from wavelength of 220 nm to 350 nm and mass spectra were recorded on a mass spectrometer using alternate-scan positive and negative mode electrospray ionization.

Experimental details of LCMS systems A-B as referred to herein are as follows:

System A
Column: 50 mm×2.1 mm ID, 1.7 µm Acquity UPLC BEH $C_{18}$ column
Flow Rate: 1 mL/min.
Temp.: 40° C.
Solvents: A: 10 mM ammonium bicarbonate in water adjusted to pH10 with ammonia solution
B: Acetonitrile

| Gradient: | | |
|---|---|---|
| Time (min) | A % | B % |
| 0 | 99 | 1 |
| 1.5 | 3 | 97 |
| 1.9 | 3 | 97 |
| 2.0 | 0 | 100 |

System B
Column: 50 mm×2.1 mm ID, 1.7 µm Acquity UPLC BEH $C_{18}$
Flow Rate: 1 mL/min.
Temp.: 40° C.
Solvents: A: 0.1% v/v solution of trifluoroacetic acid in water
B: 0.1% v/v solution of trifluoroacetic acid in acetonitrile

| Gradient: | | |
|---|---|---|
| Time (min) | A % | B % |
| 0 | 97 | 3 |
| 1.5 | 0 | 100 |
| 1.9 | 0 | 100 |
| 2.0 | 97 | 3 |

System C
Column: 50 mm×2.1 mm ID, 1.7 µm Acquity UPLC BEH C18 column
Flow Rate: 1 mL/min
Temp.: 40° C.
Solvents: A: 0.1% v/v solution of formic acid in water
B: 0.1% v/v solution of formic acid in acetonitrile

| Gradient: | | |
|---|---|---|
| Time (min) | A % | B % |
| 0 | 97 | 3 |
| 1.5 | 0 | 100 |
| 1.9 | 0 | 100 |
| 2.0 | 97 | 3 |

Mass Directed Auto-Preparative HPLC

Crude products were purified by MDAP HPLC by one of the following methods A-C. The run time was 15 min unless otherwise stated. The UV detection for all methods was an averaged signal from wavelength of 210 nm to 350 nm and mass spectra were recorded on a mass spectrometer using alternate-scan positive and negative mode electrospray ionization.

Method A:
Method A was conducted on an XBridge $C_{18}$ column (typically 100 mm×30 mm i.d. 5 µm packing diameter) at ambient temperature. The solvents employed were:
A=10 mM aqueous ammonium bicarbonate adjusted to pH 10 with ammonia solution.
B=acetonitrile.
The gradient employed was:

| Time (min) | Flow Rate (mL/min) | % A | % B |
|---|---|---|---|
| 0 | 40 | 85 | 15 |
| 1 | 40 | 85 | 15 |
| 10 | 40 | 45 | 55 |
| 11 | 40 | 1 | 99 |
| 15 | 40 | 1 | 99 |

Method B:
Method A was conducted on an X Bridge $C_{18}$ column (typically 100 mm×30 mm i.d. 5 µm packing diameter) at ambient temperature. The solvents employed were:
A=10 mM aqueous ammonium bicarbonate adjusted to pH 10 with ammonia solution.
B=acetonitrile.
The gradient employed was:

| Time (min) | Flow Rate (mL/min) | % A | % B |
|---|---|---|---|
| 0 | 40 | 85 | 15 |
| 1 | 40 | 85 | 15 |
| 20 | 40 | 45 | 55 |
| 21 | 40 | 1 | 99 |
| 25 | 40 | 1 | 99 |

Method C:
Method C was conducted on an XBridge $C_{18}$ column (typically 150 mm×30 mm i.d. 5 µm packing diameter) at ambient temperature.
The solvents employed were:
A=0.1% v/v solution of Formic Acid in water.
B=0.1% v/v solution of Formic Acid in Acetonitrile.
The gradient employed was:

| Time (min) | Flow Rate (mL/min) | % A | % B |
|---|---|---|---|
| 0 | 40 | 50 | 50 |
| 1 | 40 | 50 | 50 |
| 10 | 40 | 1 | 99 |
| 10.5 | 40 | 1 | 99 |
| 15 | 40 | 1 | 99 |

The UV detection was an averaged signal from wavelength of 210 nm to 350 nm.

Preparation of Intermediates

Intermediate 1: (R)-tert-butyl 3-(iodomethyl)pyrrolidine-1-carboxylate

A 5 L vacuum-jacketed glass reaction vessel (Radley's LARA) was charged with DCM (2 L), followed by triphenylphosphine (339 g, 1.29 mol) and imidazole (88 g, 1.29 mol), and the temperature was reduced to 0° C. Iodine (328 g, 1.29 mol) was then added portionwise over 30 min whilst maintaining the reaction temperature at between 0-5° C. to control the exotherm. During the addition, a thick brown precipitate formed. The precipitate was allowed to warm to room temperature over 15 min and was then stirred at room temperature for a further 30 min. A solution of (R)-tert-butyl 3-(hydroxymethyl pyrrolidine-1-carboxylate (200 g, 994 mmol) (available from Fluorochem or BePharm Ltd) in DCM (200 mL) was added portionwise over 15 min, whilst maintaining the reaction temperature between 24-30° C. The reaction mixture was stirred for 2 h, then diluted with TBME (8 L), and filtered. The filtrate was concentrated under reduced pressure, and the residue (700 g) was triturated in diethyl ether (2 L) in an ice water bath to give 333 g of crude product. A 27 g portion of the crude product was purified by chromatography on a silica cartridge (100 g) eluting with a gradient of 0-50% ethyl acetate cyclohexane over 30 min. The appropriate fractions were combined and evaporated in vacuo to give the title compound (16.33 g, 5%) as a yellow oil. The remaining crude material (~306 g) was purified by chromatography on a silica cartridge (1.5 kg) eluting with a gradient of 0-30% ethyl acetate-cyclohexane over 9.5 column volumes. The appropriate fractions were combined and evaporated in vacuo to give the title compound (233.94 g, 76%) as a pale yellow oil: LCMS (System A) RT=1.19 min, 100%, ES+ve m/z 312 (M+H)+; $[\alpha]_D^{20}$=+23 (c 1.00 in EtOH).

Intermediate 2: (R)-tert-Butyl 3-(2-(1,8-naphthyridin-2-yl)ethyl)pyrrolidine-1-carboxylate A stirred solution of 2-methyl-1,8-naphthyridine (57.5 g, 399 mmol) (available from Manchester Organics) and (R)-tert-butyl 3-(iodomethyl)pyrrolidine-1-carboxylate (124.2 g, 399 mmol) (Intermediate 1) in THF (1 L) was cooled to 0° C. and treated under nitrogen with a solution of lithium bis(trimethylsilyl)amide in THF (1M, 399 mL, 399 mmol) over 20 min and the reaction mixture was stirred at 0° C. for 3 h. The reaction was quenched with saturated ammonium chloride solution (500 mL) and water (500 mL) and ethyl acetate (1 L) was added. The layers were separated and the aqueous phase was extracted with further ethyl acetate (1 L). The combined organic layers were dried (MgSO$_4$), filtered and evaporated in vacuo. The residual brown oil (162 g) was purified by chromatography on a silica cartridge (750 g) eluting with a gradient of 0-100% [ethyl acetate in (5% MeOH 95% ethyl acetate)] over 8 column volumes. The appropriate fractions were combined and evaporated in vacuo to give the title compound (46.65 g, 36%) as an orange solid: LCMS (System A) RT=0.99 min, 97%, ES+ve m/z 328 (M+H)+, $[\alpha]_D^{20}$=+22 (c 1.00 in EtOH).

Intermediate 3: (R)-2-(2-(Pyrrolidin-3-yl)ethyl)-1,8-naphthyridine, dihydrochloride salt A solution of (R)-tert-butyl 3-(2-(1,8-naphthyridin-2-yl) ethyl)3lyrrolidone-1-carboxylate (104.71 g, 320 mmol) in DCM (500 mL) was treated slowly with HCl (4M in 1,4-dioxane (200 mL, 800 mmol) at room temperature. The mixture was stirred overnight at room temperature, by which time a large solid clump had formed in the flask. MeOH (~100 mL) was added to help dissolve the solid and stirring continued. The LCMS indicated ~72% product and ~25% starting material. Additional quantity of 4M HCl in 1,4-dioxane (100 mL) was added and stirring was continued for 1 h. The solvent was evaporated in vacuo to give the title compound (89.66 g, 93%) as a purple coloured solid: LCMS (System B) RT=0.34 min, 100%, ES+ve m/z 228 (M+H)+.

Intermediate 4: (E)-tert-Butyl 4-bromobut-2-enoate

Isobutylene gas (363 mL, 3.82 mol) was bubbled through a stirred solution of (E)-4-bromobut-2-enoic acid (210 g, 1.27 mmol) [T. Den Hartog, D. J. Van Dijken, A. J. Minnaard, B. L. Feringa *Tetrahedron Asymmet*. 2010, 21, 1574-1584] and concentrated H$_2$SO$_4$ (20.35 mL, 382 mmol) in diethyl ether (1 L) at −40° C. for 30 min in a steal autoclave. The mixture was sealed in the autoclave and the mixture was stirred at room temperature for 24 h. The reaction was cooled to 0° C. then basified with triethylamine (250 mL) and extracted with DCM (3×200 mL). The organic layer was dried and concentrated in vacuo. The residue was triturated in n-pentane (200 mL) to give the title compound (140 g, 50%) as brown syrup: $^1$H NMR δ (CDCl$_3$, 400 MHz) 6.89 (dt, J=15, 7.5 Hz, 1H), 5.95 (dt, J=15, 1 Hz, 1H), 3.99 (dd, J=7.5, 1 Hz, 2H), 1.48 (s, 9H). The aqueous layer was acidified with 2M HCl to pH 2, and extracted with EtOAc (2×250 mL), the combined organic layers were washed with water (2×500 mL), dried over Na$_2$SO$_4$, evaporated in vacuo to afford unreacted starting material (50 g) as an off-white solid.

Intermediate 5: (E)-tert-Butyl 4-acetoxybut-2-enoate

A stirred solution of (E)-tert-butyl 4-bromobut-2-enoate (280 g, 1.27 mol) in acetonitrile (1.2 L) was treated with potassium acetate (186 g, 1.9 mol) at room temperature. The mixture was stirred at 60° C. for 4 h and the reaction was monitored by TLC (10% diethyl ether in petroleum ether, R$_f$=0.4, detection by UV). The reaction mixture was cooled to room temperature, the solid was removed by filtration and washed with diethyl ether (600 mL). The filtrate was concentrated under reduced pressure, and the residue was purified by flash column chromatography on silica gel eluting with 10% diethyl ether in petroleum ether. Appropriate fractions were combined and evaporated to give the title compound (148 g, 58% yield) as a pale yellow liquid: $^1$H NMR δ (CDCl$_3$, 400 MHz) 6.82 (dt, J=15.5, 5 Hz, 1H), 5.94 (dt, J=15.5, 2 Hz, 1H), 4.71 (dd, J=5, 2 Hz, 2H), 2.11 (s, 3H), 1.49 (s, 9H).

Intermediate 6: 1-(3-Bromophenyl)-5-methyl-1H-pyrazole

A solution of (3-bromophenyl)hydrazine hydrochloride (available from Amatek) (300 g, 1.34 mol) in acetic acid (2.2 L) was treated with diisopropylethylamine (234 mL, 1.34 mol), followed by (E)-4-(dimethylamino) but-3-en-2-one (available from Acros) (152 g, 1.34 mol), and the reaction mixture was heated at 90° C. for 2 h. The reaction mixture was concentrated under reduced pressure, the residue was poured into saturated NaHCO$_3$ solution, and extracted with ethyl acetate (2×1 L). The organic phase was separated and dried over Na$_2$SO$_4$. The filtrate was evaporated in vacuo and the residue was purified by flash silica gel (100-200 mesh) column chromatography using 0-4.5% ethyl acetate in petroleum ether. Appropriate fractions were collected and concentrated under reduced pressure to afford 1-(3-bromophenyl)-3-methylpyrazole (Intermediate 29) (40 g, 13%). Further elution of the column with 20-40% ethyl acetate in petroleum ether gave the title compound (205 g, 64%) as a yellow liquid: $^1$H NMR δ (CDCl$_3$; 600 MHz) 7.67 (t, 1=1.9 Hz, 1H), 7.59 (d, J=1.5 Hz, 1H), 7.54-7.49 (m, 1H), 7.43-7.40 (m, 1H), 7.37-7.32 (m, 1H), 6.21 (d, J=0.7 Hz, 1H), 2.38 (s, 3H).

Intermediate 7: (3-(5-Methyl-1H-pyrazol-1-yl)-phenyl)boronic acid

A solution of 1-(3-bromophenyl)-5-methylpyrazole (intermediate 6) (200 g, 844 mmol) in THF (2 L) was treated with triisopropyl borate (available from Avra) (294 mL, 1.265 mol) slowly, then cooled to −78° C. and n-BuLi (844 mL, 2109 mmol) was added over 30 min at −78° C. The mixture was stirred at −78° C. for 2 h. Reaction was monitored by TLC (Mobile phase: 30% EtOAc in petroleum ether). The reaction mixture was poured into 2M HCl and the THF was removed under reduced pressure. The residue was basified with 2M NaOH and extracted with ethyl acetate (2×700 mL). The aqueous layer was neutralised (pH-7) with 2M HCl and extracted with ethyl acetate (2×1 L). The organic layers were combined, dried over anhydrous $Na_2SO_4$ and evaporated in vacuo to afford the title compound (120 g, 69%) as a white solid. MS ES+ve m/z 203 $(M+H)^+$.

Intermediate 8:
1-(3-Bromophenyl)-3,5-dimethyl-1H-pyrazole

A solution of (3-bromophenyl)hydrazine hydrochloride (available from Reddy & Reddy) (45 g, 200 mmol) and pentane-2,4-dione (Aldrich) (30.2 g, 302 mmol) in DCM (225 mL) was treated dropwise with conc. $H_2SO_4$ (1.073 mL, 20.13 mmol) and stirred under nitrogen at room temperature for 16 h. The reaction mixture was diluted with DCM (500 mL), and washed with water (2×250 mL). The organic layer was dried over $Na_2SO_4$ and concentrated under reduced pressure. The residue was purified by column chromatography on silica gel (100-200 mesh) eluting with 5% ethyl acetate in hexanes to give the title compound (30 g, 59%) as a light brown liquid: $^1$H NMR δ ($CDCl_3$, 400 MHz) 7.71 (t, J=2 Hz, 1H), 7.57-7.49 (m, 2H), 7.46-7.40 (t, J=8 Hz, 1H), 6.07 (s, 1H), 2.31 (s, 3H), 2.18 (s, 3H).

Intermediate 9:
(3-(3,5-Dimethyl-1H-pyrazol-1-yl)phenyl)boronic acid

A solution of 1-(3-bromophenyl)-3,5-dimethylpyrazole (intermediate 8) (30 g, 119 mmol) in THF (500 mL) was treated with triisopropyl borate (available from Avra) (41.6 mL, 179 mmol), cooled to −78° C., treated dropwise with 2.5 M nBuLi (119 mL, 299 mmol) over 1 h under argon, and stirred for 2 h at −78° C. The reaction mixture was quenched with aqueous HCl solution (2M, 150 mL), neutralised with 2M NaOH solution, and extracted with ethyl acetate (2×300 mL). The combined organic solutions were dried over $Na_2SO_4$ and concentrated under reduced pressure. The residue was triturated with pentane and diethyl ether (1:1) and the solid was collected by filtration to give the title compound (15 g, 57%) as an off-white solid: MS ES+ve m/z 217 $(M+H)^+$.

Intermediate 10:
1-(3-Bromophenyl)-5-ethyl-3-methyl-1H-pyrazole

A suspension of (3-bromophenyl)hydrazine hydrochloride (available from Anichem) (2.0 g, 8.9 mmol) and triethylamine (1.25 mL, 8.9 mmol) in EtOH (20 mL) was stirred briefly until homogeneous and then hex-3-yn-2-one (available from MP Biomedicals or Alfa Aesar) (0.887 g, 8.9 mmol) was added and the mixture was heated to 50° C. for 10 min. The mixture was treated with concentrated HCl (12M, 2.5 mL), heated to 100° C. for 20 min. The mixture was concentrated under reduced pressure, and the residue was partitioned between ethyl acetate and aqueous sodium bicarbonate solution. The organic solution was washed with aqueous $NaHCO_3$, brine, dried ($MgSO_4$) and evaporated under reduced pressure. The residue was purified by chromatography on silica (330 g) cartridge eluting with a gradient of 0-100% DCM cyclohexane over 10 CV. Appropriate fractions were combined and evaporated under reduced pressure to give the title compound (1.95 g, 82%) as an orange oil: $^1$H NMR δ (DMSO-$d_6$, 400 MHz) 7.67 (t, J=2 Hz, 1H), 7.58 (dt, J=8, 2 Hz, 1H), 7.49 (m, 1H), 7.47-7.42 (m, 1H), 6.11 (s, 1H), 2.66 (q, J=7.5 Hz, 2H), 2.19 (s, 3H), 1.13 (t, J=7.5 Hz, 3H).

Intermediate 11: (3-(5-Ethyl-3-methyl-1H-pyrazol-1-yl)phenyl)boronic acid

A mixture of 1-(3-bromophenyl)-5-ethyl-3-methyl-1/1-pyrazole (Intermediate 10) (2.795 g, 10.54 mmol) and triisopropylborate (available from Aldrich) (2.4 g, 12.7 mmol) was treated at −78° C. with n-BuLi (1.6M, 13.2 mL) dropwise and keeping the temp below −60° C. The mixture was allowed to warm to room temperature overnight. The mixture was then quenched with 2M HCl solution (11 mL, to pH 7) and partitioned with ethyl acetate. The organic solution was washed with brine and dried ($MgSO_4$). The filtrate was concentrated under reduced pressure, and the residual oil was triturated with cyclohexane-petroleum ether)(40-60° until a solid was obtained. The solid was collected by filtration, washed with petroleum ether, then with a little water, air-dried, and then dried in vacuo at 60° C. to give the title compound (623 mg, 26%) as a yellow solid: MS ES+ve m/z 231 $(M+H)^+$.

Intermediate 12: (R,E)-tert-Butyl 4-(3-(2-(1,8-naphthyridin-2-yl)ethyl)pyrrolidin-1-yl)but-2-enoate A mixture of (E)-tert-butyl 4-acetoxybut-2-enoate (Intermediate 5) (14.20 g, 70.9 mmol) and 1,1'-bis(diphenylphosphino)ferrocene]dichloropalladium(II) [Pd(dppf)$Cl_2$] (4.72 g, 6.45 mmol) in DCM (100 mL) was stirred for 15 min under nitrogen before a solution of (k)-2-(2-(pyrrolidin-3-yl)ethyl)-1,8-naphthyridine dihydrochloride (Intermediate 3) (17 g, 57 mmol) in diisopropylethylamine (56.3 mL, 322 mmol) and DCM (200 mL) was added. A clear red solution was obtained which was stirred under nitrogen for 24 hours. The mixture was partitioned between DCM and water (3×170 mL). The organic phase was passed through a phase-separator cartridge and the filtrate was concentrated under reduced pressure. The residual oil (27 g) was loaded in DCM to an aminopropyl cartridge (900 g) and purified by chromatography on CombiFlash Companion XL using a gradient of from 0 to 100% ethyl acetate cyclohexane over 10 column volumes. The appropriate fractions were combined and evaporated in vacuo to give the title compound (17.62 g, 85%) as a brown oil, which solidified on standing: LCMS (System A) RT=1.05 min, 100%; ES+ve m/z 368 $(M+H)^+$.

Intermediate 13: tert-Butyl 4-((R)-3-(2-(1,8-naphthyridin-2-yl)ethyl)pyrrolidin-1-yl)-3-(3-(3,5-dimethyl-1H-pyrazol-1-yl)phenyl)butanoate A solution of (3-(3,5-dimethyl-1H-pyrazol-1-yl)phenyl) boronic acid (Intermediate 9) (44.7 g, 207 mmol) in KOH (3.8 M, 54.4 mL, 207 mmol) was treated with a solution of (RE)-tert-butyl 4-(3-(2-(1,8-naphthyridin-2-yl)ethyl)pyrrolidin-1-yl)but-2-enoate (Intermediate 12) (40 g, 103 mmol) in 1,4-dioxane (300 mL) and degassed several times using vacuum and nitrogen for 5 min. Chloro(1,5-cyclooctadiene) rhodium (I) dimer (2.55 g, 5.17 mmol) was added, followed by (R)-BINAP (6.44 g, 10.3 mmol) and the mixture was degassed for a further 5 min. The solution was heated at 90° C. for 60 min. After cooling, the reaction mixture was partitioned between DCM (250 mL) and water (200 mL). The aqueous phase was further extracted with DCM (200 mL) and the combined organic solutions were evaporated in vacuo. The residual oil (95 g) was dissolved in DCM and purified by chromatography on an aminopropyl cartridge KPNH (900 g) eluting with a gradient of 0-50% ethyl acetate-cyclohexane over 10CV. The appropriate fractions were combined and evaporated in vacuo to give a brown oil (39 g). Analytical chiral HPLC on Chiralpak AD-H column (250 mm×4.6 mm) eluting isocratically with 20% EtOH (containing 0.2% isopropylamine)-heptane, flow rate=1.0 mL/min, detecting at 215 nm indicated the oil was a mixture of two diastereoisomers: Peak 1 RT=7.87 min, 90.4%; Peak 2 RT=9.78 min, 9.6%. The mixture was separated by chiral preparative HPLC on a Chiralpak AD column (50 mm×200 mm), eluting with 20% ethanol (containing 0.2% isopropylamine)-heptanes, flow rate=50 mL/min, detecting at 240 nm, collecting fractions of the major component with RT=11-16 min. The combined fractions were evaporated under reduced pressure to give the major isomer of the title compound (isomer 1) (25.1 g, 45%) as a brown oil: LCMS (System A) RT=1.25 min, ES+ve m/z 540 (M+H)$^+$; Analytical chiral HPLC on Chiralpak AD-H column RT=7.87 min, >99.5%; $^1$H NMR δ (CDCl$_3$; 600 MHz) 9.07 (dd, J=4.2, 2.0 Hz, 1H), 8.15 (dd, J=8.0, 1.9 Hz, 1H), 8.08 (d, J=8.4 Hz, 1H), 7.43 (dd, J=8.0, 4.3 Hz, 1H), 7.37 (d, J=8.3 Hz, 1H), 7.37-7.33 (m, 1H), 7.27 (d, J=1.1 Hz, 1H), 7.27-7.25 (m, 1H), 7.21 (d, J=7.7 Hz, 1H), 5.98 (s, 1H), 3.31 (d, J=5.3 Hz, 1H), 3.10-2.95 (m, 2H), 2.85 (dd, J=15.4, 5.7 Hz, 1H), 2.84-2.79 (m, 1H), 2.78-2.71 (m, 1H), 2.75-2.67 (m, 1H), 2.55-2.47 (m, 1H), 2.48-2.41 (m, 1H), 2.43-2.35 (m, 1H), 2.30 (s, 3H), 2.27 (s, 3H), 2.26-2.18 (m, 1H), 2.23-2.13 (m, 1H), 2.02-1.95 (m, 1H), 1.98-1.91 (m, 2H), 1.50-1.42 (m, 1H), 1.30 (s, 9H). The fractions containing the minor component (RT=19-25 min) were combined and concentrated under reduced pressure to give the title compound isomer 2 (2.03 g, 4%) as a brown oil: LCMS (System A) RT=1.25 min, ES+ve m/z 540 (M+H)$^+$; Analytical chiral HPLC on Chiralpak AD-H column RT=9.78 min, >99.5%.

Intermediate 14: tert-Butyl 3-(3-(3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoate A solution of tert-butyl 4-((R)-3-(2-(1,8-naphthyridin-2-yl)ethyl)pyrrolidin-1-yl)-3-(3-(3,5-dimethylpyrazol-1-yl)phenyl)butanoate (isomer 1) (Intermediate 13) (8.0 g, 14.8 mmol) in ethanol (200 mL) was stirred rapidly over 10% Pd/C (1.58 g) under an atmosphere of hydrogen gas at room temperature overnight. The catalyst was removed by filtration through celite and washed with ethanol. The combined filtrate and washings were evaporated under reduced pressure to give the title compound (7.19 g, 89%) as a brown oil. LCMS (System A) RT=1.44 min, ES+ve m/z 544 (M+H)$^+$.

Intermediate 15: tert-Butyl 4-((R)-3-(2-(1,8-naphthyridin-2-yl)ethyl)pyrrolidin-1-yl)-3-(3-(5-methyl-1H-pyrazol-1-yl)phenyl)butanoate A solution of (3-(5-methyl-1H-pyrazol-1-yl)phenyl)boronic acid (Intermediate 7) (12.53 g, 55.8 mmol) in aqueous KOH (3.8M, 14.69 mL, 55.8 mmol) was treated with a solution of (R,E)-tert-butyl 4-(3-(2-(1,8-naphthyridin-2-yl)ethyl)pyrrolidin-1-yl)but-2-enoate (Intermediate 12) (11.4 g, 27.9 mmol) in 1,4-dioxane (196 mL) and the solution was degassed several times using vacuum and nitrogen for 5 min. Chloro(1,5-cyclooctadiene)rhodium(I) dimer (0.688 g, 1.396 mmol) and (R)-BINAP (1.738 g, 2.79 mmol) were added to the mixture and the solution was degassed for a further 5 min. The reaction mixture was heated at 90° C. for 60 min. After cooling, the reaction mixture was evaporated in vacuo and the residue was partitioned between DCM and water. The aqueous phase was further extracted with DCM and the combined organic solutions were evaporated in vacuo. The residual oil (21.53 g) was dissolved in DCM and purified by chromatography an aminopropyl cartridge (375 g) on CombiFlash Companion XL eluting with a gradient of from 0 to 100% ethyl acetate cyclohexane over 12 column volumes. The appropriate fractions were combined and evaporated in vacuo to give a brown oil (13.56 g). Analytical chiral HPLC on Chiralpak OD-H column (250 mm×4.6 mm) eluting isocratically with 20% EtOH heptane, flow rate=1.0 mL/min, detecting at 215 nm indicated the oil was a mixture of two diastereoisomers: Peak 1 RT=15.1 min, 8.2%; Peak 2 RT=22.6 min, 91.8%. The mixture was separated by chiral preparative HPLC on a Chiralpak AD column (50 mm×200 mm), eluting with 30% ethanol heptanes, flow rate 50 mL/min, detecting at 215 nm, collecting fractions of the major component with RT=37-50 min. The combined fractions were evaporated under reduced pressure and the residue was further purified an aminopropyl cartridge (375 g) eluting with a gradient of 0-100% ethyl acetate cyclohexane over 12 column volumes. The appropriate fractions were combined and evaporated in vacuo to give isomer 1 of the title compound (9.06 g, 62%) as a brown oil: LCMS (System A) RT=1.20 min, 97%, ES+ve m/z 526 (M+H)$^+$. Other appropriate fractions were evaporated under reduced pressure to give the minor isomer (isomer 2) of the title compound (1.83 g, 12%): LCMS (System A) RT=1.21 min, ES+ve m/z 526 (M+H)$^+$.

Intermediate 16: tert-Butyl 3-(3-(5-methyl-1H-pyrazol-1-yl)phenyl)-4-((R)-3-(2-(5,6,7,8-tetrahydro-1,8-naphthyridin-2-yl)ethyl)pyrrolidin-1-yl)butanoate A solution of tert-butyl 4-((R)-3-(2-(1,8-naphthyridin-2-yl)ethyl)pyrrolidin-1-yl)-3-(3-(5-methylpyrazol-1-yl)phenyl)butanoate (isomer 1) (Intermediate 15) (9.06 g, 17.2 mmol) in ethanol (250 mL) was hydrogenated over 10% Pd/C (1.834 g) at room temperature for 48 h. The catalyst was removed by filtration through Celite and washed with ethanol. The combined filtrate and washings were evaporated in vacuo to give the title compound (7.68 g, 84%) as a yellow oil: LCMS (System A) RT=1.40 min, 95%, ES+ve m/z 530 (M+H)$^+$.

Intermediate 17: tert-Butyl 4-((R)-3-(2-(1,8-naphthyridin-2-yl)ethyl)pyrrolidin-1-yl)-3-(3-(5-ethyl-3-methyl-1H-pyrazol-1-yl)phenyl)butanoate A mixture of (R,E)-tert-butyl 4-(3-(2-(1,8-naphthyridin-2-yl)ethyl)pyrrolidin-1-yl)but-2-enoate (Intermediate 12) (360 mg, 0.980 mmol), (3-(5-ethyl-3-methyl-1H-pyrazol-1-yl)phenyl)boronic acid (Intermediate 10) (676 mg, 2.94 mmol), aq. KOH (3.8M, 0.516 mL, 1.96 mmol), chloro(1,5-cyclooctadiene)rhodium(I) dimer (48.3 mg, 0.098 mmol), (R)-BINAP (122 mg, 0.196 mmol) in 1,4-dioxane (15 mL) was heated for 3 h at 95° C. The reaction mixture was concentrated in vacuo and partitioned between DCM (25 mL) and water (25 mL). The aqueous layer was separated and extracted with further DCM (25 mL) and the combined organic solutions were concentrated in vacuo. The residue was dissolved in DCM and purified by chromatography on a silica cartridge (50 g) eluting with 0-25% MeOH DCM. The appropriate fractions were combined and evaporated in vacuo to give the title compound (158 mg, 29%) as an orange oil: LCMS (System A) RT=1.31 min, 81%, ES+ve m/z 554 (M+H)$^+$; Analytical Chiral HPLC Chiralpak AD (250 mm×4.6 mm) 15% EtOH heptane, isocratic, flow rate 1 mL/min, detecting at 215 nm. RT=10.5 min, 92.6% (major isomer) and 14.8 min, 7.4% (minor isomer); $^1$H NMR δ (CDCl$_3$; 600 MHz) 9.10 (dd, J=4.2, 2.0 Hz, 1H), 8.17 (dd, J=8.1, 2.2 Hz, 1H), 8.11 (d, J=8.4 Hz, 1H), 7.46 (dd, J=8.1, 4.4 Hz, 1H), 7.41-7.34 (m, 2H), 7.31-7.21 (m, 3H), 6.03 (s, 1H), 3.74 (q, J=7.0 Hz, 1H), 3.33 (br. S., 1H), 3.11-2.97 (m, 2H), 2.91-2.70 (m, 4H), 2.63 (q, J=7.7 Hz, 2H), 2.56-2.38 (m, 3H), 2.33 (s, 3H), 2.27-2.14 (m, 2H), 2.06-1.92 (m, 3H), 1.51-1.45 (m, 1H), 1.36-1.31 (m, 9H), 1.19 (t, J=7.5 Hz, 3H).

Intermediate 18: tert-Butyl 3-(3-(5-ethyl-3-methyl-1H-pyrazol-1-yl)phenyl)-4-((R)-3-(2-(5,6,7,8-tetrahydro-1,8-naphthyridin-2-yl)ethyl)pyrrolidin-1-yl)butanoate tert-Butyl 4-((R)-3-(2-(1,8-naphthyridin-2-yl)ethyl)pyrrolidin-1-yl)-3-(3-(5-ethyl-3-methyl-1H-pyrazol-1-yl)phenyl)butanoate (Intermediate 17) (158 mg, 0.285 mmol) was hydrogenated over 10% Pd/C (30 mg) in ethanol (10 mL) for 18 h. The catalyst was removed by filtration through celite (10 g), and washed with ethanol. The combined filtrate and washings were evaporated in vacuo to give the title compound (130 mg, 82%) as an orange oil: LCMS (System A) RT=1.49 min, ES+ve m/z 558 (M+H)$^+$.

Intermediate 19: tert-Butyl 4-((R)-3-(2-(1,8-naphthyridin-2-yl)ethyl)pyrrolidin-1-yl)-3-(3-(1H-pyrazol-1-yl)phenyl)butanoate A mixture of (R,E)-tert-butyl 4-(3-(2-(1,8-naphthyridin-2-yl)ethyl)pyrrolidin-1-yl)but-2-enoate (Intermediate 12) (333 mg, 0.906 mmol), (3-(1H-pyrazol-1-yl)phenyl)boronic acid (available from ABCR GmbH) (511 mg, 2.72 mmol), aq. KOH (3.8M, 0.477 mL, 1.81 mmol), chloro(1,5-cyclooctadiene)rhodium(I) dimer (44.7 mg, 0.091 mmol), (R)-BINAP (113 mg, 0.196 mmol) in 1,4-dioxane (15 mL) was heated for 3 h at 95° C. The reaction mixture was concentrated in vacuo and partitioned between DCM (25 mL) and water (25 mL). The aqueous layer was separated and extracted with further DCM (25 mL), and the combined organic solutions were concentrated in vacuo. The residue was dissolved in DCM and purified by chromatography on a silica cartridge (50 g), eluting with 0-25% MeOH DCM. The appropriate fractions were combined and evaporated in vacuo to give the title compound (128 mg, 28%) as an orange oil: LCMS (System A): RT=1.22 min, ES+ve m/z 512 (M+H)$^+$; Analytical Chiral HPLC Chiralpak AD (250 mm×4.6 mm), eluting isocratically with 30% EtOH heptane containing 0.1% isopropylamine, flow rate 1 mL/min, detecting at 235 nm: RT=7.05 min, 95% (major isomer) and 12.2 min, 5% (minor isomer).

Intermediate 20: tert-Butyl 3-(3-(1H-pyrazol-1-yl)phenyl)-4-((R)-3-(2-(5,6,7,8-tetrahydro-1,8-naphthyridin-2-yl)ethyl)pyrrolidin-1-yl)butanoate tert-Butyl 4-((R)-3-(2-(1,8-naphthyridin-2-yl)ethyl)pyrrolidin-1-yl)-3-(3-(1H-pyrazol-1-yl)phenyl)butanoate (Intermediate 19) (128 mg, 0.25 mmol) was hydrogenated over 10% Pd/C (53 mg) in ethanol (10 mL) for 18 h. The catalyst was removed by filtration through celite (10 g), and washed with ethanol. The combined filtrate and washings were evaporated in vacuo to give the title compound (100 mg, 78%) as an orange oil: LCMS (System A) RT=1.45 min, ES+ve m/z 516 (M+H)$^+$.

Intermediate 21: 1-(3-Bromophenyl)-3,5-diethyl-1H-pyrazole

Heptane-3,5-dione (available from Aldrich) (3.60 g, 28.1 mmol), (3-bromophenyl)hydrazine (available from Anichem Inc) (3.50 g, 18.7 mmol) were dissolved in DCM (20 mL). Concentrated H$_2$SO$_4$ (18M, 0.100 mL, 1.8 mmol) was added and the reaction stirred at room temperature for 18 h. The reaction mixture was concentrated in vacuo and partitioned between DCM (25 mL) and water (25 mL), the aqueous phase was separated and extracted with further DCM (25 mL). The combined organic phases were concentrated in vacuo to give the title compound (3.64 g, 70%): LCMS (System A): RT=1.31 min, ES+ve m/z 279/281 (M+H)$^+$.

Intermediate 22: (3-(3,5-Diethyl-1H-pyrazol-1-yl)phenyl)boronic acid

A mixture of 1-(3-bromophenyl)-3,5-diethyl-1/1-pyrazole (Intermediate 21) (3.637 g, 13.03 mmol), 2-dicyclohexylphosphino-2',4',6'-triisopropylbiphenyl (X-PHOS) (available from Aldrich) (298 mg, 0.625 mmol), tris(dibenzylideneacetone)dipalladium (available from Aldrich) (179 mg, 0.195 mmol), potassium acetate (3.20 g, 32.6 mmol) and bis(pinacolato)diboron (available from Aldrich) (3.64 g, 14.3 mmol) in 1,4-dioxane (75 mL) was heated to 110° C. for 4 h. Water and ethyl acetate were added to the reaction mixture and the layers were separated. The aqueous layer was further extracted twice with EtOAc. The combined organic extracts were passed through a hydrophobic frit and the filtrate evaporated in vacuo. The residue was dissolved in acetonitrile and purified by reverse-phase chromatography (100 g), eluting with a gradient of 25-85% acetonitrile water containing 0.1% formic acid over 10 CV. The appropriate fractions were combined and evaporated in vacuo to give the title compound (1.055 g, 33%): LCMS (System A) RT=0.86 min, ES+ve m/z 245 (M+H)$^+$.

Intermediate 23: tert-Butyl 4-((R)-3-(2-(1,8-naphthyridin-2-yl)ethyl)pyrrolidin-1-yl)-3-(3-(3,5-diethyl-1H-pyrazol-1-yl)phenyl)butanoate A mixture of (R,E)-tert-butyl 4-(3-(2-(1,8-naphthyridin-2-yl)ethyl)pyrrolidin-1-yl)but-2-enoate (Intermediate 12) (210 mg, 0.571 mmol), (3-(3,5-diethyl-1H-pyrazol-1-yl)phenyl)boronic acid (Intermediate 22) (283 mg, 1.16 mmol), aq. KOH (3.8M, 0.3 mL, 1.14 mmol), chloro(1,5-cyclooctadiene)rhodium(I) dimer (14.1 mg, 0.03 mmol), (R)-BINAP (35.6 mg, 0.06 mmol) in 1,4-dioxane (5 mL) was heated for 4 h at 95° C. The reaction mixture was concentrated in vacuo and partitioned between EtOAc (100 mL) and water (100 mL). The aqueous layer was separated and extracted with further EtOAc (100 mL), and the combined organic solutions were concentrated in vacuo. The residue was purified by chromatography on an aminopropyl SPE cartridge (50 g), eluting with 0-100% EtOAc cyclohexane over 1 h. The appropriate fractions were combined and evaporated in vacuo to give the title compound (130 mg, 40%) as an orange oil: LCMS (System C): RT=0.97 min, ES+ve m/z 568 (M+H)+; Analytical Chiral HPLC Chiralpak AD (250 mm×4.6 mm), eluting isocratically with 10% EtOH heptane containing 0.1% isopropylamine, flow rate 1 mL/min, detecting at 215 nm: RT=10.5 min, 86% (major isomer) and 13.7 min, 13% (minor isomer). The diastereoisomers were separated by preparative chiral HPLC on a Chiralpak AD (250 mm×30 mm) eluting isocratically with 10% EtOH heptane containing 0.2% isopropylamine, flow rate 30 mL/min, detecting at 215 nm. The appropriate fractions were combined and evaporated under reduced pressure to give the major isomer of the title compound (isomer 1) (53 mg, 41%): LCMS (System C) RT=0.95 min, ES+ve m/z 568 (M+H)+; $^1$H NMR δ (CDCl$_3$; 400 MHz) 9.08 (dd, J=4, 2 Hz, 1H), 8.15 (dd, J=8, 2 Hz, 1H), 8.09 (d, J=8 Hz, 1H), 7.44 (dd, J=8, 4 Hz, 1H), 7.38 (d, J=8 Hz, 1H), 7.37-7.34 (m, 1H), 7.27-7.24 (m, 2H), 7.22 (br. d, J=8 Hz, 1H), 6.05 (s, 1H), 3.37-3.25 (br, 1H), 3.09-2.97 (m, 2H), 2.86 (dd, J=15, 5.5 Hz, 1H), 2.83-2.79 (m, 1H), 2.78-2.71 (m, 1H), 2.70 (q, J=7 Hz, 2H), 2.75-2.67 (m, 1H), 2.62 (q, J=7 Hz, 2H), 2.55-2.35 (m, 3H), 2.30-2.13 (m, 2H), 2.05-1.92 (m, 2H), 1.72-1.58 (m, 1H), 1.50-1.42 (m, 1H), 1.31 (s, 9H), 1.29 (t, J=7 Hz, 3H), 1.19 (t, J=7 Hz, 3H). Evaporation of other appropriate fractions gave the minor diastereoisomer of the title compound (isomer 2) (5 mg, 4%): LCMS (System C) RT=0.96 min, ES+ve m/z 568 (M+H)+.

Intermediate 24: tert-Butyl 3-(3-(3,5-diethyl-1/i-pyrazol-1-yl)phenyl)-4-((R)-3-(2-(5,6,7,8-tetrahydro-1,8-naphthyridin-2-yl)ethyl)pyrrolidin-1-yl)butanoate tert-Butyl 4-((R)-3-(2-(1,8-naphthyridin-2-yl)ethyl)pyrrolidin-1-yl)-3-(3-(3,5-diethyl-1H-pyrazol-1-yl)phenyl)butanoate (isomer 1) (Intermediate 23) (144 mg, 0.25 mmol) was hydrogenated over 10% Pd/C (27 mg) in ethanol (10 mL) for 18 h. The catalyst was removed by filtration through celite (10 g), and washed with ethanol. The combined filtrate and washings were evaporated in vacuo to give the title compound (116 mg, 80%) as an orange oil: LCMS (System A) RT=1.61 min, ES+ve m/z 572 (M+H)+.

Intermediate 25: 1-(3-Bromophenyl)-4-fluoro-3,5-dimethyl-1H-pyrazole

3-Fluoropentane-2,4-dione (available from Fluorochem) (2.84 g, 24.1 mmol), (3-bromophenyl)hydrazine (available from Anichem Inc) (3.0 g, 16 mmol) were dissolved in DCM (20 mL). Conc. H$_2$SO$_4$ (0.171 mL, 3.21 mmol) was added and the reaction stirred at room temperature for 18 h. The reaction mixture was concentrated in vacuo and partitioned between DCM (25 mL) and water (25 mL), the aqueous phase was separated and extracted with further DCM (25 mL). The combined organic phases were then concentrated in vacuo to give the title compound (2.61 g, 60%): LCMS (System A) RT=1.22 min, ES+ve m/z 269/271 (M+H)+.

Intermediate 26: (3-(4-Fluoro-3,5-dimethyl-1H-pyrazol-1-yl)phenyl)boronic acid

A mixture of 1-(3-bromophenyl)-4-fluoro-3,5-dimethyl-1/1-pyrazole (Intermediate 25) (2.61 g, 9.70 mmol), 2-dicyclohexylphosphino-2',4',6'-triisopropylbiphenyl (X-PHOS) (available from Aldrich) (222 mg, 0.466 mmol), tris(dibenzylideneacetone)dipalladium (available from Aldrich) (133 mg, 0.146 mmol), potassium acetate (2.38 g, 24.3 mmol) and bis(pinacolato)diboron (available from Aldrich) (2.71 g, 10.67 mmol) in 1,4-dioxane (75 mL) was heated to 110° C. for 4 h. Water and ethyl acetate were added to the reaction mixture and the layers were separated. The aqueous layer was further extracted with EtOAc. The combined organic extracts were passed through a hydrophobic frit and the filtrate evaporated in vacuo. The residue was dissolved in acetonitrile and purified by reverse phase chromatography (100 g cartridge) using a gradient of 25-85% acetonitrile water containing 0.1% formic acid over 10 CV. The appropriate fractions were combined and evaporated in vacuo to give the title compound (400 mg, 18%): LCMS (System A) RT=0.77 min, ES+ve m/z 235 (M+H)+.

Intermediate 27: tert-Butyl 4-((R)-3-(2-(1,8-naphthyridin-2-yl)ethyl)pyrrolidin-1-yl)-3-(3-(4-fluoro-3,5-dimethyl-1H-pyrazol-1-yl)phenyl)butanoate A solution of (3-(4-fluoro-3,5-dimethyl-1H-pyrazol-1-yl)phenyl)boronic acid (Intermediate 26) (382 mg, 1.63 mmol), cyclooctadiene rhodium(I) chloride dimer (121 mg, 0.245 mmol), aqueous KOH (3.8M, 0.430 mL, 1.63 mmol) in 1,4-dioxane (6 mL) was stirred at ambient temperature for 5 min under nitrogen before (R,E)-tert-butyl 4-(3-(2-(1,8-naphthyridin-2-yl)ethyl)pyrrolidin-1-yl)but-2-enoatecyclooctadiene (Intermediate 12) (300 mg, 0.82 mmol) was added. The reaction mixture was heated at 95° C. for 1 h, and then was partitioned between water (20 mL) and EtOAc (20 mL). The organic layer was concentrated under reduced pressure, dissolved in MeOH (5 mL) and loaded on a 10 g aminopropyl SPE cartridge, which was pre-conditioned with MeOH (1 CV). The column was washed with MeOH (3 CV) and the fractions were concentrated under reduced pressure. The residue (385 mg) was purified by reverse phase chromatography on a C18 (30 g) cartridge, eluting with 50-80% acetonitrile (containing 0.1% ammonia) in aqueous 10 mM ammonium bicarbonate solution. The appropriate fractions were concentrated under reduced pressure to give the title compound as a mixture of diastereoisomers (70 mg, 15%): LCMS (System A) RT=1.34 min, ES+ve m/z 558 (M+H)+.

Intermediate 28: tert-Butyl 3-(3-(4-fluoro-3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoate tert-Butyl 4-((R)-3-(2-(1,8-naphthyridin-2-yl)ethyl)pyrrolidin-1-yl)-3-(3-(4-fluoro-3,5-dimethyl-1H-pyrazol-1-yl)phenyl)butanoate (Intermediate 27) (70 mg, 0.063 mmol) was hydrogenated over 10% Pd/C (13.4 mg) in ethanol (4 mL) for 4 h. The catalyst was removed by filtration through celite, and washed with ethyl acetate. The combined filtrate and washings were concentrated under reduced pressure to give the title compound (70 mg, 35%) as a yellow oil: LCMS (System A) RT=1.50 min, ES+ve m/z 562 (M+H)+.

Intermediate 29: 1-(3-Bromophenyl)-3-methyl-1H-pyrazole

A solution of but-3-yn-2-one (1.75 mL, 22.4 mmol), (3-bromophenyl)hydrazine, hydrochloride (5.0 g, 22.4 mmol) in MeOH (20 mL) was treated with conc. HCl (0.680 mL, 22.4 mmol) and the reaction was heated in a sealed microwave vial for 2 min at 120° C. The reaction mixture was concentrated in vacuo and partitioned between DCM (25 mL) and water (25 mL), the aqueous layer was separated and extracted with further DCM (25 mL). The combined organic solutions were concentrated and purified by chromatography on silica SPE cartridge (100 g) eluting with a gradient of 0-100% DCM-cyclohexane. The appropriate fractions were combined and evaporated in vacuo to give the title compound (2.39 g, 45%): LCMS (System A) RT=1.15 min, ES+ve m/z 237/239 (M+H)+; 1H NMR δ (CDCl3; 600 MHz) 7.85 (t, J=2.0 Hz, 1H), 7.75 (d, J=2.4 Hz, 1H), 7.54 (ddd, J=8.2, 2.1, 0.9 Hz, 1H), 7.35-7.31 (m, 1H), 7.26-7.21 (m, 1H), 6.23 (d, J=2.4 Hz, 1H), 2.35 (s, 3H), and its regioisomer 1-(3-bromophenyl)-5-methylpyrazole (Intermediate 6) (1.7 g, 32%): LCMS (System A) RT=1.05 min, ES+ve m/z 237/239 (M+H)+.

Intermediate 30: (3-(3-Methyl-1H-pyrazol-1-yl)-phenyl)boronic acid

Was prepared by a method similar to that described for the preparation of Intermediate 26, starting from Intermediate 29 (2.39 g, 10.1 mmol) to provide the title compound (2.23 g, 100%): LCMS (System A) RT=0.60 min, ES+ve m/z 203 (M+H)+.

Intermediate 31: tert-Butyl 4-((R)-3-(2-(1,8-naph-thyridin-2-yl)ethyl)pyrrolidin-1-yl)-3-(3-(3-methyl-1H-pyrazol-1-yl)phenyl)butanoate Was prepared by a method similar to that described for the preparation of Intermediate 27, starting from Intermediate 12 (336 mg, 0.914 mmol) and Intermediate 30 (554 mg, 2.74 mmol) to provide the title compound (212 mg, 44%): LCMS (System A) RT=1.26 min, ES+ve m/z 526 (M+H)+; Analytical Chiral HPLC Chiralcel OD (250 mm×4.6 mm), eluting isocratically with 40% EtOH-heptane, flow rate 1 mL/min, detecting at 215 nm: RT=10.1 min, 16.7% (minor isomer) and 14.1 min, 83.3% (major isomer).

Intermediate 32: tert-Butyl 3-(3-(3-methyl-1H-pyra-zol-1-yl)phenyl)-4-((R)-3-(2-(5,6,7,8-tetrahydro-1,8-naphthyridin-2-yl)ethyl)pyrrolidin-1-yl)butanoate A solution of tert-butyl 4-((R)-3-(2-(1,8-naphthyridin-2-yl)ethyl)pyrrolidin-1-yl)-3-(3-(3-methylpyrazol-1-yl)phenyl)butanoate (Intermediate 31) (212 mg, 0.403 mmol) in EtOH (10 mL) was hydrogenated over Pd/C (42.9 mg) for 18 h. The catalyst was collected by filtration through celite, and washed with EtOH. The combined filtrate and washings were concentrated in vacuo to give the title compound (171 mg, 80%) as an orange oil: LCMS (System A): RT=1.46 min, ES+ve m/z 530 (M+H)+.

PREPARATION OF EXAMPLES

Example 1: 3-(3-(3,5-Dimethyl-1H-pyrazol-1-yl)phenyl)-4-((R)-3-(2-(5,6,7,8-tetrahydro-1,8-naphthy-ridin-2-yl)ethyl)pyrrolidin-1-yl)butanoic acid

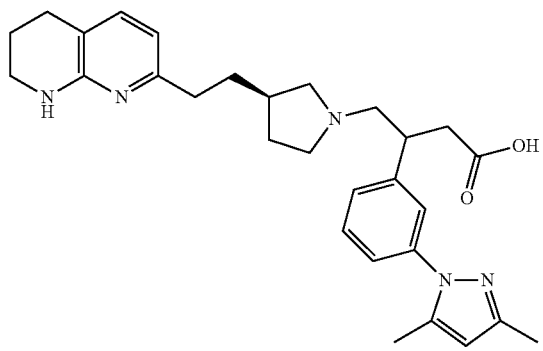 [SMILES: Cc1cc(C)n(-c2cccc(C(CC(=O)O)CN3CC[C@@H](CCc4ccc5c(n4)NCCC5)C3)c2)n1]

A solution of tert-butyl 3-(3-(3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoate (Intermediate 14) (100 mg, 0.184 mmol) in 2-methyl THF (0.5 mL) was treated with conc. HCl (12M, 0.077 mL, 0.92 mmol) and stirred at 40° C. for 2 h. The solvent was evaporated in vacuo and the residual oil was dissolved in ethanol (2 mL) and applied to a SCX-2 ion-exchange cartridge (5 g), eluting with ethanol (2 CV) and then 2M ammonia in MeOH (2 CV). The ammoniacal fractions were combined and evaporated in vacuo to give the title compound (79 mg, 88%) as an off-white solid: LCMS (System A) RT=0.86 min, 100%, ES+ve m/z 488 (M+H)+; 1H NMR δ (CDCl3; 600 MHz): 7.42-7.37 (m, 1H), 7.31 (d, J=1.5 Hz, 1H), 7.29 (d, J=0.9 Hz, 1H), 7.23 (d, J=7.7 Hz, 1H), 7.21 (d, J=7.3 Hz, 1H), 6.31 (d, J=7.3 Hz, 1H), 5.99 (s, 1H), 3.55 (br. s., 1H), 3.60-3.52 (m, 1H), 3.45 (t, J=5.4 Hz, 2H), 3.27 (t, J=10.6 Hz, 1H), 3.09 (br. s., 1H), 2.93-2.86 (m, 1H), 2.82 (d, J=10.1 Hz, 1H), 2.86-2.75 (m, 2H), 2.72 (t, J=6.2 Hz, 2H), 2.74-2.67 (m, 2H), 2.75 (d, J=9.0 Hz, 1H), 2.61-2.50 (m, 1H), 2.31 (s, 3H), 2.29 (s, 3H), 2.33-2.26 (m, 1H), 2.24-2.11 (m, 1H), 1.94-1.86 (m, 2H), 1.94-1.84 (m, 1H), 1.78-1.66 (m, 1H), 1.65-1.51 (m, 1H).

Example 1 was identified by a method described hereinafter as (S)-3-(3-(3,5-dimethyl-1/1-pyrazol-1-yl)phenyl)-4-((R)-3-(2-(5,6,7,8-tetrahydro-1,8-naphthyridin-2-yl)ethyl)pyrrolidin-1-yl)butanoic acid.

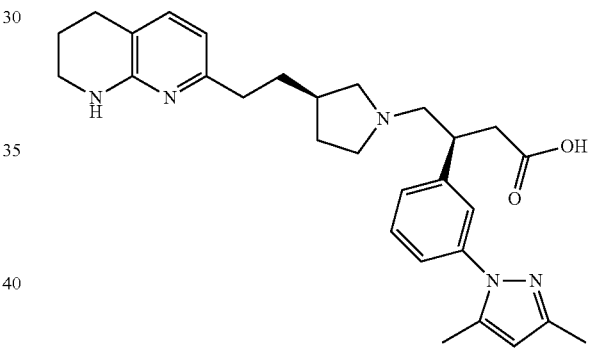

Example 2: 3-(3-(5-Methyl-1H-pyrazol-1-yl)phe-nyl)-4-((R)-3-(2-(5,6,7,8-tetrahydro-1,8-naphthyri-din-2-yl)ethyl)pyrrolidin-1-yl)butanoic acid

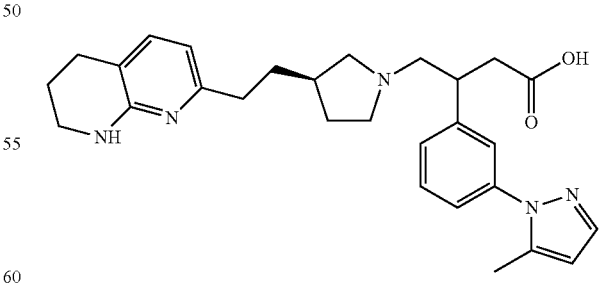

A solution of tert-butyl 3-(3-(5-methyl-1H-pyrazol-1-yl)phenyl)-4-((R)-3-(2-(5,6,7,8-tetrahydro-1,8-naphthyridin-2-yl)ethyl)pyrrolidin-1-yl)butanoate (Intermediate 16) (2.80 g, 5.29 mmol) in 2-methyl THF (15 mL) was treated with conc. HCl (12M, 3.96 mL, 47.6 mmol) and stirred at 40° C. for 2 h. The solvent was evaporated in vacuo and the residue (3.8 g) was dissolved in ethanol (2 mL) and purified by ion-exchange chromatography on SCX-2 cartridge (70 g), eluting with ethanol (1 CV) and then with 2M ammonia in MeOH (1 CV). The ammoniacal fractions were evaporated in vacuo and the residue was dissolved in DCM and further purified on an aminopropyl cartridge (100 g) eluting with a gradient of 0-25% MeOH DCM over 30 min. The appropriate fractions were combined and evaporated in vacuo to give the title compound (2.01 g, 80%) as a white foam: LCMS (System A) RT=0.83 min, 100%, ES+ve m/z 474 (M+H)$^+$; $^1$H NMR δ (DMSO-d$_6$; 600 MHz) 7.55 (d, J=1.5 Hz, 1H), 7.47-7.41 (m, 1H), 7.38 (s, 1H), 7.34 (d, J=8.1 Hz, 1H), 7.30 (d, J=7.7 Hz, 1H), 7.02 (d, J=7.0 Hz, 1H), 6.32-6.22 (m, 3H), 3.35-3.26 (m, 2H), 3.26-3.20 (m, 2H), 2.92-2.75 (m, 3H), 2.73-2.65 (m, 1H), 2.63-2.52 (m, 4H), 2.47 (dd, J1=15.8, 7.3 Hz, 1H), 2.41 (t, J=7.7 Hz, 2H), 2.33 (s, 3H), 2.28 (dd, J1=9.0, 7.5 Hz, 1H), 2.10-1.96 (m, 1H), 1.94-1.85 (m, 1H), 1.79-1.71 (m, 2H), 1.68-1.54 (m, 2H), 1.34 (dd, J1=12.3, 7.9 Hz, 1H).

Example 3: 3-(3-(5-Ethyl-3-methyl-1H-pyrazol-1-yl)phenyl)-4-((R)-3-(2-(5,6,7,8-tetrahyrdro-1,8-naphthyridin-2-yl)ethyl)pyrrolidin-1-yl)butanoic acid

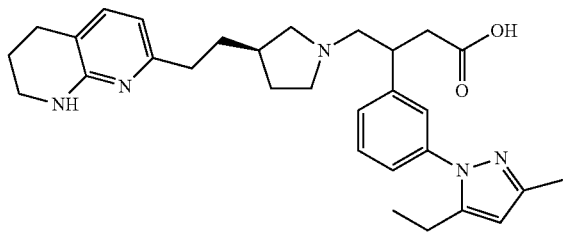 [SMILES: CCc1cc(C)nn1-c1cccc(C(CC(=O)O)CN2CC[C@@H](CCc3ccc4c(n3)NCCC4)C2)c1]

tert-Butyl 3-(3-(5-ethyl-3-methyl-1H-pyrazol-1-yl)phenyl)-4-((R)-3-(2-(5,6,7,8-tetrahydro-1,8-naphthyridin-2-yl)ethyl)pyrrolidin-1-yl)butanoate (Intermediate 18) (130 mg, 0.233 mmol) was dissolved in 1,4-dioxane (5 mL), conc. HCl (37%, 0.038 mL, 0.466 mmol) was added, and the reaction mixture was stirred at room temperature for 18 h. The mixture was concentrated in vacuo and the sample was dissolved in DMSO (1 mL) and purified by Mass Directed AutoPrepHPLC (Method B) on Xbridge column using acetonitrile-water with an ammonium carbonate buffer. The solvent was removed under a stream of nitrogen in a Radley's blow-down apparatus to give the title compound (20 mg, 17%): LCMS (System A) RT=0.90 min, 95%, ES+ve m/z 502 (M+H)$^+$; $^1$H NMR δ (CD$_3$OD; 400 MHz) 7.48 (t, J=8 Hz, 1H), 7.39-7.32 (m, 2H), 7.30 (br d, J=8 Hz, 1H), 7.14 (d, J=7.5 Hz, 1H), 6.38 (d, J=7.5 Hz, 1H), 6.10 (s, 1H), 3.62-3.45 (m, 2H), 3.39-3.32 (m, 4H), 3.25 (dd, J=12, 3 Hz, 1H), 3.08 (br. t, J=9 Hz, 1H), 2.86 (dd, J=16, 10 Hz, 1H), 2.71-2.53 (m, 7H), 2.38-2.26 (m, 1H), 2.25 (s, 3H), 2.24-2.16 (m, 1H), 1.90-1.63 (m, 5H), 1.16 (t, J=7.5 Hz, 3H).

Example 4: 3-(3-(1H-Pyrazol-1-yl)phenyl)-4-((R)-3-(2-(5,6,7,8-tetrahydro-1,8-naphthyridin-2-yl)ethyl)pyrrolidin-1-yl)butanoic acid

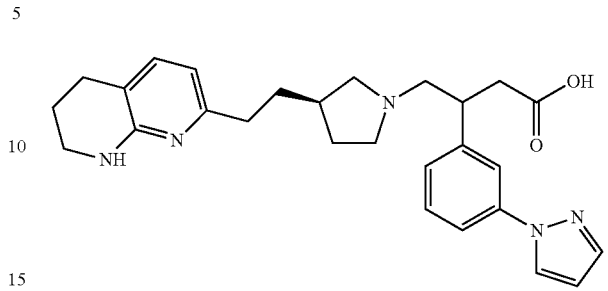

tert-Butyl 3-(3-(1H-pyrazol-1-yl)phenyl)-4-((R)-3-(2-(5,6,7,8-tetrahydro-1,8-naphthyridin-2-yl)ethyl)pyrrolidin-1-yl)butanoate (Intermediate 20) (100 mg, 0.19 mmol) was dissolved in 1,4-dioxane (5 mL), conc. HCl (37%, 0.032 mL, 0.39 mmol) was added, and the reaction mixture was stirred at room temperature for 18 h. The mixture was concentrated in vacuo and the sample was dissolved in DMSO-MeOH (1:1; 1 mL) and purified by Mass Directed AutoPrepHPLC (Method A) on Xbridge column using acetonitrile-water with an ammonium carbonate buffer. The solvent was removed under a stream of nitrogen in a Radley's blow-down apparatus to give the title compound (10 mg, 11%): LCMS (System A) RT=0.82 min, 98.6%, ES+ve m/z 460 (M+H)$^+$; $^1$H NMR δ (CD$_3$OD; 400 MHz) 8.23 (d, J=2.5 Hz, 1H), 7.72 (br. d, J=2 Hz, 1H), 7.68 (m, 1H), 7.63 (br. d, J=8 Hz, 1H), 7.46 (t, J=8 Hz, 1H), 7.25 (br. d, J=7.5 Hz, 1H), 7.15 (d, J=7.5 Hz, 1H), 6.52 (m, 1H), 6.38 (d, J=7.5 Hz, 1H), 3.64-3.45 (m, 2H), 3.39-3.32 (m, 4H), 3.26 (obscured by CHD$_2$OD, 1H), 3.15-3.06 (m, 1H), 2.88 (dd, J=16.5, 10 Hz, 1H), 2.71-2.61 (m, 3H), 2.56 (t, J=8 Hz, 2H), 2.40-2.28 (m, 1H), 2.26-2.16 (m, 1H), 1.90-1.61 (m, 5H).

Example 5: 3-(3-(3,5-Diethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid

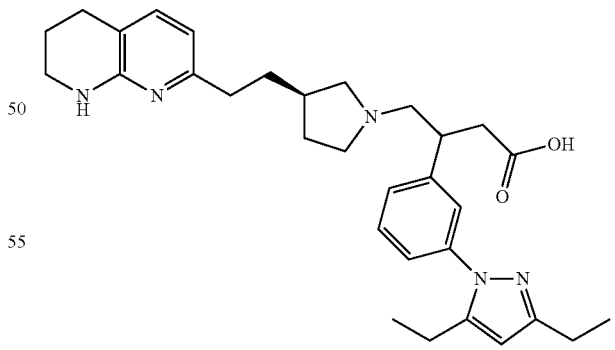

tert-Butyl 3-(3-(3,5-diethyl-1H-pyrazol-1-yl)phenyl)-4-((R)-3-(2-(5,6,7,8-tetrahydro-1,8-naphthyridin-2-yl)ethyl)pyrrolidin-1-yl)butanoate (116 mg, 0.203 mmol) was dissolved in 1,4-dioxane (5 mL) and then treated with conc. HCl (0.033 mL, 0.406 mmol) and the reaction stirred at room temperature for 18 h. The reaction was concentrated in vacuo and the residue was dissolved in DMSO (1 mL) and purified by Mass Directed AutoPrep HPLC (Method A) on Xbridge column using acetonitrile water with an ammonium carbonate buffer. The solvent was dried under a stream of nitrogen in the Radleys blow-down apparatus to give the title compound (27 mg, 26%): LCMS (System A) RT=0.94 min, ES+ve m/z 516 (M+H)⁺: ¹H NMR δ (CD₃OD; 600 MHz) 7.49 (t, 1=8.0 Hz, 1H), 7.37 (d, J=8.0 Hz, 1H), 7.34 (br. s, 1H), 7.31 (br. d, 1=8.0 Hz, 1H), 7.14 (d, J=7.3 Hz, 1H), 6.38 (d, J=7.3 Hz, 1H), 6.14 (s, 1H), 3.57 (dd, J=12.5, 9.4 Hz, 1H), 3.53-3.47 (m, 1H), 3.39-3.33 (m, 3H), 3.32-3.29 (m, 2H), 3.25 (dd, J=12.6, 3.6 Hz, 1H), 3.10-3.01 (m, 1H), 2.86 (dd, 1=16.4, 10.4 Hz, 1H), 2.68 (t, J=6.2 Hz, 2H), 2.67-2.61 (m, 1H), 2.66-2.58 (m, 4H), 2.56 (t, J=7.8 Hz, 2H), 2.38-2.28 (m, 1H), 2.21 (d, J=6.8 Hz, 1H), 1.88-1.83 (m, 2H), 1.83-1.72 (m, 2H), 1.67 (dd, J=13.0, 8.4 Hz, 1H), 1.25 (t, J=7.7 Hz, 3H), 1.17 (t, J=7.6 Hz, 3H)

Example 6: 3-(3-(4-Fluoro-3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid

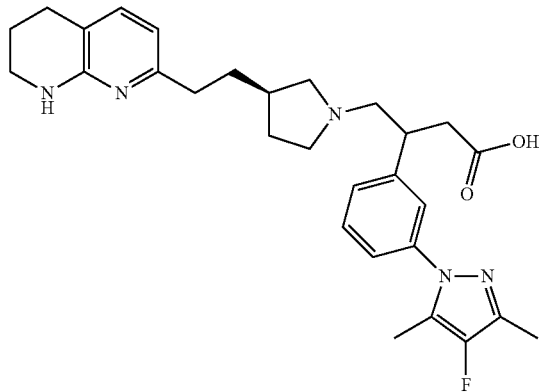 [SMILES: Cc1nn(-c2cccc(C(CC(=O)O)CN3CC[C@@H](CCc4ccc5c(n4)NCCC5)C3)c2)c(C)c1F]

tert-Butyl 3-(3-(4-fluoro-3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoate (Intermediate 28) (70 mg, 0.125 mmol) was dissolved in acetonitrile (1 mL) and 4M HCl in dioxane (0.093 mL, 0.37 mmol) was added. The reaction mixture was stirred at ambient temperature for 2 h. LCMS at this point showed very low conversion to the product and more 4M HCl in dioxane (0.093 mL, 0.37 mmol) was added and the reaction mixture was stirred for another 8 h. The reaction mixture was concentrated under reduced pressure, dissolved in MeOH-DMSO (1:1; 2 mL) and purified by MDAP (Method A). The appropriate fractions were combined and concentrated under a nitrogen stream in a blow-down unit to give the title compound (30 mg, 48%) as an orange gum: LCMS (System A) RT=0.90 min, 98.5%, ES+ve m/z 506 (M+H)⁺; ¹H NMR δ (CD₃OD; 400 MHz) 7.49 (t, J=8 Hz, 1H), 7.40-7.31 (m, 3H), 7.13 (t, J=8 Hz, 1H), 6.38 (m, 1H), 3.61-3.46 (m, 3H), 3.44-3.32 (m, 4H), 3.28-3.21 (m, 2H), 2.90-2.80 (m, 2H), 2.74-2.50 (m, 5H), 2.41-2.28 (m, 1H), 2.25 (d, J=9 Hz, 6H), 2.22-2.14 (m, 1H), 1.90-1.66 (m, 4H).

Example 7: 3-(3-(3-Methyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid

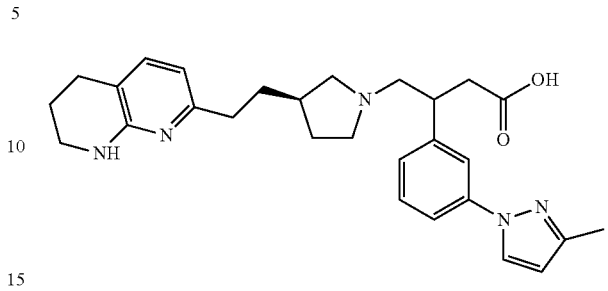

tert-Butyl 3-(3-(3-methyl-1H-pyrazol-1-yl)phenyl)-4-((R)-3-(2-(5,6,7,8-tetrahydro-1,8-naphthyridin-2-yl)ethyl)pyrrolidin-1-yl)butanoate (Intermediate 32) (92 mg, 0.17 mmol) was dissolved in 1,4-dioxane (5 mL) and then treated with conc. HCl (0.029 mL, 0.35 mmol) and the reaction stirred at room temperature for 18 h. The reaction was concentrated in vacuo and the residue dissolved in DMSO (1 mL) and purified by Mass Directed AutoPreparative HPLC (Method A). Appropriate fractions were combined and evaporated under a stream of nitrogen gas in a Radleys blow-down apparatus to give the title compound (18 mg, 22%): LCMS (System A) RT=0.84 min, ES+ve m/z 474 (M+H)⁺; ¹H NMR δ (CD₃OD; 400 MHz) 9.15 (d, J=2.5 Hz, 1H), 8.46 (t, J=1.5 Hz, 1H), 8.40 (dd, J=8, 1.5 Hz, 1H), 8.16 (t, J=8 Hz, 1H), 7.93 (br d, J=8 Hz, 1H), 7.81 (d, J=7.5 Hz, 1H), 7.11 (d, J=2 Hz, 1H), 7.09-7.06 (m, 1H), 7.04 (d, J=7.5 Hz, 1H), 4.11-4.00 (m, 3H), 3.72-3.57 (m, 3H), 3.54-3.46 (m, 1H), 3.45-3.32 (m, 4H), 3.29-3.16 (m, 3H), 3.15-3.09 (m, 1), 3.07 (s, 3H), 2.87-2.77 (m, 1H), 2.75-2.65 (m, 1H), 2.58-2.50 (m, 2H), 2.46-2.35 (m, 2H), 2.19-2.09 (m, 1H).

Example 8: (S)-3-(3-(3,5-Dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid, hydrochloride salt 3-(3-(3,5-Dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid (Example 1) (37.89 g, 78 mmol) was further purified by preparative chiral HPLC. This was dissolved in ethanol (4 mL) and the solution was diluted with heptane (6 mL). The solution was left to stand for 30 minutes and then filtered. The filtrate was injected (1 g per injection) onto a Chiralpak AD column (20 micron, 75 mm×250 mm) eluting isocratically with 30% ethanol (containing 0.1% isopropylamine)—70% heptane (containing 0.1% isopropylamine). Appropriate fractions were combined and evaporated in vacuo to give pure Example 1 (31.87 g) as an off-white foam. Various other batches were purified in a similar way and Large Scale Preparation of Example 8: (S)-3-(3-(3,5-Dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid, hydrochloride salt The large scale preparation of Example 8 is outlined in the scheme below:

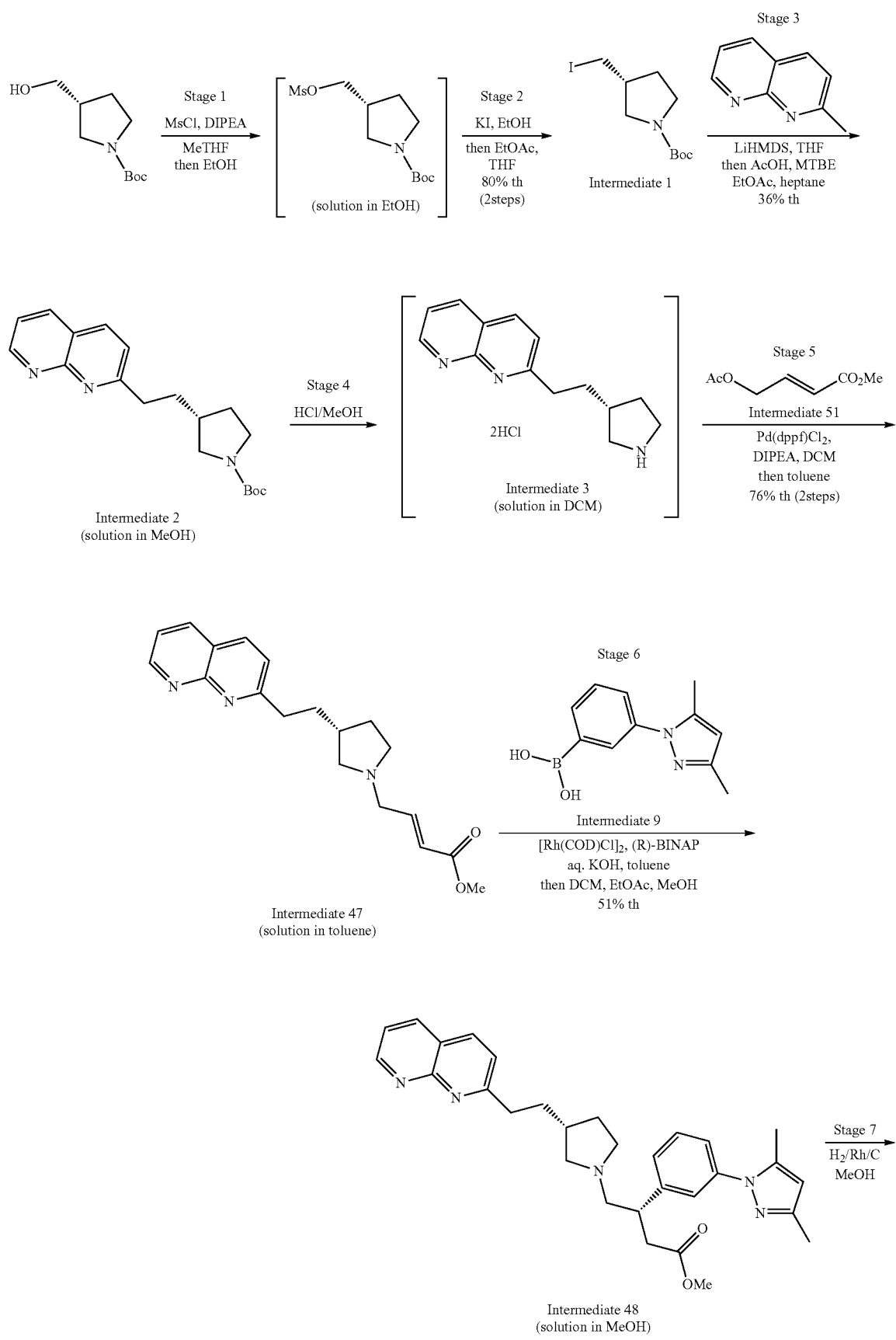

-continued
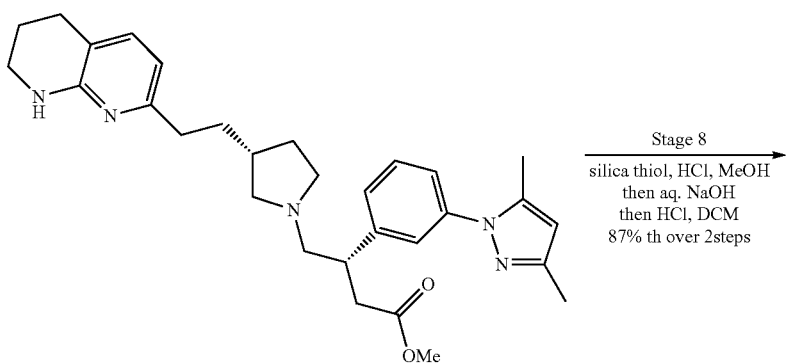
Intermediate 49
(solution in MeOH)
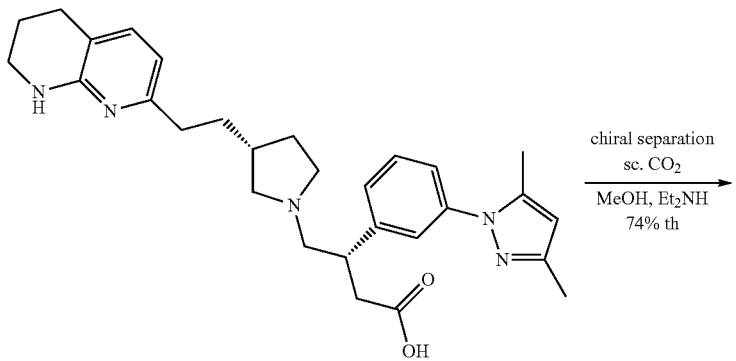
Intermediate 50
(solution in DCM)
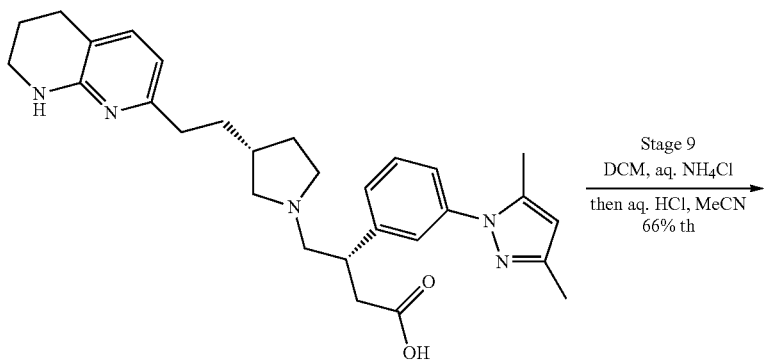
Example 1
(solution in MeOH/Et₂NH
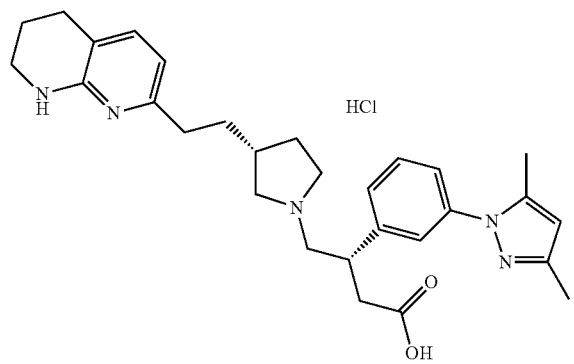
Example 9

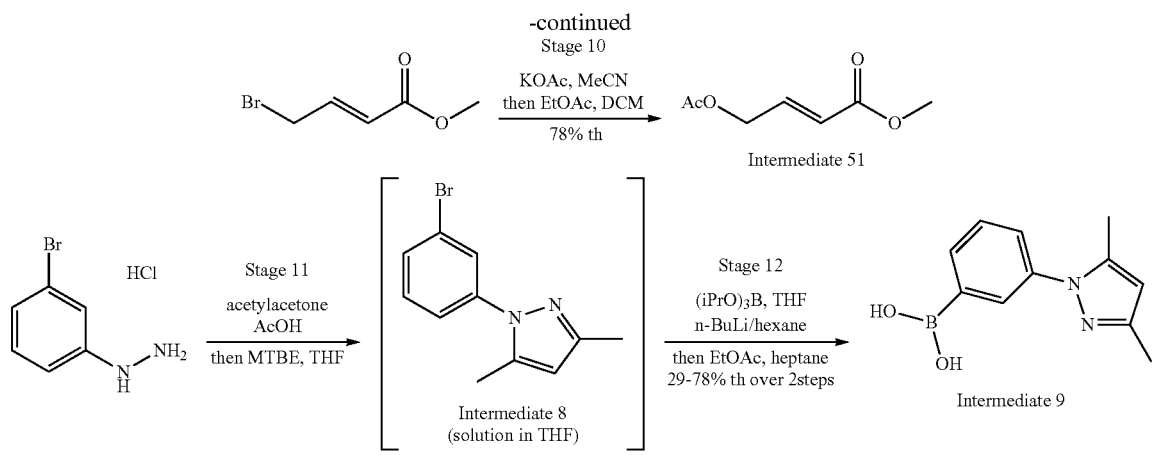

Intermediate 1 (R)-tertbutyl 3-(iodomethyl)pyrrolidine-1-carboxylate Stages 1&2. (Alternative Method)

To a reactor under nitrogen, were charged 2-Methyltetrahydrofuran (145 kg), N,N-diisopropylethylamine (16.6 kg) and (R)-tert-butyl 3-(hydroxymethyl)pyrrolidine-1-carboxylate (16.5 kg). The batch was cooled to 0-10° C. and methanesulfonyl chloride (11.6 kg) added, followed by 2-Methyltetrahydrofuran (8 kg) and the reaction stirred for about 5 hours. Further methanesulfonyl chloride (2.4 kg) was added, followed by 2-Methyltetrahydrofuran (5.2 kg) and the reaction stirred for about 4.5 hours. The reaction mixture was washed successively with 10% aqueous sodium hydroxide solution (80 kg), water (85 kg), 1N aqueous ammonium chloride solution (101 kg), water (100 kg) and 25% aq. NaCl (100 kg). The organic phase was distilled to 2-3 vol under reduced pressure and diluted with Ethanol (78 kg). The mixture was distilled to 2-3 vol under reduced pressure and diluted with Ethanol (72 kg). The mixture was distilled to 2-3 vol under reduced pressure and diluted with Ethanol (77 kg). To the mixture was added ethanol (72 kg) and potassium iodide (70 kg) and the reaction mixture was heated to 70-80° C. for 16 hours before being cooled to 40-50° C. The reaction mixture was heated to 70-80° C. for 8 hours before being cooled to 40-50° C. The reaction mixture was heated to 70-80° C. for 4 hours before being cooled to 40-50° C. The mixture was distilled to 2-3 vol under reduced pressure. Water (180 kg) and ethyl acetate (80 kg) were added to the concentrate and the organic layer was washed successively with water (90 kg) and 25% aqueous sodium chloride solution (98 kg). The remaining organic phase was distilled to 1-3 vol under reduced pressure and diluted with THF (76 kg). The mixture was distilled to 1-3 vol under reduced pressure and diluted with THF (76 kg). The mixture was distilled to 1-3 vol under reduced pressure and diluted with THF (33 kg). The mixture was distilled to 1-3 vol under reduced pressure and diluted with THF (34 kg). The mixture was diluted with THF (31 kg) to give a solution of the product that was used in next step directly (89.6 kg, 22.4% w/w assay, 80% theoretical).

HPLC RT=15.15 min, 86.1%
Column: 150 mm×4.6 mm ID, 3.5 μm Agilent Zorbax SB-C8
Flow Rate: 1.0 mL/min.
Temp.: 40° C.
Detection wavelength: 210 nm
Solvents: A: 0.05% v/v solution of trifluoroacetic acid in water
B: 0.05% v/v solution of trifluoroacetic acid in acetonitrile

| Gradient: | | |
|---|---|---|
| Time (min) | A % | B % |
| 0.01 | 95 | 5 |
| 15.0 | 5 | 95 |
| 18.0 | 5 | 95 |
| 18.0 | 95 | 5 |

Intermediate 2. (R)-tert-Butyl 3-(2-(1,8-naphthyridin-2-yl)ethyl)pyrrolidine-1-carboxylate Stage 3

Preparation of solution 1: The solution of (R)-tert-butyl 3-(iodomethyl)pyrrolidine-1-carboxylate (Intermediate 1) (89.6 kg, 22.4% assay, 20.1 kg active) was distilled under reduced pressure to 1-2 vol and diluted with THF (180 kg) and 2-Methylnaphthyridine (9.2 kg) was added and the solution cooled to 5-7° C. under nitrogen.

Preparation of solution 2: A solution of Lithium bis (trimethylsily)amide in THF (59.2 kg) was cooled to 5-7° C. under nitrogen.

The reaction was performed by pumping solutions 1 and 2 prepared above through a static mixture and flow reactor according to the conditions below with the output reaction mixture being quenched into a solution of water (80 kg) and acetic acid (42 kg).

| Residence time | Temperature | Length of tubing | Volume of tubing | Volume of Mixer | Internal Diameter of tube |
|---|---|---|---|---|---|
| 12 min | 5~7° C. | 48.05 m | 564 mL | 1~2 mL | 0.386 cm |
| The pump heading tubing | Material of tubing | Mixer | Flow rate of Pump1 | Flow rate of Pump2 | Total reaction time |
| Teflon in silicone | Teflon | Stainless steel static mixer*2 | 35.945 mL/min | 11.054 mL/min | 96 h |

Work-Up:

The mixture was treated with 2N NaOH solution (347 kg) and extracted with MTBE (160 kg). The MTBE phase was treated with 1N HCl solution (196 kg) at 0-10° C. and the organic layer discarded. The acidic aqueous layer was washed with MTBE twice (142 kg and 146 kg) and then adjusted to pH5-6 by the addition of 2N aq, NaOH (80 kg). The aqueous phase was extracted with ethyl acetate (162 kg) and the aqueous phase adjusted to pH5-6 by the addition of NaOH (14 kg). The aqueous phase was extracted with ethyl acetate (166 kg) and the aqueous phase adjusted to pH5-6 by the addition of NaOH (10 kg). The aqueous phase was extracted with ethyl acetate (176 kg) and the combined EtOAc phases washed with water (210 kg) and 25% aq. sodium chloride solution (210 kg) The organic solution was distilled under reduced pressure to 2-4 vol and diluted with MTBE (80 kg). The mixture was distilled under reduced pressure to 2-4 vol and diluted with n-heptane (80 kg). The mixture was distilled under reduced pressure to 2-4 vol and diluted with n-heptane (80 kg). The mixture was distilled under reduced pressure to 2-4 vol and diluted with MTBE (16 kg). The mixture was cooled to 5-10° C. and treated with n-heptane (40 kg). The solid product was collected by filtration (centrifuge), washed with n-heptane (10 kg) and dried at 50-60° C. under vacuum to give the title product as a solid (4.3 kg).

The filtrate was treated with EtOAc (203 kg) and distilled to 100-150 L under reduced pressure. The mixture was diluted with MTBE (80 kg) and distilled to 80 L under reduced pressure. The mixture was diluted with n-heptane (60 kg) and distilled to 60 L under reduced pressure. The mixture was diluted with n-heptane (23 kg) and distilled to 60 L under reduced pressure. The mixture was diluted with MTBE (16 kg) and distilled to 80 L under reduced pressure. The mixture was diluted with MTBE (8 kg) and distilled to 60-80 L under reduced pressure. The mixture was diluted with MTBE (8 kg) and cooled to 5-10° C. under nitrogen. The mixture was treated with n-heptane (21 kg) and stirred for about an hour. The solid product was collected by filtration (centrifuge), washed with n-heptane (5 kg) and dried at 50-60° C. under vacuum to give a second crop of the title product as a solid (3.65 kg).

Total 7.95 kg, 36% theoretical,
HPLC 1$^{st}$ crop RT=9.33 min, 97.6%,
HPLC 2$^{nd}$ crop RT=9.27 min, 99.1%,
Column: 150 mm×4.6 mm ID, 3.5 μm Agilent Zorbax SB-C8
Flow Rate: 1.0 mL/min.
Temp.: 40° C.
Detection wavelength: 210 nm
Solvents: A: 0.05% v/v solution of trifluoroacetic acid in water
B: 0.05% v/v solution of trifluoroacetic acid in acetonitrile

| Gradient: | | |
|---|---|---|
| Time (min) | A % | B % |
| 0.01 | 80 | 20 |
| 15.0 | 5 | 95 |
| 18.0 | 5 | 95 |
| 18.1 | 80 | 20 |

Chiral HPLC combined RT=28.95 min, 98.8%,
Column: 250 mm×4.6 mm ID, Chiralpak IC
Flow Rate: 1.0 mL/min.

Temp.: 30° C.
Detection wavelength: 218 nm
Solvents: A: 0.1% v/v solution of isobutylamine in n-heptane
B: 0.1% v/v solution of isobutylamine in ethanol

| Gradient: | | |
|---|---|---|
| Time (min) | A % | B % |
| 0.01 | 70 | 30 |
| 40 | 70 | 30 |

Intermediate 51. (E)-Methyl 4-acetoxybut-2-enoate
Stage 10

To a reactor, were charged acetonitrile (140 kg), potassium acetate (10 kg), (E)-methyl 4-bromobut-2-enoate (18 kg, 1 wt) and acetonitrile (3 kg). The mixture was stirred at 45-55° C. for about 12.5 h and cooled to 20-30° C. The mixture was filtered and the filter cake was washed with ethyl acetate (14 kg). The filtrate was concentrated under reduced pressure to 2-3 vol and was diluted with ethyl acetate (90 kg). The solution was washed with water 4 times (2×91 kg, 2×92 kg) and with 11% aq. sodium chloride solution (99 kg). The organic phase was concentrated under reduced pressure to 1-2 vol and DCM (80 kg) was added. The organic phase was concentrated under reduced pressure to 1-2 vol and DCM (80 kg) was added. The organic phase was concentrated under reduced pressure to 1-2 vol to give a solution of the title compound in DCM (14.8 kg, 53.4% assay, 78% th).

HPLC RT=10.37 min, 83.9%,
Column: 150 mm×4.6 mm ID, 3.5 ?inn Agilent Zorbax SB-C8
Flow Rate: 1.0 mL/min.
Temp.: 40° C.
Detection wavelength: 210 nm
Solvents: A: 0.05% v/v solution of trifluoroacetic acid in water
B: 0.05% v/v solution of trifluoroacetic acid in acetonitrile

| Gradient: | | |
|---|---|---|
| Time (min) | A % | B % |
| 0.01 | 95 | 5 |
| 15.0 | 5 | 95 |
| 18.0 | 5 | 95 |
| 18.1 | 95 | 5 |

Intermediate 47. (R,E)-Methyl 4-(3-(2-(1,8-naphthyridin-2-yl)ethyl)pyrrolidin-1-yl)but-2-enoate.
Steps 4&5

A solution of HCl in MeOH was prepared by sparging HCl gas into Methanol (40 kg) at −10 to 0° C. until a concentration of 4.6 mol/L was reached. To this solution was added a solution of Intermediate 2 (8 kg, 1 wt) in MeOH (24 kg) and heated to 35-45° C. for about 4.5 hours under nitrogen. The reaction was distilled under reduced pressure to 2-3 vol. MeOH (21 kg) was added and the mixture was concentrated under reduced pressure to 2-3 vol. MeOH (24 kg) was added and the mixture was concentrated under reduced pressure to 2-3 vol. DCM (64 kg) was added and the mixture was concentrated under reduced pressure to 2-3 vol. DCM (64 kg) was added and the mixture was concentrated under reduced pressure to 2-3 vol. DCM (64 kg) was added and the mixture adjusted to 10-20° C. and treated dropwise with N,N-diisopropylethylamine (20 kg) keeping the temperature<30° C. to give a solution of (R)-2-(2-(pyrrolidin-3-yl)ethyl)-1,8-naphthyridine, dihydrochloride salt (Intermediate 3). To another reactor was charged DCM (61 kg), (E)-methyl 4-acetoxybut-2-enoate (Intermediate 51) (53% w/w solution in DCM, 8.8 kg, 4.7 kg active), and 1,1'-[bis(diphenylphosphino)ferrocene]palladium (II) chloride (2.1 kg) and the reactor headspace purged with nitrogen and stirred at 20-30° C. for 30 min. To this mixture was added the solution of (R)-2-(2-(pyrrolidin-3-yl)ethyl)-1,8-naphthyridine, dihydrochloride salt (Intermediate 3) prepared above and the mixture stirred at 20-30° C. for about 22 h. The reaction mixture was treated with water (85 kg) and filtered through diatomite (6 kg; pre-wetted with DCM (22 kg)) washing with DCM (19 kg). The organic phase was washed with water (80 kg), cooled to 5-10° C. and acidified with 0.5N HCl (204 kg). The aqueous layer was washed with DCM (60 kg), diluted with DCM (123 kg) and neutralised with 1N NaOH solution (78 kg). The aqueous layer was extracted with DCM (59 kg). The combined DCM phases were washed with 25% NaCl solution (46 kg) and concentrated under reduced pressure to 1-2 vol. Toluene (34 kg) was added and the mixture concentrated under reduced pressure to 35-45 L to give a solution of the title compound (42.15 kg, 13.4% assay, 76% th yield). No analysis was carried out here as the material was unstable, so it was used directly in the next step.

Intermediate 9
(3-(3,5-Dimethyl-1H-pyrazol-1-yl)phenyl)boronic acid. Stacie 11&12

To a reactor, was charged 3-bromophenylhydrazine hydrochloride (6 kg), acetyl acetone (4031.7 g) and glacial acetic acid (18 L) and the mixture heated to 90-100° C. and stirred for 3-4 h. The reaction mixture was concentrated to an oil diluted with water (20 L), adjusted to pH-7 with 5.5M aq. NaOH (10 L) and extracted with MTBE (20 L). The MTBE layer was washed with water (15 L) and brine (10 L) and concentrated to give an oil. To the oil was added isopropyl borate (B(OiPr)$_3$) (6058.6 g) and THF (40 L) and the mixture cooled to −75 to −60° C. n-BuLi (2.5M, 12.9 L) was added dropwise at −70 to −60° C. and stirred overnight. The reaction was warmed to −10 to 0° C. and water (24 L was added) followed by conc. HCl (4 L) and the mixture stirred for 10 min and separated. The aqueous phase was adjusted to pH5-6 with 1N NaOH solution and extracted with EtOAc (2×10 L). The combined organics were washed with NaHCO$_3$ solution and brine and concentrated to give an oil. This oil was diluted with heptanes (20 L) and cooled to 0-10° C. to give a white solid that was isolated by filtration to give the title compound (4530 g, 71% th).

HPLC RT=6.53 min, 98.7%,

Column: 150 mm×4.6 mm ID, 3.5 μm Agilent Zorbax Bonus RP

Flow Rate: 1.0 mL/min.

Temp.: 40° C.

Detection wavelength: 220 nm

Solvents: A: 0.05% v/v solution of trifluoroacetic acid in water

B: 0.05% v/v solution of trifluoroacetic acid in acetonitrile

| Gradient: | | |
|---|---|---|
| Time (min) | A % | B % |
| 0.01 | 90 | 10 |
| 15.0 | 5 | 95 |
| 18.0 | 5 | 95 |
| 18.1 | 90 | 10 |

Intermediate 48. Methyl 4-((R)-3-(2-(1,8-naphthyridin-2-yl)ethyl)pyrrolidin-1-yl)-3-(3-(3,5-dimethyl-1H-pyrazol-1-yl)phenyl)butanoate. Stage 6

To a reactor was charged toluene (25 kg), (R,E)-methyl 4-(3-(2-(1,8-naphthyridin-2-yl)ethyl)pyrrolidin-1-yl)but-2-enoate (Intermediate 47 in toluene (42.15 kg, 13.4% assay, 5.6 kg (1 wt) active), 17% w/w aq. KOH solution (10 kg), (3-(3,5-dimethyl-1H-pyrazol-1-yl)phenyl)boronic acid (Intermediate 9) (8.4 kg), chloro-(1,5-cyclooctadiene)rhodium (I) dimer (0.433 kg) and (R)-(+)-2,2'-bis(diphenylphosphino)-1,1'-binaphthyl (1.3 kg). The reactor was purged with nitrogen, heated to 75-85° C. and stirred under nitrogen for about 5 h. The mixture was distilled under reduced pressure to 1-3 vol and cooled to 20-30° C. The mixture was treated with DCM (166 kg) and water (57 kg), stirred and the aqueous phase discarded. The organic phase was acidified with 0.5N aq. HCl solution (141 kg), separated and the aqueous phase washed twice with DCM (45 and 43 kg). Ethyl acetate (57 kg) was added into the aqueous phase and the mixture neutralised to pH7-8 with 1N aq. NaOH (56 kg). The organic layer was collected and the aqueous layer was extracted twice with ethyl acetate (2×28 kg). The combined EtOAc extracts were washed with 25% aq. NaCl (32 kg) and distilled under reduced pressure to 1-2 vol. The mixture was diluted with MeOH (25 kg) and distilled under reduced pressure to 1-2 vol. The residue was diluted with MeOH (29 kg) to give a solution of the title compound in MeOH (~9:1 dr, 49.4 kg, 9.0% assay, 51% th yield).

HPLC RT=11.68 min, 90.9%,

Column: 150 mm×4.6 mm ID, 3.5 ?inn Agilent Zorbax SB-C8

Flow Rate: 1.0 mL/min.

Temp.: 40° C.

Detection wavelength: 210 nm

Solvents: A: 0.05% v/v solution of trifluoroacetic acid in water

B: 0.05% v/v solution of trifluoroacetic acid in acetonitrile

| Gradient: | | |
|---|---|---|
| Time (min) | A % | B % |
| 0.0 | 95 | 5 |
| 15.0 | 30 | 70 |
| 18.0 | 5 | 95 |
| 20.0 | 5 | 95 |
| 20.1 | 95 | 5 |

Chiral HPLC RT=10.27 min, 90.0%,

Column: 250 mm×4.6 mm ID, 5 μm CHIRALPAK AD-H

Flow Rate: 1.0 mL/min.

Temp.: 40° C.

Detection wavelength: 248 nm
Solvents: A: 0.1% v/v solution of diethyl amine in n-hexane
B: 0.1% v/v solution of diethylamine in ethanol

| Gradient: | | |
|---|---|---|
| Time (min) | A % | B % |
| 0.01 | 80 | 20 |
| 40 | 80 | 20 |

Intermediate 49. Methyl 3-(3-(3,5-dimethyl-1H-pyrazol-1-yl)phenyl)-4-((R)-3-(2-(5,6,7,8-tetra-hydro-1,8-naphthyridin-2-yl)ethyl)pyrrolidin-1-yl) butanoate. Stacie 7

To a hydrogenation vessel was added a solution of methyl 4-((R)-3-(2-(1,8-naphthyridin-2-yl)ethyl)pyrrolidin-1-yl)-3-(3-(3,5-dimethyl-1H-pyrazol-1-yl)phenyl)butanoate (Intermediate 48) in MeOH (49.4 kg, 9.0% assay, 4.4 kg (1 wt) active) and Rh/C (1.1 kg) and the vessel was purged with nitrogen. The reaction was placed under hydrogen atmosphere (0.3 MPa) and stirred at 35-45° C. for about 26 h. The reaction atmosphere was replaced with nitrogen and cooled to 20-30° C. The reaction mixture was filtered and the solid residue washed with MeOH (3×13 kg). The combined filtrates were concentrated under reduced pressure to 100-200 L, filtered, washing with MeOH (20 kg) and further concentrated to give a solution of the title compound in methanol (27.2 kg).

HPLC RT=23.63 min, 85.4%,
Column: 150 mm×4.6 mm ID, 2.5 μm Waters XSELECT HSS C18
Flow Rate: 0.6 mL/min.
Temp.: 40° C.
Detection wavelength: 245 nm
Solvents: A: 0.2% v/v solution of trifluoroacetic acid in water
B: 0.2% v/v solution of trifluoroacetic acid in acetonitrile

| Gradient: | | |
|---|---|---|
| Time (min) | A % | B % |
| 0.0 | 90 | 10 |
| 25.0 | 50 | 50 |
| 35.0 | 5 | 95 |
| 40.0 | 5 | 95 |
| 40.1 | 90 | 10 |

Intermediate 50. 3-(3-(3,5-Dimethyl-1H-pyrazol-1-yl)phenyl)-4-((R)-3-(2-(5,6,7,8-tetrahydro-1,8-naph-thyridin-2-yl)ethyl)pyrrolidin-1-yl)butanoic acid. Stage 8

The solution of methyl 3-(3-(3,5-dimethyl-1H-pyrazol-1-yl)phenyl)-4-((R)-3-(2-(5,6,7,8-tetrahydro-1,8-naphthyri-din-2-yl)ethyl)pyrrolidin-1-yl)butanoate (Intermediate 50) in methanol (27.2 kg, 4.4 kg (1 wt) active) obtained in stage 7 was distilled to 1-2 vol. under reduced pressure and diluted with MeOH (26 kg). To this solution was added silica thiol (0.5 kg) and the pH of the mixture was adjusted to ~1 with HCl/MeOH (3.5M, 8 kg). The mixture was stirred at 60-70° C. for 10 h, cooled to 20-30° C. and filtered. The filter cake was washed with methanol (4 kg then 2×5 kg). The filtrate was concentrated to ~6-8 vol., diluted with MeOH (4 kg) and silica thiol (0.5 kg) was charged. After adjusting the pH to ~1 with HCl/MeOH (3.5M, 2 kg), the solution was stirred at 60-70° C. for 10 h. The mixture was cooled to 20-30° C., filtered and the filter cake was washed with methanol (5 kg then 2×4 kg) and the filtrate was concentrated to ~6-8 vol. at ≤45° C. under reduced pressure. The residue was diluted with MeOH (13 kg) and further concentrated to 1-2 vol at ≤45° C. under reduced pressure. The residue was diluted with MeOH (13 kg) and 2M aq. NaOH solution (2 2 kg) was added to give a mixture pH>14 that was stirred at 30-40° C. for 11 h before being diluted with MeOH (4 kg) and concentrated to 4-5 vol. at ≤45° C. under reduced pressure. The pH was adjusted to 8-9 with HCl (3M aq., 6 kg) and the mixture was treated with DCM (20 kg) and the pH of the aqueous phase adjusted to pH 8-9 by the addition of NaOH (2M aq., 5.7 kg). The aqueous phase was extracted four times with DCM (2×30 kg, 31 kg, 30 kg). The combined organic phase was washed with a mixture of water (10 kg) and HCl (3M aq., 6 kg) and the aqueous phase extracted twice with DCM (30 kg, 31 kg). The combined organic phases were concentrated to 1-2 vol. at ≤40° C. under reduced pressure and diluted with DCM (10 kg) to give the solution of the title compound in DCM (16.8 kg, 22.4% assay, 87% th over two steps).

HPLC RT=20.69 min, 87.8%,
Column: 150 mm×4.6 mm ID, 2.5 μm Waters XSELECT HSS C18
Flow Rate: 0.6 mL/min
Temp.: 40° C.
Detection wavelength: 245 nm
Solvents: A: 0.2% v/v solution of trifluoroacetic acid in water
B: 0.2% v/v solution of trifluoroacetic acid in acetonitrile

| Gradient: | | |
|---|---|---|
| Time (min) | A % | B % |
| 0.0 | 90 | 10 |
| 25.0 | 50 | 50 |
| 35.0 | 5 | 95 |
| 40.0 | 5 | 95 |
| 40.1 | 90 | 10 |

Chiral Separation 3-(3-(3,5-Dimethyl-1H-pyrazol-1-yl)phenyl)-4-((R)-3-(2-(5,6,7,8-tetrahydro-1,8-naphthyridin-2-yl)ethyl)pyrroli-din-1-yl)butanoic acid (Intermediate 50) solution in DCM prepared from stage 8 was concentrated under reduced pressure and MeOH was added to prepare 100 mg/mL solution that was filtered. The solution was applied on Supercritical Fluid Chromatography (SFC) for chiral separation. The SFC separation parameters were as follows:

| | |
|---|---|
| Preparative | CHIRALPAK OJ, 250*50 mm (I.D.), |
| Mobile phase A | Supercritical $CO_2$ |
| Mobile phase B | MeOH (0.1% DEA, v/v) |
| A:B ratio | 70:30 |
| Flow rate | 250 g/min |
| Detection | 220 nm |
| Column | 40° C. |
| Back Pressure | 100.0 bar |

| | |
|---|---|
| Injection volume | ~0.5 g |
| Injection interval | 4.5 min |
| Desired product | The second main peak |

The fractions containing the desired isomer were concentrated at 30° C. under reduced pressure to give (S)-3-(3-(3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl) butanoic acid (Example 1) as a solution in MeOH/diethylamine (12.2 kg, 22.9% assay, 74% th).

Example 9: (S)-3-(3-(3,5-Dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid, hydrochloride salt. Stacie 9

The solution of (S)-3-(3-(3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid (Example 1) in methanol (12.1 kg, 22.9% assay, 2.8 kg (1 wt) active) was diluted with DCM (3 kg) and concentrated to 1-3 vol at ≤35° C. under reduced pressure. The resulting solution was diluted with DCM (36 kg) and washed with 33% ammonium chloride aqueous solution twice (14 kg×2) until residual diethylamine was <0.5%. The organic phase was diluted with DCM (4 kg), dried over anhydrous $Na_2SO_4$ (2.8 kg), filtered and the cake washed with DCM (5 kg×3). The combined filtrates were concentrated to 1-3 vol. at ≤55° C. under reduced pressure. Acetonitrile (6 kg) was charged and the mixture distilled to 1-3 vol. at ≤45° C. under reduced pressure to remove residual methanol. The residue was diluted with acetonitrile (20 kg), and then HCl aqueous (3M, 1.9 kg) was charged. After being stirred for 40 min. at 35° C., the mixture was filtered into a crystallisation vessel through a cartridge filter, washing with MeCN (3 kg). The solution was distilled to ~4 vol at ≤45° C. under reduced pressure to afford the solution of the title compound in acetonitrile. Four portions of acetonitrile (8 kg×2, 14 kg, 19 kg) was added and distilled to 3-5 vol. at ≤45° C. under reduced pressure to remove residual water. Acetonitrile (17 kg) was charged to dilute the crude product and the resulting solution was stirred at 50-55° C. for 16 hours under nitrogen protection. The batch was cooled to 0-5° C. over 5 h and stirred at 0-5° C. for ~4 h under nitrogen. The batch was heated to 50-55° C. and stirred at 50-55° C. for ~4 h under nitrogen. The batch was cooled to −10-−8° C. over 6 h and stirred at −10-−8° C. for ~23 h under nitrogen. After the form was confirmed by XRPD and DSC, the suspension was filtered and the filter cake was washed with acetonitrile (6 kg) under nitrogen. The wet solid was dried at 20-35° C. for 20 h under reduced pressure, then the temperature was increased to 45-55° C. for an additional 50 h. After the material was sieved, it was dried at 45-55° C. for additional 20 h to give the title compound (1.966 kg, 66% th).

Mpt: 197-202° C.

$^1$H NMR (DMSO-$d_6$; 500 MHz) δ ppm 13-11 (br. s., 1H), 7.43-7.51 (m, 2H), 7.35-7.41 (m, 2H), 7.18 (d, J=7.2 Hz, 1H), 7.02 (br. s., 1H), 6.35 (d, J=7.3 Hz, 1H), 6.07 (s, 1H), 3.54-3.64 (m, 1H), 3.47 (dd, J=12.8, 7.2 Hz, 1H), 3.25-3.37 (m, 4H), 3.18 (br. s., 1H), 3.05-3.13 (m, 1H), 3.00 (dd, J=16.3, 5.6 Hz, 1H), 2.86 (t, J=9.5 Hz, 1H), 2.56-2.68 (m, 3H), 2.41-2.49 (m, 2H), 2.30 (s, 3H), 2.14-2.27 (m, 1H), 2.18 (s, 3H), 1.98-2.10 (m, 1H), 1.72-1.81 (m, 1H), 1.61-1.72 (m, 2H), 1.56 (dq, J=12.7, 8.2 Hz, 1H).

HPLC RT=20.56 min, 99.4%,
Column: 150 mm×4.6 mm ID, 2.5 μm Waters XSELECT HSS C18
Flow Rate: 0.6 mL/min.
Temp.: 40° C.
Detection wavelength: 245 nm
Solvents: A: 0.2% v/v solution of trifluoroacetic acid in water
B: 0.2% v/v solution of trifluoroacetic acid in acetonitrile

| Gradient: | | |
|---|---|---|
| Time (min) | A % | B % |
| 0 | 90 | 10 |
| 25 | 50 | 50 |
| 35 | 5 | 95 |
| 40 | 5 | 95 |
| 40.1 | 90 | 10 |
| 52 | Stop | |

Chiral HPLC RT=34.8 min, 100% a/a,
Column: 250 mm×4.6 mm ID, 5 μm CHIRALPAK AS-H
Flow Rate: 1.0 mL/min.
Temp.: 40° C.
Detection wavelength: 319 nm
Solvents: A: 0.2% v/v solution of triethylamine in n-heptane
B: 0.2% v/v solution of triethylamine in ethanol

| Gradient: | | |
|---|---|---|
| Time (min) | A % | B % |
| 0.01 | 92 | 8 |
| 100 | stop | |

Determination of Absolute Configuration of Example 1

Reduction of Example 1 and its Diastereoisomer

Intermediate 33: Isomer 1. 3-(3-(3,5-Dimethyl-1H-pyrazol-1-yl)phenyl)-4-((R)-3-(2-(5,6,7,8-tetrahydro-1,8-naphthyridin-2-yl)ethyl)pyrrolidin-1-yl)butan-1-ol A suspension of 3-(3-(3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid Hydrochloride (Example 8, which is the hydrochloride salt of Example 1) (238 mg, 0.454 mmol) in THF (5 mL) was treated at 20° C. with LiAlH$_4$ solution in ether (1M, 1.5 mL) and the mixture was stirred under nitrogen for 1.5 h. LCMS indicated completion of the reaction. The reaction was quenched by addition of 2M NaOH solution (0.8 mL) and ethyl acetate. The mixture was partitioned and the organic solution was washed with NaHCO$_3$ solution, brine, dried (MgSO$_4$) and evaporated under reduced pressure. The residue was dissolved in 1:1 MeOH-DMSO (2 mL) and purified by MDAP (Method A) collecting fractions with RT=6.6-9.4 min. The solvent was removed under reduced pressure to give the title compound (157 mg, 73%) as a colourless oil: NMR δ (DMSO-$d_6$, 600 MHz) δ 7.40-7.36 (m, 1H), 7.28-7.26 (m, 1H), 7.28-7.25 (m, 1H), 7.20 (d, J=7.7 Hz, 1H), 6.99 (d, J=7.3 Hz, 1H), 6.22 (d, J=7.2 Hz, 1H), 6.20 (br. s., 1H), 6.05 (s, 1H), 3.32-3.28 (m, 1H), 3.25-3.21 (m, 1H), 3.24-3.18 (m, 2H), 2.97-2.90 (m, 1H), 2.71 (t, J=8.2 Hz, 1H), 2.64 (dd, J=11.8, 7.8 Hz, 1H), 2.59 (t, J=6.2 Hz, 2H), 2.57-2.53 (m, 1H), 2.54-2.50 (m, 1H), 2.39-2.34 (m, 2H), 2.37-2.32 (m, 1H), 2.26 (s, 3H), 2.17 (s, 3H), 2.07-2.01 (m, 1H), 1.94 (dd, J=13.1, 7.4 Hz, 1H), 1.97-1.88 (m, 1H), 1.87-1.79 (m, 1H), 1.74 (dt, J=11.5, 6.0 Hz, 2H), 1.67-1.59 (m, 1H), 1.60-1.53 (m, 2H), 1.31-1.24 (m, 1H); $[\alpha]_D^{20}$=+17 (c=1.56 in CHCl$_3$).

Intermediate 34. 4-((R)-3-(2-(1,8-Naphthyridin-2-yl)ethyl)pyrrolidin-1-yl)-3-(3-(3,5-dimethyl-1H-pyrazol-1-yl)phenyl)butan-1-ol A solution of tert-butyl 4-((R)-3-(2-(1,8-naphthyridin-2-yl)ethyl)pyrrolidin-1-yl)-3-(3-(3,5-dimethylpyrazol-1-yl)phenyl)butanoate (Intermediate 13, isomer 2) (155 mg, 0.287 mmol) in 2-Me-THF (3 mL) was cooled in ice to 5° C. and then treated cautiously with Lithium aluminium hydride solution in THF (1M, 1.5 mL). The mixture was stirred under nitrogen for 2 h, LCMS indicated completion. The reaction was quenched by addition of 2M NaOH solution (0.3 mL) and the mixture was stirred for 0.5 h. Ethyl acetate, and solid sodium sulphate were added and the mixture was stirred for 5 min, filtered, washed the solid with ethyl acetate, and evaporated under reduced pressure. The residue was dissolved in DMSO-MeOH (1:1, 2 mL) and purified by MDAP (Method A) collecting fraction with RT=5.09 min. The solvent was evaporated under reduced pressure, the residue was dissolved in MeOH and re-evaporated under reduced pressure to give two impure fractions. The two fractions were combined (31 mg) and re-purified by MDAP 25 min rum (high pH) collecting fraction with RT=6.41 min, m/z 470 evaporated under reduced pressure to give the title compound (16.4 mg, 12%) as a colourless oil: LCMS (Method A) RT=0.94 min, 91%, ES+ve m/z 470 (M+H)$^+$; $[\alpha]_D^{20}$ 213=-14 (c=1.64 in CHCl$_3$).

Intermediate 33 Isomer 2. 3-(3-(3,5-Dimethyl-1H-pyrazol-1-yl)phenyl)-4-((R)-3-(2-(5,6,7,8-tetrahydro-1,8-naphthyridin-2-yl)ethyl)pyrrolidin-1-yl)butan-1-ol A solution of 4-((R)-3-(2-(1,8-naphthyridin-2-yl)ethyl)pyrrolidin-1-yl)-3-(3-(3,5-dimethyl-1H-pyrazol-1-yl)phenyl)butan-1-ol (Intermediate 34) (8 mg, 0.02 mmol) in ethanol (5 mL) was hydrogenated over 5% Rh/C wet catalyst (5 mg) over 2.5 days. The reaction mixture was filtered through celite and the catalyst was washed with ethanol. The filtrate and washings were evaporated under reduced pressure to give the title compound (7 mg, 87%) as a colourless oil: NMR δ (DMSO-d6, 600 MHz): 7.37 (t, J=7.8 Hz, 1H), 7.26-7.28 (m, 1H), 7.24-7.27 (m, 1H), 7.20 (d, J=7.7 Hz, 1H), 6.99 (d, J=7.3 Hz, 1H), 6.21 (d, J=7.2 Hz, 1H), 6.19 (br. s., 1H), 6.04 (s, 1H), 4.61 (br. s., 1H), 3.27-3.30 (m, 1H), 3.21-3.23 (m, 2H), 3.19-3.25 (m, 1H), 2.90-2.98 (m, 1H), 2.68 (t, J=8.1 Hz, 1H), 2.57-2.61 (m, 2H), 2.56-2.61 (m, 2H), 2.51-2.56 (m, 1H), 2.35-2.41 (m, 1H), 2.32-2.39 (m, 2H), 2.26 (s, 3H), 2.17 (s, 3H), 2.03 (dd, J=8.5, 7.1 Hz, 1H), 1.88-1.99 (m, 2H), 1.78-1.87 (m, 1H), 1.73 (quin, J=5.9 Hz, 2H), 1.60-1.66 (m, 2H), 1.51-1.58 (m, 2H), 1.24-1.30 (m, 1H); $[\alpha]_D^{20}$=-19 (c=0.689 in CHCl$_3$).

Manufacture of Intermediate 39 Isomer 1 and Isomer 2

Intermediate 35. tert-Butyl 2-(3-(3,5-dimethyl-1H-pyrazol-1-yl)phenyl)acetate

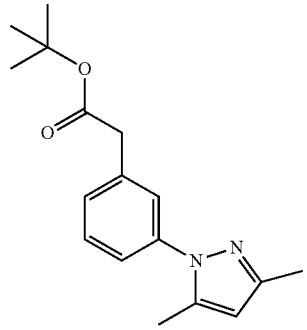 [SMILES: Cc1cc(C)n(-c2cccc(CC(=O)OC(C)(C)C)c2)n1]

A mixture of (3-(3,5-dimethyl-1H-pyrazol-1-yl)phenyl)boronic acid (Intermediate 9) (10.8 g, 50 mmol), tert-butyl 2-bromoacetate (14.6 g, 75 mmol), tri-o-tolylphosphine (1.5 g, 4.93 mmol), Pd(OAc)$_2$ (700 mg, 3.12 mmol), powdered tripotassium phosphate (42.5 g, 200 mmol) and tetrahydrofuran (100 mL) was degassed under nitrogen/vacuum cycles and was heated at reflux for 16 h. LCMS analysis shows ~70% conversion. Further palladium acetate (300 mg) and tert-butyl 2-bromoacetate (3 g) were added and the mixture was refluxed for 6 h. LCMS shows no starting material and the presence of product. The mixture was partitioned between water (200 mL) and EtOAc (2×200 mL) and the dried (MgSO$_4$). The organic phase was evaporated and the residue was purified by chromatography on a silica cartridge (330 g) eluting with 0-40% ethyl acetate-cyclohexane (15CV) to give the title compound (10.4 g, 72%) as a yellow oil: LCMS (Method C) RT=1.18 min, ES+ve m/z 287 (M+H)$^+$.

Intermediate 36. 2-(3-(3,5-Dimethyl-1H-pyrazol-1-yl)phenyl)acetate

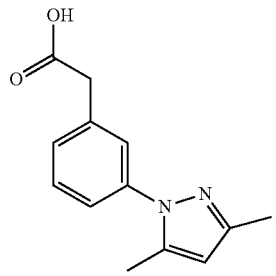 [SMILES: Cc1cc(C)n(-c2cccc(CC(=O)O)c2)n1]

A solution of tert-butyl 2-(3-(3,5-dimethyl-1H-pyrazol-1-yl)phenyl)acetate (Intermediate 35) (10 g, 28 mmol) in dichloromethane (10 mL) was treated slowly with TFA (20 mL, 260 mmol) and stirred at room temperature for 2 h. LCMS analysis showed completion of the reaction. The solution was evaporated under reduced pressure and the residue was dissolved in 2N NaOH (100 mL) and washed with diethyl ether (2×100 mL). The aqueous phase was acidified with 2N HCl and the cooled suspension was extracted with EtOAc (2×150 mL). The organic solution was dried (MgSO$_4$) and evaporated. The residue (~7 g) was triturated with diethyl ether (40 mL) and collected by filtration to give the title compound (5.2 g, 81%) as a beige solid: LCMS (Method C) RT=0.76 min, 100%, ES+ve m/z 231 (M+H)$^+$; NMR δ (CDCl$_3$, 400 MHz) 7.51-7.44 (1H, m), 7.41-7.30 (3H, m), 6.08 (1H, s), 3.70 (2H, s), 2.29 (3H, s), 2.26 (3H, s).

Intermediate 37. Methyl 2-(3-(3,5-dimethyl-1H-pyrazol-1-yl)phenyl)acetate

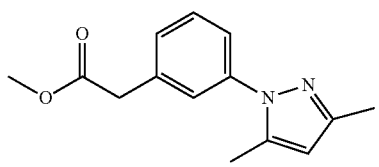

A solution of 2-(3-(3,5-dimethyl-1H-pyrazol-1-yl)phenyl)acetic acid (Intermediate 36) (460 mg, 2 mmol) was dissolved in MeOH (70 mL) and treated with hydrogen chloride solution in cyclopentyl methyl ether (3M, 10 mL) and the mixture was heated to reflux for 2 h. The mixture was concentrated under reduced pressure, and the residue was partitioned between ethyl acetate and sodium bicarbonate. The organic phase was washed with brine, dried over MgSO$_4$ and evaporated under reduced pressure. The residue was purified by chromatography on a silica cartridge (20 g) eluting with a gradient of 0-25% ethyl acetate-cyclohexane over 20 min. Appropriate fractions containing the major component were combined and evaporated to give the title compound (251 mg, 51%) as a colourless oil: NMR δ (CDCl$_3$) 7.43-7.37 (2H, m), 7.33 (1H, br d, J 8 Hz), 7.29-7.24 (1H, m obscured by CHCl$_3$), 5.99 (1H, s), 3.70 (3H, s), 3.68 (2H, s), 2.31 (3H, s) and 2.30 (3H, s).

Intermediate 38. 4-tert-Butyl 1-methyl 2-(3-(3,5-dimethyl-1H-pyrazol-1-yl)phenyl)succinate

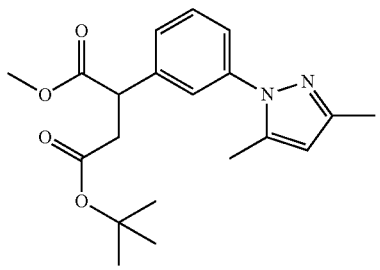

A solution of lithium hexamethyldisilazide in THF (1M, 1.85 mL) was cooled to −78° C. and treated with a solution of methyl 2-(3-(3,5-dimethyl-1H-pyrazol-1-yl)phenyl)acetate (Intermediate 37) (453 mg, 1.85 mmol) in THF (2 mL). After 5 min the reaction mixture was treated with tert-butyl 2-bromoacetate (0.82 mL, 5.6 mmol) in THF (2 mL) and after 30 min at −78° C. the mixture was allowed to warm to room temperature. The mixture was stirred for 2.5 h and then was quenched with aqueous HCl solution (0.2 M, 10 mL) and extracted with ethyl acetate. The organic solution was washed with aqueous NaHCO$_3$ solution, 0.2M HCl, brine, dried (MgSO$_4$) and evaporated under reduced pressure. The residue was purified by chromatography on a 50 g silica cartridge eluting with 0-25% EtOAc-cyclohexane. The fractions containing the main peak were combined and evaporated under reduced pressure to give a colourless oil (780 mg), which was further purified by chromatography on a 70 g silica cartridge eluting with 0-50% TBME-cyclohexane to give the title compound (479 mg, 72%) as a colourless oil: NMR δ (CDCl$_3$) 7.43-7.33 (3H, m), 7.29-7.25 (1H, m), 6.00 (1H, s), 4.09 (1H, dd, J 10.0, 5.5 Hz), 3.69 (3H, s), 3.13 (1H, dd, J 16.7, 10.0 Hz), 2.64 (1H, dd, J 16.7, 5.5 Hz), 2.30 (6H, s), 1.42 (9H, s). The two enantiomers of this compound were resolved by preparative chiral HPLC on a Chiralcel OD-H Column (30 mm×250 mm) eluting with 5% IPA-hexane, flow rate=20 mL/min to give Isomer 1 (267 mg) as a colourless oil: [α]$_D^{22}$+81 (c=1.028 in CHCl$_3$); Analytical chiral HPLC on Chiralcel OJ-H Column (4.6 mm id×250 mm) RT=7.75 min, 99.3% (contains the other enantiomer, RT=9.35 min, 0.7%), and Isomer 2 (230 mg) as a colourless oil: [α]$_D^{22}$-82 (c=1.016 in CHCl$_3$); Analytical chiral HPLC RT=9.35 min, 98.6% (contains the other enantiomer, RT=7.75 min, 1.4%).

Intermediate 39 Isomer 1. 4-(tert-Butoxy)-2-(3-(3,5-dimethyl-1H-pyrazol-1-yl)phenyl)-4-oxobutanoic acid

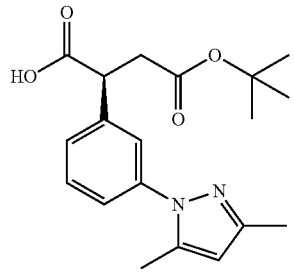 [SMILES: Cc1cc(C)n(-c2cccc([C@H](CC(=O)OC(C)(C)C)C(=O)O)c2)n1]

A solution of 4-tert-butyl 1-methyl 2-(3-(3,5-dimethyl-1H-pyrazol-1-yl)phenyl)succinate Isomer 1 (Intermediate 38, Isomer 1) (257 mg, 0.72 mmol) was dissolved in THF (2 mL) and cooled to 0° C. (ice-cooling) before 30% hydrogen peroxide (0.366 mL, 3.6 mmol) and 1M LiOH solution in water (1M, 2.15 mL) were added. After standing in the fridge overnight the reaction mixture was treated with aqueous sodium metabisulfite solution (1M, 3 mL) and then acidified to pH 1 with 2M HCl solution. The reaction mixture was extracted three times with ethyl acetate and the organic solution was dried over MgSO$_4$. The solution was evaporated under reduced pressure and the residual white foam was purified by MDAP (Method C). The appropriate fractions were evaporated under reduced pressure to give the title compound (140 mg, 57%) as a colourless oil: $^1$H NMR δ (400 MHz; CDCl$_3$) 7.38-7.32 (2H, m), 7.30-7.24 (2H, m), 5.98 (1H, s), 4.05 (1H, dd, J 9.5, 6 Hz), 3.09 (1H, dd, J 16.5, 9.5 Hz), 2.63 (1H, dd, J 16.5, 6 Hz), 2.31 (3H, s), 2.24 (3H, s), 1.38 (9H, s). [α]$_D^{20}$+42 (c=1.037 in CHCl$_3$).

Intermediate 39 Isomer 2. 4-(tert-Butoxy)-2-(3-(3,5-dimethyl-1H-pyrazol-1-yl)phenyl)-4-oxobutanoic acid

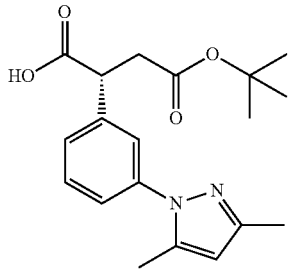 [SMILES: Cc1cc(C)n(-c2cccc([C@@H](CC(=O)OC(C)(C)C)C(=O)O)c2)n1]

A solution of 4-tert-butyl 1-methyl 2-(3-(3,5-dimethyl-1H-pyrazol-1-yl)phenyl)succinate Isomer 2 (Intermediate 38, Isomer 2) (220 mg, 0.61 mmol) was dissolved in 2-Me-THF (5 mL) and cooled to 0° C. (ice-cooling) before 30% hydrogen peroxide (0.313 mL, 3.1 mmol) and 0.2M LiOH solution in water (0.2M, 9.21 mL, 1.84 mmol) was added. LCMS indicated that the reaction went to completion after 6 days. The reaction mixture was treated with sodium thiosulfate solution (1M, 3 mL) and sodium bicarbonate solution (0.5M, 8 mL) and the mixture (pH 8) was stirred for 10 min, and then acidified to pH 1 with 6M HCl solution. The reaction mixture was extracted three times with ethyl acetate and the organic solution was dried over MgSO$_4$. Evaporation under reduced pressure gave a white solid which was purified by MDAP (Method C). Evaporation of the appropriate fractions under reduced pressure gave the title compound (105 mg, 50%) as a colourless oil: $^1$H NMR δ (400 MHz; CDCl$_3$) 7.38-7.32 (2H, m), 7.30-7.22 (2H, m), 5.99 (1H, s), 4.05 (1H, dd, J 9.5, 6 Hz), 3.09 (1H, dd, J 16.5, 9.5 Hz), 2.63 (1H, dd, J 16.5, 6 Hz), 2.31 (3H, s), 2.24 (3H, s), 1.38 (9H, s). $[α]_D^{20}$-41 (c=1.482 in CHCl$_3$).

Determination of Absolute Configuration of Intermediate 39 Isomer 1 as (S) (Evans Method)

Intermediate 40. (S)-(+)-4-Benzyl-3-(2-(3-(3,5-dimethyl-1H-pyrazol-1-yl)phenyl)acetyl)oxazolidin-2-one

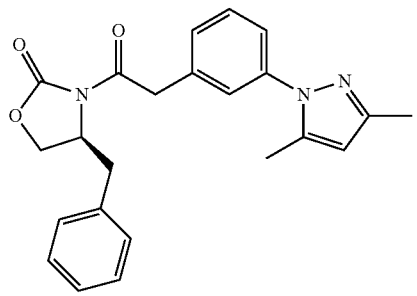 [SMILES: Cc1cc(C)n(-c2cccc(CC(=O)N3C(=O)OC[C@@H]3Cc3ccccc3)c2)n1]

2-(3-(3,5-Dimethyl-1H-pyrazol-1-yl)phenyl)acetic acid (Intermediate 36) (2.3 g, 9.99 mmol) was dissolved in THF (70 mL) and treated with DIPEA (2.268 mL, 12.99 mmol). To the stirred solution was added pivaloyl chloride (1.229 mL, 9.99 mmol) via syringe under nitrogen. The mixture was stirred at 0° C. for 45 min, and then re-cooled to −78° C. which gave a white slurry.

In the meantime in a separate flask (S)-4-benzyloxazolidin-2-one (3.19 g, 17.98 mmol) was dissolved in THF (50 mL) and cooled to −78° C. while being stirred. To this solution was added n-BuLi 1.6M in hexanes (11.24 mL, 17.98 mmol) and the mixture was stirred at −78° C. for 0.5 h. The metalated oxazolidinone was added to the mixed anhydride using a cannula. The resulting slurry was stirred for 1 h at −78° C. and then allowed to warm to room temperature over the weekend.

The reaction mixture was quenched with an aqueous saturated ammonium chloride solution (40 mL), diluted with water (10 mL) and extracted with ethyl acetate. The organic phase was washed with brine, dried (MgSO$_4$), filtered and concentrated in vacuo. The residual oil was dissolved in DCM and purified by chromatography on a 100 g silica cartridge eluting with a gradient of 0-50% ethyl acetate in cyclohexane over 40 min. The fractions containing the major component were combined and concentrated in vacuo to yield the title compound (2.1 g, 54%) as a colourless oil: $^1$H NMR δ (600 MHz, DMSO-d$_6$) 7.48-7.44 (m, 1H), 7.43 (s, 1H), 7.41-7.38 (m, 1H), 7.29 (d, J=8.3 Hz, 1H), 7.28-7.25 (m, 2H), 7.25-7.21 (m, 1H), 7.17-7.13 (m, 2H), 6.07 (s, 1H), 4.69 (tt, J=7.8, 3.0 Hz, 1H), 4.36 (t, J=8.5 Hz, 1H), 4.36-4.32 (m, 1H), 4.26-4.20 (m, 1H), 4.23-4.18 (m, 1H), 3.03-2.97 (m, 1H), 2.95-2.90 (m, 1H), 2.29 (s, 3H), 2.18 (s, 3H); $[α]_D^{20}$=+49 (c 1.64 in CHCl$_3$).

Intermediate 41 (S)-tert-Butyl 4-((S)-4-benzyl-2-oxooxazolidin-3-yl)-3-(3-(3,5-dimethyl-1H-pyrazol-1-yl)phenyl)-4-oxobutanoate, and Intermediate 42. (R)-tert-butyl 4-((S)-4-benzyl-2-oxooxazolidin-3-yl)-3-(3-(3,5-dimethyl-1H-pyrazol-1-yl)phenyl)-4-oxobutanoate

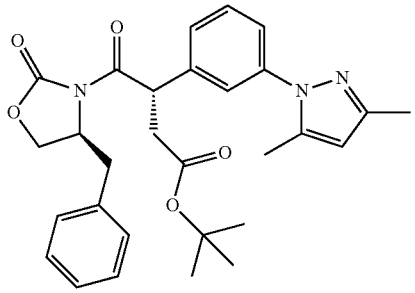 [SMILES: Cc1cc(C)n(-c2cccc([C@H](CC(=O)OC(C)(C)C)C(=O)N3C(=O)OC[C@@H]3Cc3ccccc3)c2)n1]

A solution of lithium hexamethyldisilazide in THF (1M, 5.7 mL) was added to a solution of (S)-4-benzyl-3-(2-(3-(3,5-dimethyl-1H-pyrazol-1-yl)phenyl)acetyl)oxazolidin-2-one (Intermediate 40) (2.0 g, 5.14 mmol) in THF (10 mL) at −78° C. and the mixture was stirred at −78° C. for 60 min before tert-butyl 2-bromoacetate (2.3 mL, 15 mmol) was added. The mixture was stirred at −78° C. for 3 h and then allowed to warm to room temperature and stirred for 2 days before it was quenched by addition of aqueous sat. ammonium chloride solution. The mixture was partitioned with ethyl acetate, the organic phase was separated, washed with brine (twice), dried over MgSO$_4$ and evaporated under reduced pressure. The residue was purified by chromatography on a silica (100 g) cartridge eluting with 0-50% ethyl acetate-cyclohexane over 1 h to give the product (1.2 g, 46%) as a yellow oil which was a mixture of two diastereoisomers: LCMS (Method C) RT=1.32 min, 11%, ES+ve m/z 504 and RT=1.36 min, 53%, ES+ve m/z 504 (M+H)+. A portion of the diastereoisomeric mixture of the expected product (200 mg) was further purified by MDAP (Method C) collecting the major fraction with RT=9.56 min to give (S)-tert-butyl 4-((S)-4-benzyl-2-oxooxazolidin-3-yl)-3-(3-(3,5-dimethyl-1H-pyrazol-1-yl)phenyl)-4-oxobutanoate (Intermediate 41) (69 mg) as a colourless oil: LCMS (Method C) RT=1.36 min, ES+ve m/z 504 (M+H)+; $^1$H NMR δ (400 MHz, CDCl$_3$) 7.47 (1H, br s), 7.43-7.28 (8H, m), 6.00 (1H, s), 5.56 (1H, dd, J 11, 4 Hz), 4.67-4.59 (1H, m), 4.15-4.06 (2H, m), 3.42-3.30 (2H, m), 2.83 (1H, dd, J 13, 10 Hz), 2.67 (1H, dd, J 17, 4 Hz), 2.32 (3H, s), 2.30 (3H, s), 1.46 (9H, s); $[α]_D^{20}$=+102 (c=1.20 in CHCl$_3$). The minor fraction from the MDAP purification with RT=9.2 min was evaporated under a stream of nitrogen in a blow-down unit to give (R)-tert-butyl 4-((S)-4-benzyl-2-oxooxazolidin-3-yl)-3-(3-(3,5-dimethyl-1H-pyrazol-1-yl)phenyl)-4-oxobutanoate (Intermediate 42) (7 mg): LCMS (Method C) RT=1.32 min, ES+ve m/z 504 (M+H)+; 1H NMR δ (400 MHz, CDCl$_3$) 7.51 (1H, br s), 7.46-7.38 (3H, m), 7.21-7.15 (3H, m), 6.99-6.94 (2H, m), 5.97 (1H, s), 5.46 (1H, dd, J 11, 4 Hz), 4.81-4.73 (1H, m), 4.24 (1H, t, J 8.5 Hz), 4.10 (1H, dd, J 9, 3 Hz), 3.33 (1H, dd, J 17, 11 Hz), 3.08 (1H, dd, J 13.5, 3 Hz), 2.66-2.59 (2H, m), 2.29 (3H, s), 2.28 (3H, s), 1.43 (9H, s); $[α]_D^{20}$=−37 (c=0.71 in CHCl$_3$).

Intermediate 39 Isomer 1 (S)-(+)-4-(tert-Butoxy)-2-(3-(3,5-dimethyl-1H-pyrazol-1-yl)phenyl)-4-oxobutanoic acid

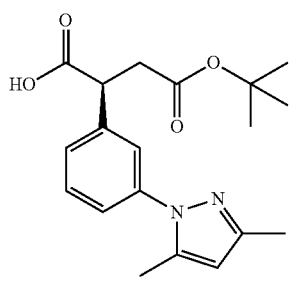

A solution of (S)-tert-butyl 4-((S)-4-benzyl-2-oxooxazolidin-3-yl)-3-(3-(3,5-dimethyl-1H-pyrazol-1-yl)phenyl)-4-oxobutanoate (Intermediate 41) (69 mg, 0.14 mmol) in THF (1 mL) was treated with 30% hydrogen peroxide (8.8 M, 0.078 mL, 0.68 mmol) at 4° C., followed by aqueous lithium hydroxide (1M, 0.411 mL) and the mixture was stirred in an ice-bath for 2 h. The reaction mixture was stood in the fridge overnight and then quenched by addition of aqueous sodium metabisulfite solution, followed after 10 min by addition of 2M HCl. After 2 h the mixture was extracted with ethyl acetate and the aqueous layer was extracted with more EtOAc. The combined organic solutions were washed with brine, dried (MgSO$_4$) and evaporated under reduced pressure. The residue was dissolved in DMSO (1 mL) and purified by MDAP (Method C) collecting the peak with RT=8.3-9.9 min, m/z 345. The appropriate fractions were evaporated in a stream of nitrogen in a blow-down unit to give the title compound (22 mg, 47%) as a colourless oil: $^1$H NMR δ (CDCl$_3$) 7.36-7.31 (2H, m), 7.28-7.23 (2H, m), 5.96 (1H, s), 4.04 (1H, dd, J 9.5, 6 Hz), 3.08 (1H, dd, J 16.5, 9.5 Hz), 2.62 (1H, dd, J 16.5, 6 Hz), 2.29 (3H, s), 2.23 (3H, s), 1.37 (9H, s); $[α]_D^{20}$=+65 (c=2.08 in CHCl$_3$).

Synthesis of Intermediate 46 and Intermediate 33 Isomer 1 and Showing they are the Same Isomer Intermediate 43. (S)-(+)-tert-Butyl 4-((R)-3-(2-(1,8-naphthyridin-2-yl)ethyl)pyrrolidin-1-yl)-3-(3-(3,5-dimethyl-1H-pyrazol-1-yl)phenyl)-4-oxobutanoate

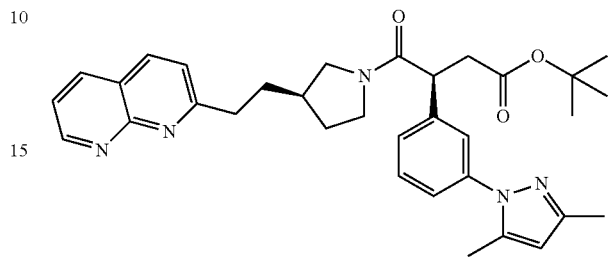

A solution of 4-tert-butyl 1-methyl 2-(3-(3,5-dimethyl-1H-pyrazol-1-yl)phenyl)succinate (Intermediate 39 Isomer 1) (107 mg, 0.31 mmol) in DCM (1 mL) was treated with N-[3-(dimethylamino)propyl]-N-ethylcarbodiimide hydrochloride (77 mg, 0.40 mmol) and N-hydroxybenztriazole hydrate (62 mg, 0.40 mmol). The reaction mixture was stirred for 10 min before a solution of (R)-2-(2-(pyrrolidin-3-yl)ethyl)-1,8-naphthyridine (Intermediate 3) (100 mg, 0.44 mmol) in DCM (3 mL) and N-Me-morpholine (0.102 mL, 0.93 mmol) was added. The mixture was stirred for 2 h at room temperature. The mixture was diluted with water and the phases were separated in a phase-separator frit, and the organic phase was evaporated under reduced pressure. The residue was purified by MDAP (Method C) collecting fractions with m/z 554. The solvent was removed under reduced pressure to give the title compound (160 mg, 93%) as a colourless oil: LCMS (Method C) RT=0.99 min, 98.5%, ES+ve m/z 554 (M+H)+; $[α]_D^{20}$=+41 (c=1.720 in CHCl$_3$); Analytical chiral HPLC Chiralcel OD-H (4.6 mm×250 mm) eluting with 10% EtOH-heptane containing 0.1% isopropylamine detecting at 235 nm, flow rate=1 mL/min, RT=30.4 min, 77.3% and RT=37.6 min, 22.7%.

Intermediate 44. (S)-tert-Butyl 3-(3-(3,5-dimethyl-1H-pyrazol-1-yl)phenyl)-4-oxo-4-((R)-3-(2-(5,6,7,8-tetrahydro-1,8-naphthyridin-2-yl)ethyl)pyrrolidin-1-yl)butanoate

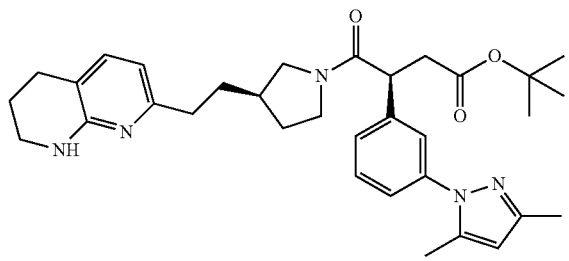 [SMILES: Cc1cc(C)n(-c2cccc([C@H](CC(=O)OC(C)(C)C)C(=O)N3CC[C@@H](CCc4ccc5c(n4)NCCC5)C3)c2)n1]

A solution of (S)-tert-butyl 4-((R)-3-(2-(1,8-naphthyridin-2-yl)ethyl)pyrrolidin-1-yl)-3-(3-(3,5-dimethyl-1H-pyrazol-1-yl)phenyl)-4-oxobutanoate (Intermediate 43) (107 mg, 0.19 mmol) in ethanol (20 mL) was hydrogenated over 5% Rh/C (28 mg) over 4 days. More catalyst (5 mg) was added and the mixture hydrogenated for another day. The catalyst was removed by filtration through celite and washed with ethanol. The combined filtrate and washings were concentrated under reduced pressure to give the title compound (101 mg, 94%): LCMS (Method C) RT=0.86 min, 98%, ES+ve m/z 558 (M+H)+.

Intermediate 45. (S)-(+)-3-(3-(3,5-Dimethyl-1H-pyrazol-1-yl)phenyl)-4-oxo-4-((R)-3-(2-(5,6,7,8-tetrahydro-1,8-naphthyridin-2-yl)ethyl)pyrrolidin-1-yl)butanoic acid

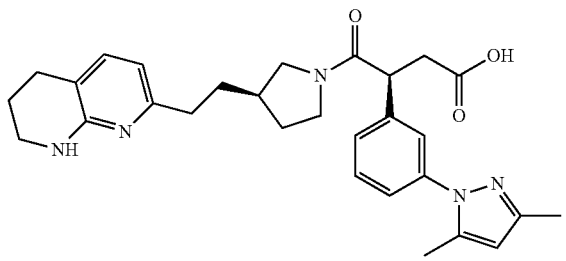 [SMILES: Cc1cc(C)n(-c2cccc([C@H](CC(=O)O)C(=O)N3CC[C@@H](CCc4ccc5c(n4)NCCC5)C3)c2)n1]

A solution of (S)-tert-butyl 3-(3-(3,5-dimethyl-1H-pyrazol-1-yl)phenyl)-4-oxo-4-((R)-3-(2-(5,6,7,8-tetrahydro-1,8-naphthyridin-2-yl)ethyl)pyrrolidin-1-yl)butanoate (Intermediate 44) (101 mg, 0.18 mmol) in CHCl₃ (5 mL) was treated with TFA (3 mL) at room temperature for 2 h. The reaction mixture was evaporated under reduced pressure and the residue was dissolved in DCM and re-evaporated under reduced pressure three times. The residue (200 mg) was dissolved in acetonitrile and passed down a SCX-2 cartridge (10 g) which was pre-conditioned with MeCN. The compound was washed with MeCN and eluted with 2M ammonia in MeOH. The ammoniacal fractions were evaporated under reduced pressure to give the title compound (80 mg, 88%) as a white foam: LCMS (Method A) RT=0.82 min, 90%, ES+ve m/z 502 (M+H)+; $[\alpha]_D^{20}$=+34 (c=0.88 in CHCl₃).

Intermediate 46. (0.5)-(+)-3-(3-(3,5-Dimethyl-1H-pyrazol-1-yl)phenyl)-4-((R)-(2-(5,6,7,8-tetrahydro-1,8-naphthyridin-2-yl)ethyl)pyrrolidin-1-yl)butan-1-ol

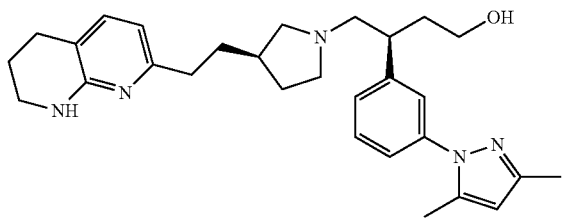 [SMILES: Cc1cc(C)n(-c2cccc([C@H](CCO)CN3CC[C@@H](CCc4ccc5c(n4)NCCC5)C3)c2)n1]

A solution of (S)-3-(3-(3,5-dimethyl-1H-pyrazol-1-yl)phenyl)-4-oxo-4-((R)-3-(2-(5,6,7,8-tetrahydro-1,8-naphthyridin-2-yl)ethyl)pyrrolidin-1-yl)butanoic acid (Intermediate 45) (65 mg, 0.13 mmol) in THF (1 mL) was treated at room temperature with borane-THF solution in THF (1M, 2 mL) under nitrogen. The mixture was stirred at ambient temperature overnight. In the morning AcOH (0.5 mL) was added to quench the excess borane, followed by 2M NaOH solution (1 mL) to break the borane complexes. The mixture was diluted with ether and washed with 2M NaOH twice, followed by brine, dried (MgSO₄) and evaporated under reduced pressure. The crude product (100 mg) was dissolved in THF (1 mL) and treated with LiAlH₄ solution in ether (1M, 1.5 mL) at 20° C. under nitrogen. The mixture was kept at 20° for 30 min and then was heated to 50° C. for 2 h. More LiAlH₄ solution (1M, 0.7 mL) was added and the mixture was heated to 60° C. for 45 min. LCMS (Method A) RT=1.12 min, 58%, m/z 474 (M+H)+ for product and RT=1.23 min, 27%, m/z 488 (M+H)+ for amide. Temperature was raised to 80° C. for an additional 1 h, however, the reaction seems to have stopped. The reaction mixture was quenched by addition of 2M NaOH solution (1 mL) and ether. The white solid was collected by filtration, washed with ether and ethyl acetate. The filtrate and washings were evaporated under reduced pressure. The residue (58 mg) was purified by MDAP (Method A) to give the title compound (30 mg, 49%) as a yellow gum: LCMS (Method A) RT=1.10 min, 93%, ES+ve m/z 474 (M+H)+; $[\alpha]_D^{20}$=+7.0 (c=0.859 in CHCl₃); ¹H NMR (DMSO-d₆, 600 MHz) δ 7.40-7.36 (m, 1H), 7.28-7.26 (m, 1H), 7.28-7.25 (m, 1H), 7.20 (d, J=7.7 Hz, 1H), 6.99 (d, J=7.3 Hz, 1H), 6.22 (d, J=7.2 Hz, 1H), 6.20 (br. s., 1H), 6.05 (s, 1H), 3.32-3.28 (m, 1H), 3.25-3.21 (m, 1H), 3.24-3.18 (m, 2H), 2.97-2.90 (m, 1H), 2.71 (t, J=8.2 Hz, 1H), 2.64 (dd, J=11.8, 7.8 Hz, 1H), 2.59 (t, J=6.2 Hz, 2H), 2.57-2.53 (m, 1H), 2.54-2.50 (m, 1H), 2.39-2.34 (m, 2H), 2.37-2.32 (m, 1H), 2.26 (s, 3H), 2.17 (s, 3H), 2.07-2.01 (m, 1H), 1.94 (dd, J=13.1, 7.4 Hz, 1H), 1.97-1.88 (m, 1H), 1.87-1.79 (m, 1H), 1.74 (dt, J=11.5, 6.0 Hz, 2H), 1.67-1.59 (m, 1H), 1.60-1.53 (m, 2H), 1.31-1.24 (m, 1H). ¹H NMR spectrum showed a ~3:1 mixture of closely related signals, in accord with a mixture of diastereoisomers of the title compound. The major component matched Intermediate 33 Isomer 1, the minor component matched Intermediate 33 Isomer 2. Analytical Chiral HPLC (4.6×250 mm Chiralpak1 AD) eluting with 10% EtOH-heptane containing 0.1% isopropylamine, flow rate=1 mL/min, injecting 15 μL, detecting at 235 nm RT=22.5 min, 78.9% and RT=26.9 min, 21.1%.

Solubility

The Chemiluminescent nitrogen detection (CLND) kinetic solubility was measured according to N. Bhattachar et. al. *J. Pharm. Biomed. Anal.* 2006, 41, 152-157 and found to be: for Example 1, 504 μM; for Example 2, 249 μM; for Example 3, 276 μM; for Example 4, 388 μM; for Example 5, 470 μM; for Example 6, 437 μM; for Example 7, 349 μM.

Biological Assays

Adhesion Assays:
Reagents and methods utilised were as described [Ludbrook et al, *Biochem. J.* 2003, 369, 311), with the following points of clarification. The following cell lines were used, with ligands in brackets: K562-$\alpha_5\beta_1$ (Fibronectin), K562-$\alpha_v\beta_3$ (LAP-b₁), K562-$\alpha_v\beta_5$ (Vitronectin), K562-$\alpha_v\beta_6$ (LAP-b₁), K562-$\alpha_v\beta_8$ (LAP-b₁). The divalent cation used to facilitate adhesion was 2 mM MgCl₂. Adhesion was quantified by cell labelling with the fluorescent dye BCECF-AM (Life Technologies), where cell suspensions at 6×10⁶ cells/mL were incubated with 0.66 mL/mL of 30 mM BCECF-AM at 37° C. for 10 minutes, before dispensing into the assay plate. At the assay conclusion cells that adhered were lysed using 50 μL/well of 0.5% Triton X-100 in H₂O to release fluorescence. Fluorescence intensity was detected using an Envision® plate reader (Perkin Elmer). For active antagonists in the assay, data were fitted to a 4 parameter logistic equation for $IC_{50}$ determinations.

Binding of human soluble $\alpha_v\beta_6$ protein to an RGD-containing Peptide by Fluorescence Polarisation Assay:

The extracellular domains of $\alpha_v$ and $\beta_6$ were co-expressed from a pFastBac dual construct using the baculovirus expression system. The expressed protein contained amino acid 31-987 of $\alpha_v$ followed by a Tev cleavage site, a Fos epitope tag and a 6His tag, amino acids 21-707 of $\beta_6$ followed by a Prescission protease site, a Jun epitope tag and a FLAG tag. The protein was secreted into the media on expression; it was purified using diafiltration followed by purification using the His tag followed by the FLAG tag and then size exclusion chromatography. This yielded material of greater than 95% pure. A fluorescent binding peptide based on $LAP\beta_3$ was synthesised chemically, having the sequence Ac-GRRGDLGRLK(Cy3B)-NH2. An assay buffer of 25 mM HEPES pH7.4, 150 mM NaCl, 1 mM CHAPS and 400 mM $MgCl_2$ was used. To black low volume 384 well plates were added 0.1 mL/well of test compound in 100% DMSO, followed by 3 mL/well of 10 nM $\alpha_v\beta_6$ protein. Plates were incubated at room temperature for 15 minutes before addition of 3 mL/well of 4 nM fluorescent RGD-containing peptide. Plates were incubated for 60 minutes at room temperature, and fluorescence polarization detected using an Envision® plate reader (Perkin Elmer) with excitation at 531 nm and emission measured at 590 nm. For active antagonists in the assay, data were fitted to a 4 parameter logistic equation for $IC_{50}$ determinations.

The affinity ($pIC_{50}$) for the human. $\alpha_v\beta_6$ protein in the Fluorescence Polarisation Assay for Example 1 was 8.1, whereas its affinity in the cell Adhesion Assays was for: $\alpha_v\beta_6$ $PIC_{50}=8.4$; $\alpha_v\beta_3$ $pIC_{50}=6$; $\alpha_v\beta_5$ $pIC_{50}=6.9$; $\alpha_v\beta_8$ $pIC_{50}=7.7$.

The affinity ($pIC_{50}$) for the human $\alpha_v\beta_6$ protein in the Fluorescence Polarisation Assay for Example 2 was 7.8, whereas its affinity in the cell Adhesion Assays was for: $\alpha_v\beta_6$ $pIC_{50}=\alpha_v\beta_6$ $pIC_{50}=8.4$; $\alpha_v\beta_3$ $pIC_{50}=6$; $\alpha_v\beta_5$ $pIC_{50}=6.8$; $\alpha_v\beta_8$ $pIC_{50}=7.7$.

The affinity ($pIC_{50}$) for the human $\alpha_v\beta_6$ protein in the Fluorescence Polarisation Assay for Example 3 was 8.2, whereas its affinity in the cell Adhesion Assays was for: $\alpha_v\beta_6$ $pIC_{50}=8.1$; $\alpha_v\beta_3$ $pIC_{50}=6$; $\alpha_v\beta_5$ $pIC_{50}=6.9$; $\alpha_v\beta_8$ $pIC_{50}=7.7$.

The affinity ($pIC_{50}$) for the human $\alpha_v\beta_6$ protein in the Fluorescence Polarisation Assay for Example 4 was 8.2, whereas its affinity in the cell Adhesion Assays was for: $\alpha_v\beta_6$ $pIC_{50}=8.6$; $\alpha_v\beta_3$ $pIC_{50}=6.9$; $\alpha_v\beta_5$ $pIC_{50}=7.5$; $\alpha_v\beta_8$ $pIC_{50}=7.8$.

The affinity ($pIC_{50}$) for the human $\alpha_v\beta_6$ protein in the Fluorescence Polarisation Assay for Example 5 was 7.8, whereas its affinity in the cell Adhesion Assays was for: $\alpha_v\beta_6$ $pIC_{50}=8.1$; $\alpha_v\beta_3$ $pIC_{50}=6.1$; $\alpha_v\beta_5$ $pIC_{50}=6.6$; $\alpha_v\beta_8$ $pIC_{50}=7.4$.

The affinity ($pIC_{50}$) for the human $\alpha_v\beta_6$ protein in the Fluorescence Polarisation Assay for Example 6 was 7.7, whereas its affinity in the cell Adhesion Assays was for: $\alpha_v\beta_6$ $pIC_{50}=8.1$; $\alpha_v\beta_3$ $pIC_{50}=5.8$; $\beta_v\beta_5$ $pIC_{50}=6.6$; $\alpha_v\beta_8$ $pIC_{50}=7.3$.

The affinity ($pIC_{50}$) for the human $\alpha_v\beta_6$ protein in the Fluorescence Polarisation Assay for Example 7 was 7.8, whereas its affinity in the cell Adhesion Assays was for: $\alpha_v\beta_6$ $pIC_{50}=8.4$; $\alpha_v\beta_3$ $pIC_{50}=6.7$; $\alpha_v\beta_5$ $pIC_{50}=7.4$; $\alpha_v\beta_8$ $pIC_{50}=7.3$.

The invention claimed is:

1. A compound of formula (I)

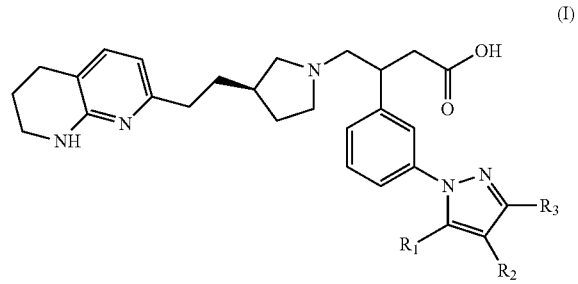

wherein
$R_1$ represents a hydrogen atom, a methyl group, or an ethyl group;
$R_2$ represents a hydrogen atom or a fluorine atom; and
$R_3$ represents a hydrogen atom, a methyl group, or an ethyl group;
or a pharmaceutically acceptable salt thereof.

2. A compound of formula (I) according to claim 1 wherein $R_1$ represents a methyl group, $R_2$ represents a hydrogen atom, and $R_3$ represents a methyl group; or a pharmaceutically acceptable salt thereof.

3. A compound of formula (I) according to claim 1 wherein $R_1$ represents a methyl group, $R_2$ represents a hydrogen atom, and $R_3$ represents a hydrogen atom; or a pharmaceutically acceptable salt thereof.

4. A compound of formula (I) according to claim 1 wherein $R_1$ represents a methyl group, $R_2$ represents a fluorine atom, and $R_3$ represents methyl group; or a pharmaceutically acceptable salt thereof.

5. A compound of formula (I) according to claim 1 wherein $R_1$ represents a hydrogen atom, $R_2$ represents a hydrogen atom, and $R_3$ represents a hydrogen atom; or a pharmaceutically acceptable salt thereof.

6. A compound of formula (I) according to claim 1 wherein $R_1$ represents an ethyl group, $R_2$ represents a hydrogen atom, and $R_3$ represents a methyl group; or a pharmaceutically acceptable salt thereof.

7. A compound of formula (I) according to claim 1 wherein $R_1$ represents an ethyl group, $R_2$ represents a hydrogen atom, and $R_3$ represents an ethyl group; or a pharmaceutically acceptable salt thereof.

8. A compound of formula (I) according to claim 1 wherein $R_1$ represents a hydrogen atom, $R_2$ represents a hydrogen atom, and $R_3$ represents a methyl group; or a pharmaceutically acceptable salt thereof.

9. A compound of formula (I):

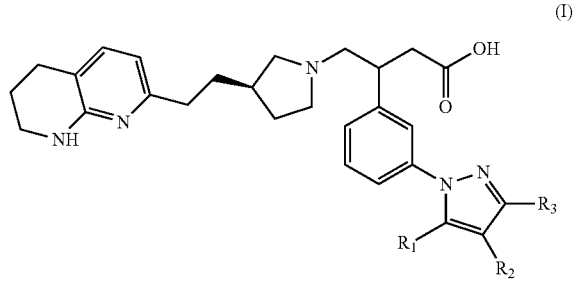

wherein
$R_1$ represents a hydrogen atom, a methyl group, or an ethyl group;

R₂ represents a hydrogen atom or a fluorine atom; and R₃ represents a hydrogen atom, a methyl group, or an ethyl group.

10. A compound of formula (I) according to claim 9 which is selected from the group consisting of:
    3-(3-(3,5-Dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid;
    3-(3-(5-Methyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid;
    3-(3-(5-Ethyl-3-methyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid;
    3-(3-(1H-Pyrazol-1-yl)phenyl)-4-((R)-3-(2-(5,6,7,8-tetrahydro-1,8-naphthyridin-2-yl)ethyl)pyrrolidin-1-yl)butanoic acid;
    3-(3-(3,5-Diethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid;
    3-(3-(4-Fluoro-3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid; and
    3-(3-(3-Methyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid.

11. A compound of formula (I) according to claim 1 which is 3-(3-(3,5-Dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid:

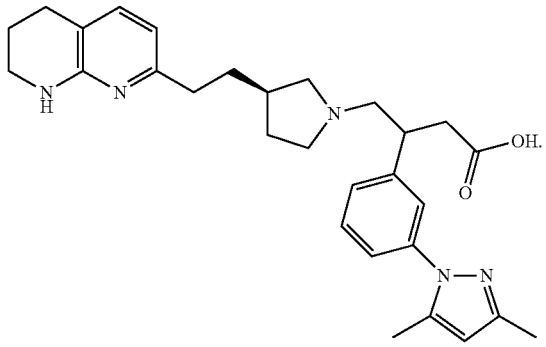 [SMILES: Cc1cc(C)n(-c2cccc(C(CC(=O)O)CN3CC[C@@H](CCc4ccc5c(n4)NCCC5)C3)c2)n1]

12. A compound of formula (I) according to claim 1 which is (S)-3-(3-(3,5-dimethyl-1H-pyrazol-1-yl)phenyl)-4-((R)-3-(2-(5,6,7,8-tetrahydro-1, 8-naphthyridin-2-yl)ethyl)pyrrolidin-1-yl)butanoic acid

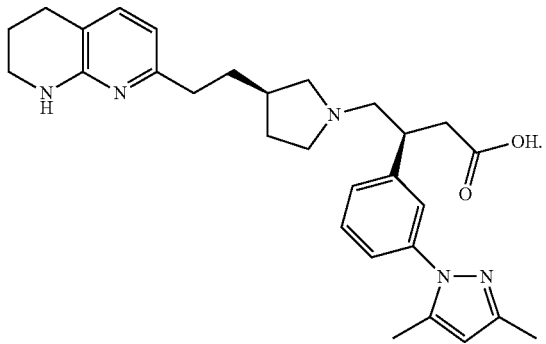 [SMILES: Cc1cc(C)n(-c2cccc([C@H](CC(=O)O)CN3CC[C@@H](CCc4ccc5c(n4)NCCC5)C3)c2)n1]

13. A compound according to claim 1 which is 3-(3-(3,5-Dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid hydrochloride salt.

14. A compound according to claim 1 which is (S)-3-(3-(3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid hydrochloride salt.

15. A method for the treatment of idiopathic pulmonary fibrosis in a human in need thereof comprising administering to the human a therapeutically effective amount of a compound of formula (I)—according to claim 1 or a pharmaceutically acceptable salt thereof.

16. A pharmaceutical composition comprising a compound of formula (I) according to claim 1, or a pharmaceutically acceptable salt thereof, and one or more pharmaceutically acceptable carriers, diluents, or excipients.

17. A pharmaceutical composition comprising (S)-3-(3-(3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl) butanoic acid

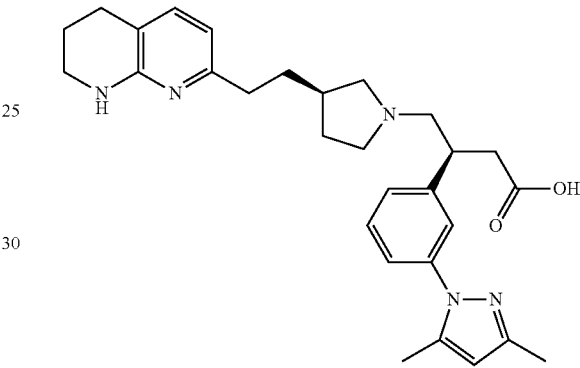

or a pharmaceutically acceptable salt thereof, and one or more pharmaceutically acceptable carriers, diluents, or excipients.

18. A pharmaceutical composition comprising (S)-3-(3-(3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl) butanoic acid hydrochloride salt and one or more pharmaceutically acceptable carriers, diluents, or excipients.

19. A method for the treatment of idiopathic pulmonary fibrosis in a human in need thereof comprising administering to the human a therapeutically effective amount of (S)-3-(3-(3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl) butanoic acid

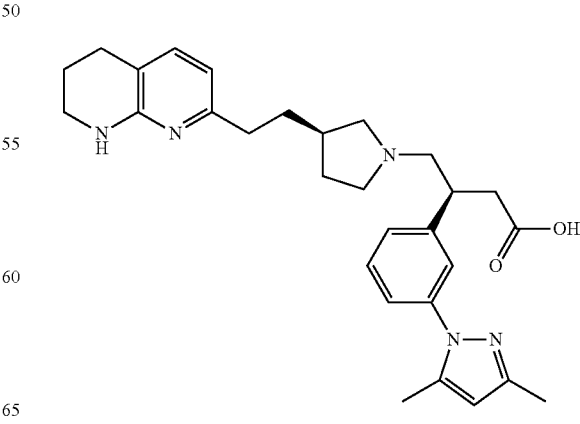

or a pharmaceutically acceptable salt thereof.

20. A method for the treatment of idiopathic pulmonary fibrosis in a human in need thereof comprising administering to the human a therapeutically effective amount of (S)-3-(3-(3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl) butanoic acid hydrochloride salt.

21. A method for the treatment of pulmonary fibrosis in a human in need thereof comprising administering to the human a therapeutically effective amount of a compound of formula (I) according to claim 1 or a pharmaceutically acceptable salt thereof.

22. A method for the treatment of pulmonary fibrosis according to claim 21, wherein the pulmonary fibrosis is non-specific interstitial pneumonia or usual interstitial pneumonia.

23. A method for the treatment of hepatic fibrosis in a human in need thereof comprising administering to the human a therapeutically effective amount of a compound of formula (I) according to claim 1 or a pharmaceutically acceptable salt thereof.

24. A method for the treatment of hepatic fibrosis according to claim 23, wherein the hepatic fibrosis is viral induced fibrosis, hepatitis C, primary biliary cirrhosis, alcoholic liver disease, non-alcoholic fatty liver disease, or non-alcoholic steatohepatitis.

25. A method for the treatment of renal fibrosis in a human in need thereof comprising administering to the human a therapeutically effective amount of a compound of formula (I) according to claim 1 or a pharmaceutically acceptable salt thereof.

26. A method for the treatment of renal fibrosis according to claim 25, wherein the renal fibrosis is diabetic nephropathy, IgA nephropathy, or focal segmental glomerulosclerosis.

27. A method for the treatment of pulmonary fibrosis in a human in need thereof comprising administering to the human a therapeutically effective amount of (S)-3-(3-(3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid

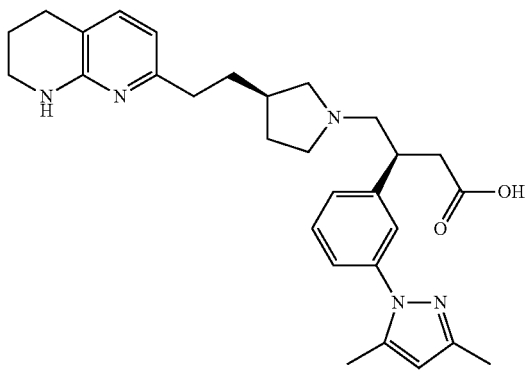 [SMILES: Cc1cc(C)n(-c2cccc([C@H](CC(=O)O)CN3CC[C@@H](CCc4ccc5c(n4)NCCC5)C3)c2)n1]

or a pharmaceutically acceptable salt thereof.

28. A method for the treatment of pulmonary fibrosis according to claim 27, wherein the pulmonary fibrosis is non-specific interstitial pneumonia or usual interstitial pneumonia.

29. A method for the treatment of hepatic fibrosis in a human in need thereof comprising administering to the human a therapeutically effective amount of (S)-3-(3-(3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid

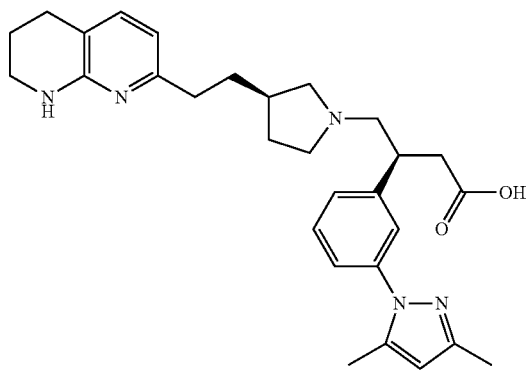 [SMILES: Cc1cc(C)n(-c2cccc([C@H](CC(=O)O)CN3CC[C@@H](CCc4ccc5c(n4)NCCC5)C3)c2)n1]

or a pharmaceutically acceptable salt thereof.

30. A method for the treatment of hepatic fibrosis according to claim 29, wherein the hepatic fibrosis is viral induced fibrosis, hepatitis C, primary biliary cirrhosis, alcoholic liver disease, non-alcoholic fatty liver disease, or non-alcoholic steatohepatitis.

31. A method for the treatment of renal fibrosis in a human in need thereof comprising administering to the human a therapeutically effective amount of (S)-3-(3-(3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid

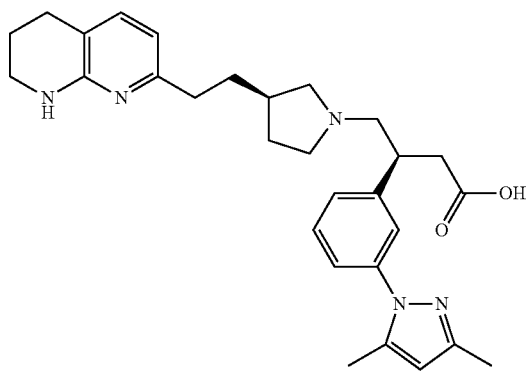 [SMILES: Cc1cc(C)n(-c2cccc([C@H](CC(=O)O)CN3CC[C@@H](CCc4ccc5c(n4)NCCC5)C3)c2)n1]

or a pharmaceutically acceptable salt thereof.

32. A method for the treatment of renal fibrosis according to claim 31, wherein the renal fibrosis is diabetic nephropathy, IgA nephropathy, or focal segmental glomerulosclerosis.

33. A method for the treatment of pulmonary fibrosis in a human in need thereof comprising administering to the human a therapeutically effective amount of (S)-3-(3-(3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid hydrochloride salt.

34. A method for the treatment of pulmonary fibrosis according to claim 33, wherein the pulmonary fibrosis is non-specific interstitial pneumonia or usual interstitial pneumonia.

35. A method for the treatment of hepatic fibrosis in a human in need thereof comprising administering to the human a therapeutically effective amount of (S)-3-(3-(3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid hydrochloride salt.

36. A method for the treatment of hepatic fibrosis according to claim 35, wherein the hepatic fibrosis is viral induced fibrosis, hepatitis C, primary biliary cirrhosis, alcoholic liver disease, non-alcoholic fatty liver disease, or non-alcoholic steatohepatitis.

37. A method for the treatment of renal fibrosis in a human in need thereof comprising administering to the human a therapeutically effective amount of (S)-3-(3-(3,5-dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid hydrochloride salt.

38. A method for the treatment of renal fibrosis according to claim 37, wherein the renal fibrosis is diabetic nephropathy, IgA nephropathy, or focal segmental glomerulosclerosis.

39. A compound of formula (I) according to any of claims 1-9 having the configuration:

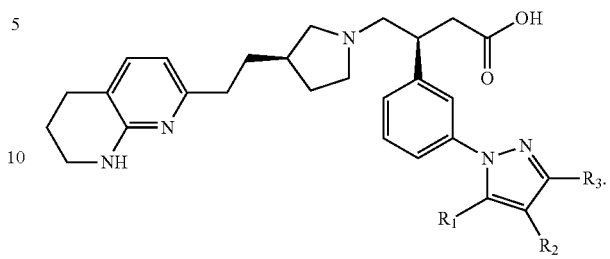

* * * * *